US010864263B2

(12) United States Patent
Barouch et al.

(10) Patent No.: US 10,864,263 B2
(45) Date of Patent: Dec. 15, 2020

(54) METHOD OF PROVIDING SAFE ADMINISTRATION OF ADENOVIRAL VECTORS ENCODING A ZIKA VIRUS ANTIGEN

(71) Applicants: Janssen Pharmaceuticals, Inc., Titusville, NJ (US); Beth Israel Deaconess Medical Center, Inc., Boston, MA (US)

(72) Inventors: Dan Barouch, Newton, MA (US); Macaya Julie Douoguih, Reston, VA (US); Gaston Rafael Picchio, Flemington, NJ (US)

(73) Assignees: Janssen Pharmaceuticals, Inc., Titusville, NJ (US); Beth Israel Deaconess Medical Center. Inc., Boston, MA (US)

( * ) Notice: Subject to any disclaimer, the term of this patent is extended or adjusted under 35 U.S.C. 154(b) by 0 days.

(21) Appl. No.: 16/194,868

(22) Filed: Nov. 19, 2018

(65) Prior Publication Data
US 2019/0151434 A1 May 23, 2019

Related U.S. Application Data

(60) Provisional application No. 62/588,635, filed on Nov. 20, 2017.

(51) Int. Cl.
| *A61K 39/13* | (2006.01) |
| *A61K 47/69* | (2017.01) |
| *A61P 31/14* | (2006.01) |
| *A61K 9/00* | (2006.01) |
| *A61K 39/00* | (2006.01) |
| *A61K 39/12* | (2006.01) |

(52) U.S. Cl.
CPC .......... *A61K 39/12* (2013.01); *A61K 9/0019* (2013.01); *A61K 47/6901* (2017.08); *A61P 31/14* (2018.01); *A61K 2039/6075* (2013.01); *C12N 2710/10343* (2013.01); *C12N 2770/24134* (2013.01)

(58) Field of Classification Search
CPC .. A61K 39/12; A61K 47/6901; A61K 9/0019; A61K 2039/6075; A61P 31/14; C12N 2770/24134; C12N 2710/10343; C12N 2770/24122; C12N 2799/02; C12N 2799/021; C12N 2799/022; C12N 2799/06; C12N 2799/04; C12N 2710/10311; C12N 2710/10334; C12N 2710/10341; C12N 2710/10344; C12N 2710/10345; C12N 2710/10011; C12N 2710/10021; C12N 2710/10034; C12N 2710/10041; C12N 2710/10043; C12N 2710/10044; Y02A 50/30
See application file for complete search history.

(56) References Cited

U.S. PATENT DOCUMENTS

| 4,603,112 | A | 7/1986 | Paoletti et al. |
| 5,639,649 | A | 6/1997 | Almond et al. |
| 5,643,576 | A | 7/1997 | Johnston et al. |
| 5,762,938 | A | 6/1998 | Paoletti et al. |
| 5,801,030 | A | 9/1998 | McVey et al. |
| 6,083,716 | A | 7/2000 | Wilson et al. |
| 7,270,811 | B2 | 9/2007 | Bout et al. |
| 2015/0291935 | A1* | 10/2015 | Barouch ............... A61K 39/00 424/199.1 |
| 2019/0136205 | A1* | 5/2019 | Barouch ............... A61K 39/00 |

FOREIGN PATENT DOCUMENTS

| WO | 200070071 A1 | 11/2000 |
| WO | 2003104467 A1 | 12/2003 |
| WO | 2004001032 A2 | 12/2003 |
| WO | 2005071093 A2 | 8/2005 |
| WO | 2006040330 A2 | 4/2006 |
| WO | 2007104792 A2 | 9/2007 |
| WO | 2010085984 A1 | 8/2010 |
| WO | 2010086189 A2 | 8/2010 |
| WO | 2012082918 A1 | 6/2012 |
| WO | 2017214596 A1 | 12/2017 |

OTHER PUBLICATIONS

Mendieta-Condado ER, et. al. Polyprotein [Zika virus]. GenBank: AMQ34004. Dep. Mar. 16, 2016.*
Barouch DH, Alter G, Broge T, et. al. Protective efficacy of adenovirus/protein vaccines against SIV challenges in rhesus monkeys. Science. Jul. 17, 2015;349(6245):320-4. Epub Jul. 2, 2015.*
Abbink, et al., "Comparative Seroprevalence and Immunogenicity of Six Rare Serotype Recombinant Adenovirus Vaccine Vectors from Subgroups B and D", Journal of Virology, vol. 81, No. 9, pp. 4654-4663, (May 2007).
Abbink, et al., "Durability and Correlates of Vaccine Protection Against Zika Virus in Rhesus Monkeys", Sci. Transl. Med. vol. 9, No. 420, (Dec. 2017).
Abbink, et al., "Protective Efficacy of Multiple Vaccine Platforms Against Zika Virus Challenge in Rhesus Monkeys", Science, vol. 353, No. 6304, pp. 1129-1132, (2016).
Baden et al., "First-in-Human Evaluation of the Safety and Immunogenicity of a Recombinant Adenovirus Serotype 26 HIV-1 Env Vaccine (IPCAVD 001)," The Journal of Infectious Diseases, vol. 207, pp. 240-247 (2013).
Bangari et al, "Development of nonhuman adenoviruses as vaccine vectors," Vaccine, vol. 24, No. 7, pp. 849-862 (2006).
Barzon et al., "Current views on Zika virus vaccine development," Expert Opinion on Biological Therapy, vol. 17, No. 10, pp. 1185-1192 (2017).

(Continued)

*Primary Examiner* — Rachel B Gill
(74) *Attorney, Agent, or Firm* — Ice Miller LLP

(57) ABSTRACT

Provided are methods for generating an immune response against a Zika virus in a human subject in need thereof. The methods comprise administering to the subject a pharmaceutical composition comprising adenoviral vectors encoding a Zika virus antigen and a pharmaceutically acceptable carrier.

6 Claims, 2 Drawing Sheets
Specification includes a Sequence Listing.

(56) References Cited

OTHER PUBLICATIONS

ClinicalTrials.Gov: "NCT03356561: A Study to Evaluate the Safety, Reactogenicity and Immunogenicity of Ad26. ZIKV.001 in Healthy Adult Volunteers," Nov. 29, 2017 (Nov. 29, 2017), XP05552132, Retrieved from the Internet: URL:https://clinicaltrials.gov/ct2/show/NCT03356561 [retrieved on Feb. 5, 2019].

Cohen et al, "Chimpanzee adenovirus CV-68 adapted as a gene delivery vector interacts with the coxsackievirus and adenovirus receptor," Journal of General Virology, vol. 83, Pt. 1, pp. 151-155 (2002).

Cox et al., "Adenoviral vector type 26 encoding Zika virus (ZIKV) M-Env antigen induces humoral and cellular immune responses and protects mice and nonhuman primates against ZIKV challenge," PLOS ONE, vol. 13, No. 8, pp. 1-19 (Aug. 24, 2018).

Farina et al, "Replication-Defective Vector Based on a Chimpanzee Adenovirus," Journal of Virology, vol. 75, No. 23, pp. 11603-11613 (2001).

Havenga et al, "Novel replication-incompetent adenoviral B-group vectors: high vector stability and yield in PER.C6 cells," Journal of General Virology, vol. 87, pp. 2135-2143 (2006).

International Search Report and Written Opinon dated Feb. 18, 2019 in International Application No. PCT/US2018/061743.

Kim et al., "Preventative Vaccines for Zika Virus Outbreak: Preliminary Evaluation," EBioMedicine, vol. 13, pp. 315-320 (Nov. 1, 2016).

Kobinger et al, "Chimpanzee adenovirus vaccine protects against Zaire Ebola virus," Virology, vol. 346, pp. 394-401 (2006).

Lasaro et al., "New insights on adenovirus as vaccine vectors.," Molecular Therapy, vol. 17, No. 8, pp. 1333-1339 (Aug. 2009).

Lopez-Camacho et al., "Ratioanl Zika vaccine design via the modulation of antigen membrane anchors in chimpanzee adenoviral vectors," Nature Communications, vol. 9, No. 1, pp. 1-11 (Jun. 22, 2018).

Modjarrad et al., "Preliminary aggregate safety and immunogenicity results from three trials of a purified inactivated Zika virus vaccine candidate: phase 1, randomised, double-blind, placebo-controlled clinical trials," The Lancet, vol. 391, No. 10120, pp. 563-571 (Feb. 2018).

Tatsis et al, "A CD46-binding Chimpanzee Adenovirus Vector as a Vaccine Carrier.", Molecular Therapy, vol. 15, pp. 608-617, (Mar. 2007).

Vogels et al., "Replication-Deficient Human Adenovirus Type 35 Vectors for Gene Transfer and Vaccination: Efficient Human Cell Infection and Bypass of Preexisting Adenovirus Immunity.", Journal of Virology, vol. 77, No. 15, pp. 8263-8271, (Aug. 2003).

Wattanapitayakul et al., "Recent developments in gene therapy for cardiac disease," Biomed. & Pharmacother., vol. 54, pp. 487-504 (2000).

Abbink et al., "Zika virus vaccines," Nature Review, Microbiol, vol. 16, No. 10, pp. 594-600 (Jun. 19, 2018).

\* cited by examiner

US 10,864,263 B2

METHOD OF PROVIDING SAFE ADMINISTRATION OF ADENOVIRAL VECTORS ENCODING A ZIKA VIRUS ANTIGEN

FIELD OF THE INVENTION

This invention relates to biotechnology. More particularly, to methods of administering adenovirus viral particles comprising an optimized, non-naturally occurring Zika virus (ZIKV) nucleic acid molecule to a subject in need thereof for preventing a ZIKV infection and/or symptoms caused by a ZIKV.

REFERENCE TO SEQUENCE LISTING SUBMITTED ELECTRONICALLY

This application contains a sequence listing, which is submitted electronically via EFS-Web as an ASCII formatted sequence listing with a file name "688097.565US Sequence Listing" and a creation date of Nov. 16, 2018, and having a size of 186 kb. The sequence listing submitted via EFS-Web is part of the specification and is herein incorporated by reference in its entirety.

BACKGROUND OF THE INVENTION

Zika virus (ZIKV) is a flavivirus that is responsible for an unprecedented current epidemic in Brazil and the Americas. ZIKV has been causally associated with microcephaly, intrauterine growth restriction, and other birth defects in humans and in murine models. ZIKV is believed to cause neuropathology in developing fetuses by crossing the placenta and targeting cortical neural progenitor cells, leading to impaired neurogenesis and resulting in microcephaly and other congenital malformations.

The World Health Organization declared the clusters of microcephaly and neurological disorders and their association with ZIKV infection to be a global public health emergency on Feb. 1, 2016. ZIKV also has been associated with neurologic conditions such as Guillain-Barré syndrome. While the rapid development of a safe and effective ZIKV vaccine is a global health priority, very little is currently known about ZIKV immunology and mechanisms of immune protection.

Accordingly, there is an unmet need in the field for ZIKV vaccines.

BRIEF SUMMARY OF THE INVENTION

Provided herein are methods for generating an immune response against a Zika virus in a human subject in need thereof. A method according to an embodiment of the invention comprises administering to the subject a pharmaceutical composition comprising adenoviral vectors comprising a nucleic acid sequence encoding a Zika virus antigen and a pharmaceutically acceptable carrier, wherein about $1 \times 10^{10}$ adenoviral vectors to about $5 \times 10^{11}$ adenoviral vectors, preferably about $5 \times 10^{10}$ adenoviral vectors to about $1 \times 10^{11}$ adenoviral vectors are administered to the subject in need thereof. In a preferred embodiment, about $5 \times 10^{10}$ adenoviral vectors are administered per dose to the human subject in need thereof. In another preferred embodiment, about $1 \times 10^{11}$ adenoviral vectors are administered per dose to the human subject in need thereof.

In certain embodiments, the pharmaceutical composition is administered via an intramuscular injection to the human subject in need thereof. In certain embodiments, the pharmaceutical composition is administered to the human subject as a single dose. In certain embodiments, the pharmaceutical composition is administered to the human subject as a double dose. The first and second dose of the pharmaceutical composition can be administered to the human subject about four weeks, about eight weeks, about twelve weeks, about three months, about six months, about nine months, about one year, or about two years apart. In certain embodiments, the first and second dose of the pharmaceutical composition can be administered to the human subject about eight weeks apart.

In certain embodiments, the Zika virus antigen comprises the amino acid sequence of SEQ ID NO:2, 4, 6, 8, 10, or 12. In certain embodiments, the Zika virus antigen comprises the amino acid sequence of SEQ ID NO:2.

In certain embodiments, the adenoviral vectors are of the Ad26 serotype.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

DETAILED DESCRIPTION OF THE INVENTION

Figure 1A:
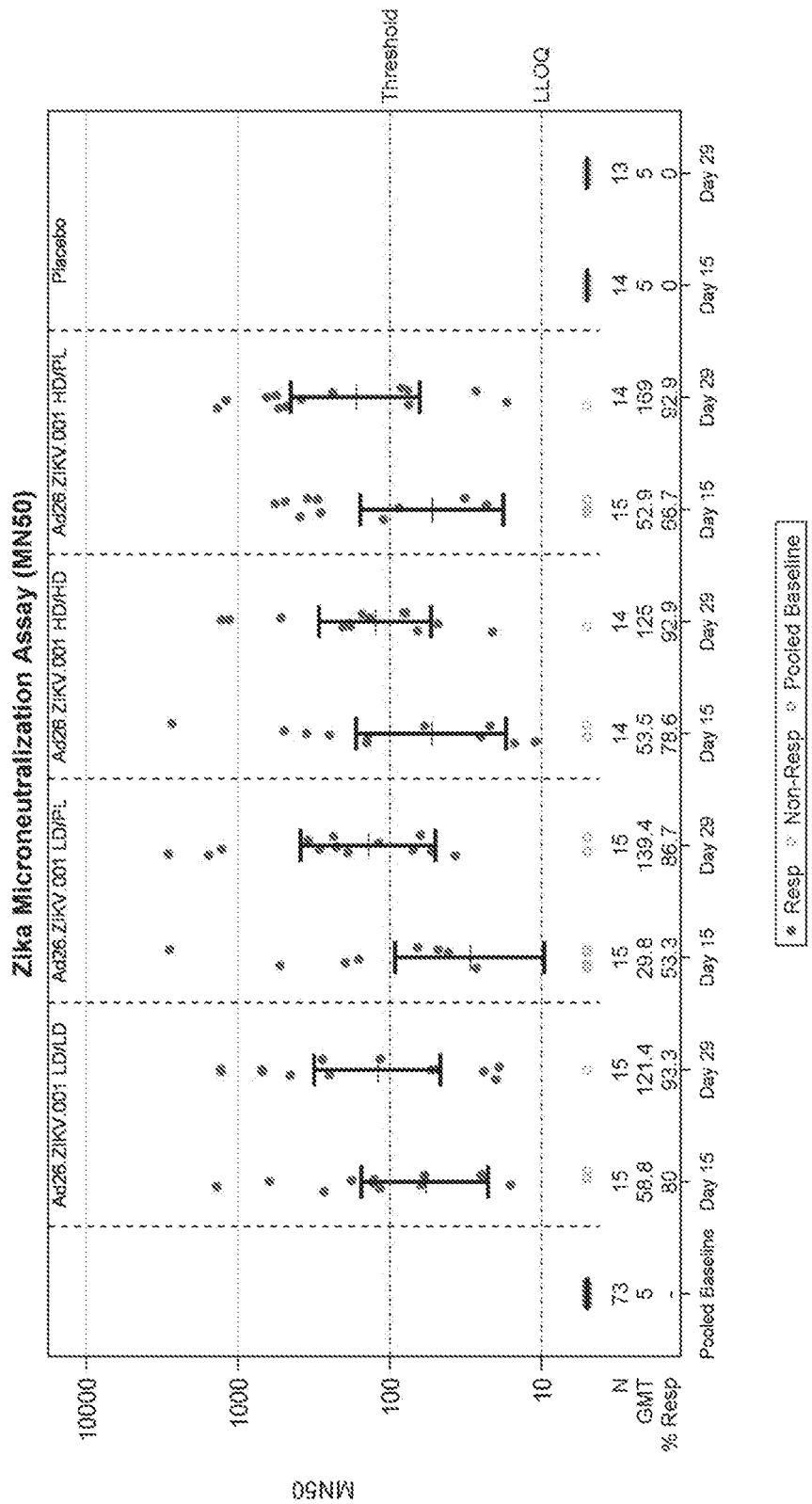
FIGS. 1A and 1B show the ZIKV neutralizing antibody response (assessed by MN50 VNA) in serum from clinical study participants at the indicated study timepoints (days 15 and 29 on FIG. 1A and days 57, 71 and 85 on FIG. 1B) for each of the tested regimens. Doses were given at days 1 and 57. Responders are depicted on FIGS. 1A and 1B with filled circles, non-responders are depicted with open light grey circles. Pooled baseline is depicted with dark grey circles on FIG. 1A on the left-hand side of the graph. LD stands for Low Dose which stands for a dose of $5 \times 10^{10}$ viral particles (vp) of Ad26.ZIKV.001; HD stands for High Dose, which stands for a dose of $1 \times 10^{11}$ vp Ad26.ZIKV.001, PL stands for Placebo.
Figure 1B:
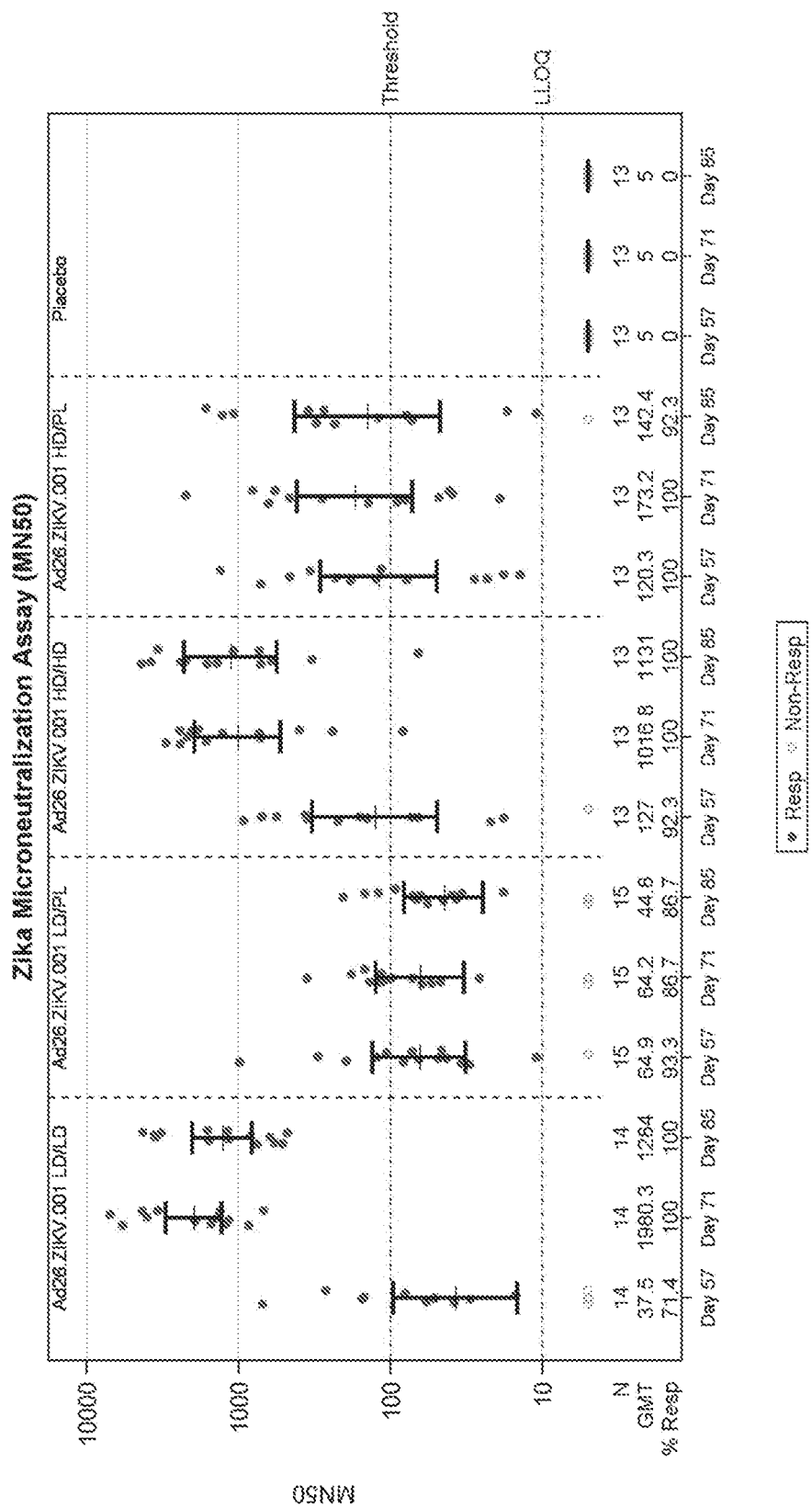

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes $\pm 10\%$ of the recited value. For example, a concentration of 1 mg/mL includes 0.9 mg/mL to 1.1 mg/mL. Likewise, a concentration range of 1% to 10% (w/v) includes 0.9% (w/v)

to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" or "patient" means any animal, preferably a mammal, most preferably a human, to whom will be or has been administered a vaccine by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, "a method of providing safe administration" means a method of administration that is effective in generating an immune response against a Zika virus without causing unacceptable adverse events, when administered to a subject.

As used herein, the phrases "unacceptable adverse events" and "unacceptable adverse reaction" shall mean all harm or undesired outcomes associated with or caused by administration of a pharmaceutical composition or therapeutic, and the harm or undesired outcome reaches such a level of severity that a regulatory agency deems the pharmaceutical composition or therapeutic unacceptable for the proposed use. Examples of unacceptable adverse events or reactions when used in the context of administration of adenoviral particles comprising a nucleic acid molecule encoding a Zika virus antigen can include, but is not limited to, swelling, injection side pain, headache, malaise, muscle ache, nausea, and fever.

In certain embodiments, "safe treatment" and "safe administration" when used with respect to administration of adenoviral vectors comprising a nucleic acid molecule encoding a Zika virus antigen means reduced adverse events including, but not limited to, swelling, injection side pain, headache, malaise, muscle ache, nausea, and fever.

The terms "identical" or percent "identity," in the context of two or more nucleic acids or polypeptide sequences (e.g., Zika antigen polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "immune response" or "protective immune response" means that the vaccinated subject is able to control an infection (e.g., a Zika virus (ZIKV) infection) with the pathogenic agent against which the vaccination was done (e.g., a ZIKV antigen). The pathogenic agent can, for example, be an antigenic gene product or antigenic protein, or a fragment thereof. Usually, the subject having developed an "immune response" or a "protective immune response" develops only mild to moderate clinical symptoms or no symptoms at all. Usually, a subject in which an "immune response" or "protective immune response" against a Zika virus has been generated, will not develop disease manifestations or those disease manifestations will be milder, and ultimately the subject will not die as a result of the infection with said virus. In addition, a subject in which an "immune response" or "protective immune response" against a Zika virus has been generated, will have a reduced chance of brain abnormalities in her infants exposed to the virus in utero.

By "generating an immune response" or "promoting an immune response" or "provoking an immune response" is meant eliciting a humoral response (e.g., the production of antibodies) or a cellular response (e.g., the activation of T cells, macrophages, neutrophils, and/or natural killer cells) directed against, for example, one or more infective agents (e.g., a virus (e.g., a ZIKV)) or protein targets in a subject to which the pharmaceutical composition (e.g., an immunogenic composition or vaccine) has been administered.

By "immunogen" or "antigen" is meant any polypeptide that can induce an immune response in a subject upon administration. In some embodiments, the immunogen or antigen is encoded by a nucleic acid molecule that may be incorporated into, for example, a polynucleotide or vector of the invention, for subsequent expression of the immunogen or antigen (e.g., a gene product of interest, or fragment thereof (e.g., a polypeptide)). In some embodiments, the immunogen is derived from a ZIKV (e.g., a ZIKV from the Asian and/or African lineage (e.g., ZIKV strain BeH815744 (accession number KU365780 (SEQ ID NOs: 15-16))). In some embodiments, the immunogen is administered in the context of a nucleic acid molecule expressing a polypeptide that is derived from a ZIKV (e.g., a ZIKV from the Asian and/or African lineage (e.g., ZIKV strain BeH815744 (accession number KU365780 (SEQ ID NOs: 15-16))).

The term "immunogenic composition" as used herein, is defined as material used to generate an immune response and may confer immunity after administration of the immunogenic composition to a subject.

By "isolated" is meant separated, recovered, or purified from a component of its natural environment. For example, a nucleic acid molecule or polypeptide of the invention may be isolated from a component of its natural environment by 1% (2%, 3%, 4%, 5%, 6%, 7%, 8% 9% 10%, 20%, 30%, 40%, 50%, 60% 70%, 80%, or 90%) or more.

Nucleic Acid Molecules, Polypeptides, and Vectors of the Invention

In PCT/US2017/36900, filed on Jun. 9, 2017, entitled "Compositions and Methods for Preventing and Treating Zika Virus Infection," which is incorporated by reference in its entirety, disclosed are Zika virus (ZIKV) polypeptides that can be used to elicit protective immune responses against a ZIKV infection when administered to a subject (e.g., a mouse or monkey) infected with or likely to be exposed to a ZIKV infection. The ZIKV polypeptides for use in pharmaceutical compositions prepared for administration can include a M-Env, prM-Env, prM-Env.dTM, prM-Env.dStem, Env, Env.dTM, and/or Env.dStem or a portion thereof. Alternatively, the ZIKV polypeptides can be encoded for by a nucleic acid molecule comprised within a vector (e.g., an adenoviral vector).

Table 1 provides the ZIKV derived polypeptide and polynucleotide molecules that can be used in pharmaceutical compositions of the invention for the safe administration and prevention of a Zika virus infection.

TABLE 1

ZIKV derived polynucleotide and polypeptide molecules

| | SEQ ID NO. | |
|---|---|---|
| Region of ZIKV | polynucleotide | polypeptide |
| M-Env | 1 | 2 |
| prM-Env.dTM | 3 | 4 |
| prM-Env.dStem | 5 | 6 |
| Env | 7 | 8 |
| Env.dTM | 9 | 10 |
| Env.dStem | 11 | 12 |
| prM-Env (full length) | 24 | 25 |
| prM-Env with JEV Stem/TM | 26 | 27 |

The nucleic acid molecules of the invention (Table 1) were designed based on the Zika virus (ZIKV) strain BeH815744 (accession number KU365780 (SEQ ID NOs: 15-16)). The nucleic acid molecules of the invention encode regions of the Zika virus (ZIKV) polyprotein, for example, the membrane and envelope (M-Env) proteins, the pre-membrane and envelope (prM-Env) region, the Env protein alone, or deletion mutants of the prM-Env or Env regions in which the transmembrane (TM) or Stem region have been removed. The nucleic acid molecules of the invention M-Env (SEQ ID NO: 1), prM-Env.dTM (SEQ ID NO: 3), prM-Env.dStem (SEQ ID NO: 5), Env (SEQ ID NO: 7), Env.dTM (SEQ ID NO: 9), and Env.dStem (SEQ ID NO: 11) have been optimized relative to the wild-type BeH815744 nucleotide sequences for improved expression in host cells (e.g., mammalian (e.g., human) host cells) and particle formation, and encode the polypeptides set forth in SEQ ID NOs: 2, 4, 6, 8, 10, or 12, respectively (Table 1). Optimization can include the addition of a leader sequence, such as a Japanese encephalitis virus (JEV) leader sequence (e.g., SEQ ID NO: 13), restriction site (e.g., SEQ ID NOs: 21-22), and/or a Kozak sequence (e.g., SEQ ID NO: 23).

The prM-Env (full length) (e.g., SEQ ID NOs: 24-25) contains the full-length sequence of the prM-Env region, while prM-Env with JEV Stem/TM (e.g., SEQ ID NOs: 26-27) includes the ZIKV prM signal region of Japanese encephalitis virus (JEV) with the final 98 amino acids comprising the stem and transmembrane regions exchanged with corresponding JEV sequences.

The nucleic acid molecules have a nucleotide sequence with at least 85% (e.g., at least 86%, 87%, 88%, 89%, 90%, 91%, 92%, 93%, 94%, 95%, 96%, 97%, 98%, 99% or 100%) sequence identity to, all or a portion of any one of SEQ ID NOs: 1, 3, 5, 7, 9, or 11, or a complementary sequence thereof. Alternatively, an isolated nucleic acid molecule has a nucleotide sequence that encodes a ZIKV polypeptide with at least 85% (e.g., at least 86%, 87%, 88%, 89%, 90%, 91%, 92%, 93%, 94%, 95%, 96%, 97%, 98%, 99% or 100%) sequence identity to an amino acid sequence of any one of SEQ ID NOs: 2, 4, 6, 8, 10, or 12.

The nucleic acid molecules of the invention may be further optimized, such as by codon optimization, for expression in a targeted mammalian subject (e.g., human).

The nucleic acid molecules can also be inserted into expression vectors, such as an adenovirus vector and incorporated into compositions of the invention. The terms "adenovirus vector" and "adenoviral vector" and "adenoviral particles" are used interchangeably and refer to a genetically-engineered adenovirus that is designed to insert a polynucleotide of interest (e.g., a polynucleotide encoding a ZIKV antigen of the invention) into a eukaryotic cell, such that the polynucleotide is subsequently expressed. Examples of adenoviruses that can be used as a viral vector of the invention include those having, or derived from, the serotypes Ad2, Ad5, Ad11, Ad12, Ad24, Ad26, Ad34, Ad35, Ad40, Ad48, Ad49, Ad50, Ad52 (e.g., RhAd52), and Pan9 (also known as AdC68); these vectors can be derived from, for example, human, chimpanzee (e.g., ChAd1, ChAd3, ChAd7, ChAd8, ChAd21, ChAd22, ChAd23, ChAd24, ChAd25, ChAd26, ChAd27.1, ChAd28.1, ChAd29, ChAd30, ChAd31.1, ChAd32, ChAd33, ChAd34, ChAd35.1, ChAd36, ChAd37.2, ChAd39, ChAd40.1, ChAd41.1, ChAd42.1, ChAd43, ChAd44, ChAd45, ChAd46, ChAd48, ChAd49, ChAd49, ChAd50, ChAd67, or SA7P), or rhesus adenoviruses (e.g., rhAd51, rhAd52, or rhAd53).

"Nucleic acid molecule" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after synthesis, such as by conjugation with a label.

By "heterologous nucleic acid molecule" is meant a nucleotide sequence that can encode proteins derived or obtained from pathogenic organisms, such as viruses, which can be incorporated into a polynucleotide or vector of the invention. Heterologous nucleic acids can also encode synthetic or artificial proteins, such as immunogenic epitopes, constructed to induce immunity. An example of a heterologous nucleic acid molecule is one that encodes one or more immunogenic peptides or polypeptides derived from a Zika virus (ZIKV). The heterologous nucleic acid molecule is one that is not normally associated with the other nucleic acid molecules found in the polynucleotide or vector into which the heterologous nucleic acid molecule is incorporated.

A "nucleic acid vaccine" or "DNA vaccine" refers to a vaccine that includes a heterologous nucleic acid molecule under the control of a promoter for expression in a subject. The heterologous nucleic acid molecule can be incorporated into an expression vector, such as a plasmid or an adenoviral vector.

The term "vaccine" as used herein, is defined as material used to provoke an immune response and that confers immunity for a period of time after administration of the vaccine to a subject.

A "promoter" is a nucleic acid sequence enabling the initiation of the transcription of a gene sequence in a messenger RNA, such transcription being initiated with the binding of an RNA polymerase on or nearby the promoter.

A nucleic acid is "operably linked" when it is placed into a structural or functional relationship with another nucleic acid sequence. For example, one segment of DNA can be operably linked to another segment of DNA if they are positioned relative to one another on the same contiguous DNA molecule and have a structural or functional relationship, such as a promoter or enhancer that is positioned relative to a coding sequence so as to facilitate transcription of the coding sequence; a ribosome binding site that is positioned relative to a coding sequence so as to facilitate translation; or a pre-sequence or secretory leader that is positioned relative to a coding sequence so as to facilitate expression of a pre-protein (e.g., a pre-protein that participates in the secretion of the encoded polypeptide). In other examples, the operably linked nucleic acid sequences are not contiguous, but are positioned in such a way that they have a functional relationship with each other as nucleic acids or as proteins that are expressed by them. Enhancers, for example, do not have to be contiguous. Linking can be accomplished by ligation at convenient restriction sites or by using synthetic oligonucleotide adaptors or linkers.

The polypeptides encoded by vectors useful for the invention are ZIKV polypeptides corresponding to, for example, the membrane and envelope (M-Env) proteins, the pre-membrane and envelope (prM-Env) region, the Env protein alone, or deletion mutants of the prM-Env or Env regions in which the transmembrane (TM) or Stem region has been removed. Exemplary polypeptides encoded by vectors useful for the invention include M-Env (SEQ ID NO: 2), prM-Env.dTM (SEQ ID NO: 4), prM-Env.dStem (SEQ ID NO: 6), Env (SEQ ID NO: 8), Env.dTM (SEQ ID NO: 10), and Env.dStem (SEQ ID NO: 12) and variants having at least 85% (e.g., at least 86%, 87%, 88%, 89%, 90%, 91%, 92%, 93%, 94%, 95%, 96%, 97%, 98%, 99% or 100%) sequence identity to, all or a portion of any one of SEQ ID NOs: 2, 4, 6, 8, 10, or 12. The polypeptides of the invention may include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, or 1800 or more continuous or non-continuous amino acids of any one of SEQ ID NOs: 2, 4, 6, 8, 10, or 12.

Polypeptides encoded by vectors useful for the invention can also include a signal/leader sequence, such as a Japanese encephalitis virus (JEV) signal/leader sequence (SEQ ID NO: 14). The polypeptides can also be isolated from other components (e.g., components with which the polypeptides are natively associated) and incorporated into compositions of the invention.

By "portion" or "fragment" is meant a part of a whole. A portion can comprise at least 10%, 20%, 30%, 40%, 50%, 60%, 70%, 80%, 90%, or 95% of the entire length of a polynucleotide or polypeptide sequence region. For polynucleotides, for example, a portion can include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800 or more contiguous nucleotides of a reference polynucleotide molecule. For polypeptides, for example, a portion can include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, 325, 350, 375, 400, 425, 450, 475, 500, 525, 550, 575, or 600 or more continuous amino acids of a reference polypeptide molecule.

In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, 1400, 1500, 1600, 1700 or more consecutive nucleotides of the polynucleotide M-Env (SEQ ID NO: 1). In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, 1400, 1500, or more consecutive nucleotides of the polynucleotide prM-Env.dTM (SEQ ID NO: 3). In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, 1400, or more consecutive nucleotides of the polynucleotide prM-Env.dStem (SEQ ID NO: 5). In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, 1400, 1500, or more consecutive nucleotides of the polynucleotide Env (SEQ ID NO: 7). In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, or more consecutive nucleotides of the polynucleotide Env.dTM (SEQ ID NO: 9). In some instances, a fragment of a nucleic acid molecule can include at least 20, 30, 40, 50, 60, 70, 80, 90, 100, 200, 300, 400, 500, 600, 700, 800, 900, 1000, 1100, 1200, or more consecutive nucleotides of the polynucleotide Env.dStem (SEQ ID NO: 11). In some instances, a fragment of a nucleic acid molecule can include at least 5, 6, 7, 8, 9, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or more consecutive nucleotides of the polynucleotide prM-Env (full length) (SEQ ID NO: 24). In some instances, a fragment of a nucleic acid molecule can include at least 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or more consecutive nucleotides of the polynucleotide prM-Env with JEV Stem/TM (SEQ ID NO: 26).

In some instances, a fragment of a polypeptide can include at least 20, 25, 50, 75, 90, 100, 125, 150, 175, 200, 225, 250, 275, 300, 325, 350, 375, 400, 425, 450, 475, 500, 525, 550, or more consecutive amino acids of polypeptide M-Env (SEQ ID NO: 2). In some instances, a fragment of a polypeptide can include at least 20, 25, 50, 75, 90, 100, 125, 150, 175, 200, 225, 250, 275, 300, 325, 350, 375, 400, 425, 450, 475, 500, or more consecutive amino acids of polypeptide prM-Env.dTM (SEQ ID NO: 4). In some instances, a fragment of a polypeptide can include at least 20, 25, 50, 75, 90, 100, 125, 150, 175, 200, 225, 250, 275, 300, 325, 350, 375, 400, 425, 450, 475, or more consecutive amino acids of polypeptide prM-Env.dStem (SEQ ID NO: 6). In some instances, a fragment of a polypeptide can include at least 20, 25, 50, 75, 90, 100, 125, 150, 175, 200, 225, 250, 275, 300, 325, 350, 375, 400, 425, 450, 475, 500, or more consecutive amino acids of polypeptide Env (SEQ ID NO: 8). In some instances, a fragment of a polypeptide can include at least 20, 25, 50, 75, 90, 100, 125, 150, 175, 200, 225, 250, 275, 300, 325, 350, 375, 400, 425, or more consecutive amino acids of polypeptide Env.dTM (SEQ ID NO: 10). In some instances, a fragment of a polypeptide can include at least 20, 25, 50, 75, 90, 100, 125, 150, 175, 200, 225, 250, 275, 300, 325, 350, 375, 400, or more consecutive amino acids of polypeptide Env.dStem (SEQ ID NO: 12). In some instances, a fragment of a polypeptide can include at least 20, 25, 50, 75, 90, 100, 125, 150, 175, 200, 225, 250, 275, 300, 325, 350, 375, 400, 425, 450, 475, 500, 525, 550, 575, 600, 625, 650, 675, or more consecutive amino acids of polypeptide prM-Env (full length) (SEQ ID NO: 25). In some instances, a fragment of a polypeptide can include at least 20, 25, 50, 75, 90, 100, 125, 150, 175, 200, 225, 250, 275, 300, 325, 350, 375, 400, 425, 450, 475, 500, 525, 550, 575, 600, 625, 650, 675, or more consecutive amino acids of polypeptide prM-Env with JEV Stem/TM (SEQ ID NO: 27).

In some instances, administration of a fragment of a polynucleotide (e,g., SEQ ID NOs: 1, 3, 5, 7, 9, 11, 24, and/or 26) and/or a polypeptide (e.g., SEQ ID NOs: 2, 4, 6, 8, 10, 12, 25, and/or 27) of the invention to a subject can illicit an immune response in the subject.

The invention also features recombinant vectors including any one or more of the polynucleotides described above. The vectors of the invention can be used to deliver a nucleic acid expressing an immunogen of the invention (e.g., one of more of SEQ ID NOs: 2, 4, 6, 8, 10, or 12 or variants thereof, having at least 85-99% sequence identity thereto, for example at least greater than 90% sequence identity thereto), and include mammalian, viral, and bacterial expression vectors. The mammalian, viral, and bacterial vectors of the invention can be genetically modified to contain one or more nucleic acid sequences set forth in SEQ ID NOs: 1, 3, 5, 7, 9, or 11 or variants thereof, having at least 85-99% sequence identity thereto, for example at least greater than 90% sequence identity thereto, and complements thereof.

Promoters and other expression regulation signals can be selected to be compatible with the host cell for which expression is designed. For example, mammalian promoters include the metallothionein promoter, which can be induced in response to heavy metals, such as cadmium, and the β-actin promoter. A viral promoter, which can be obtained from the genome of a virus, such as, for example, polyoma virus, fowlpox virus, adenovirus (A), bovine papilloma virus, avian sarcoma virus, cytomegalovirus (CMV), a retrovirus, hepatitis-B virus, and Simian Virus 40 (SV40), and human papillomavirus (HPV), can also be used. These promoters are well known and readily available in the art.

A preferred promoter element is the CMV immediate early promoter. In some embodiments, the expression plasmid is pcDNA3.1+(Invitrogen, CA, USA). In some embodiments, the expression vector is a viral vector, such as a vector derived from adenovirus or poxvirus.

Viral genomes provide a rich source of vectors that can be used for the efficient delivery of exogenous genes into the genome of a cell (e.g., a eukaryotic or prokaryotic cell). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors that can be used to deliver a nucleic acid expressing an immunogen of the invention (e.g., one of more of SEQ ID NOs: 2, 4, 6, 8, 10, or 12 or variants thereof having at least 85-99% sequence identity thereto, for example at least greater than 90% sequence identity thereto) include adenovirus (e.g., Ad2, Ad5, Ad11, Ad12, Ad24, Ad26, Ad34, Ad35, Ad40, Ad48, Ad49, Ad50, Ad52 (e.g., RhAd52), and Pan9 (also known as AdC68)). These adenovirus vectors can be derived from, for example, human, chimpanzee (e.g., ChAd1, ChAd3, ChAd7, ChAd8, ChAd21, ChAd22, ChAd23, ChAd24, ChAd25, ChAd26, ChAd27.1, ChAd28.1, ChAd29, ChAd30, ChAd31.1, ChAd32, ChAd33, ChAd34, ChAd35.1, ChAd36, ChAd37.2, ChAd39, ChAd40.1, ChAd41.1, ChAd42.1, ChAd43, ChAd44, ChAd45, ChAd46, ChAd48, ChAd49, ChAd49, ChAd50, ChAd67, or SA7P), or rhesus adenoviruses. The viral vector can be used to infect cells of a subject, which, in turn, promotes the translation of the heterologous gene(s) of the viral vector into the immunogens of the invention. For example, a viral vector of the invention can be genetically modified to contain one or more nucleic acid sequences set forth in SEQ ID NOs: 1, 3, 5, 7, 9, or 11 or variants thereof having at least 85-99% sequence identity thereto, for example at least greater than 90% sequence identity thereto, and complements thereof.

Adenoviral vectors disclosed in International Patent Application Publications WO2006/040330 and WO2007/104792, each incorporated by reference herein, are particularly useful as vectors of the invention. These adenoviral vectors can encode and/or deliver one or more of the immunogens of the invention (e.g., ZIKV polypeptides) to treat a subject having a pathological condition associated with a viral infection (e.g., a ZIKV infection). In some embodiments, one or more recombinant adenovirus vectors can be administered to the subject in order to express more than one type of immunogen (e.g., ZIKV polypeptide) of the invention.

Adenoviruses

An adenovirus according to the invention belongs to the family of the Adenoviridae and preferably is one that belongs to the genus *Mastadenovirus*. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 or 35.

An advantage of these serotypes is a low seroprevalence and/or low pre-existing neutralizing antibody titers in the human population. Preparation of rAd26 vectors is described, for example, in WO 2007/104792 and in Abbink et al., (2007) Virol 81(9):4654-63, both of which are incorporated by reference herein in their entirety. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) J Virol 77(15): 8263-71, all of which are incorporated by reference herein in their entirety. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, J Virol 75: 11603-13; Cohen et al, 2002, J Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vector rAd26

In a preferred embodiment according to the invention the adenoviral vectors comprise capsid proteins from two rare serotypes: Ad26 or Ad35. In the typical embodiment, the vector is an rAd26 virus.

Thus, the vectors that can be used in the invention comprise an Ad26 capsid protein (e.g., a fiber, penton or hexon protein). One of skill will recognize that it is not necessary that an entire Ad26 capsid protein be used in the vectors of the invention. Thus, chimeric capsid proteins that include at least a part of an Ad26 capsid protein can be used in the vectors of the invention. The vectors of the invention can also comprise capsid proteins in which the fiber, penton, and hexon proteins are each derived from a different serotype, so long as at least one capsid protein is derived from Ad26. In preferred embodiments, the fiber, penton and hexon proteins are each derived from Ad26.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention can combine the absence of pre-existing immunity of the Ad26 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 (i.e., the vector is rAd26). In some embodiments, the adenovirus is replication deficient, e.g. because it contains a deletion in the E1 region of the genome. For the adenoviruses of the invention, being derived from Ad26, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032). The preparation of recombinant adenoviral vectors is well known in the art.

Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the invention, the vectors useful for the invention include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful in the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention can contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

Pharmaceutical Compositions

In another general aspect, the invention relates to pharmaceutical compositions comprising adenoviral vectors (or adenoviral particles) comprising a nucleic acid molecule encoding a Zika virus antigen of the invention and a pharmaceutically acceptable carrier. Adenoviral vectors (or particles) of the invention and compositions comprising them are also useful in the manufacture of a medicament for therapeutic applications mentioned herein.

By "pharmaceutical composition" is meant any composition that contains a therapeutically or biologically active agent, such as an immunogenic composition or vaccine of the invention (e.g., an adenoviral particle comprising a ZIKV nucleic acid molecule and/or polypeptide of the invention), preferably including a nucleotide sequence encoding an antigenic gene product of interest, or fragment thereof, that is suitable for administration to a subject and that treats or prevents a disease (e.g., ZIKV infection) or reduces or ameliorates one or more symptoms of the disease (e.g., ZIKV viral titer, viral spread, infection, and/or cell fusion)). For the purposes of this invention, pharmaceutical compositions include vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* (21$^{st}$ ed.), ed. A. R. Gennaro, Lippincott Williams & Wilkins, 2005, and Encyclopedia of Pharmaceutical Technology, ed. J. Swarbrick, Informa Healthcare, 2006, each of which is hereby incorporated by reference.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical compositions are provided comprising the adenoviral vectors of the invention in an amount from about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, about $1 \times 10^{11}$, about $2 \times 10^{11}$, about $3 \times 10^{11}$, about $4 \times 10^{11}$, or about $5 \times 10^{11}$ viral vectors (or particles) per dose. In certain embodiments of the invention, the pharmaceutical composition comprises about $1 \times 10^{10}$ adenoviral vectors (or particles) to about $5 \times 10^{11}$ adenoviral vectors (or particles) per dose. In certain embodiments of the invention, the pharmaceutical composition comprises about $5 \times 10^{10}$ adenoviral vectors (or particles) to about $1 \times 10^{11}$ adenoviral vectors (or particles) per dose. In certain embodiments of the invention, the pharmaceutical composition comprises about $5 \times 10^{10}$ adenoviral vectors (or particles) per dose. In certain embodiments of the invention, the pharmaceutical composition comprises about $1 \times 10^{11}$ adenoviral vectors (or particles) per dose.

The pharmaceutical composition can have a pH from about 3.0 to about 10, for example from about 3 to about 7, or from about 5 to about 9. The formulation can further comprise at least one ingredient selected from the group consisting of a buffer system, preservative(s), tonicity agent(s), chelating agent(s), stabilizer(s) and surfactant(s).

In certain embodiments, the subject is administered a single dose of the pharmaceutical composition. In certain embodiments, the subject is administered a double dose of the pharmaceutical composition. When administering a double dose, the first and second dose of the pharmaceutical composition can be administered to the subject about four weeks, about eight weeks, about twelve weeks, about three months, about six months, about nine months, about one year, or about two years apart.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via a syringe or an infusion pump. The injection can be delivered subcutaneously, intramuscularly, intraperitoneally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they may be delayed release, sustained release, or modified release, in which case they may comprise water-insoluble polymers that regulate the rate of dissolution of the dosage form in the gastrointestinal tract.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA (ethylenediamine tetraacetic acid), and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention can comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid can be present either in its free base form or in its salt form. Any stereoisomer (i.e., L, D, or a mixture thereof) of the amino acid base may be present. The amino acid base can be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

It is also apparent to one skilled in the art that the therapeutically effective dose for adenoviral particles comprising a nucleic acid molecule encoding a Zika virus antigen of the present invention or a pharmaceutical composition thereof will vary according to the desired effect. Therefore, optimal dosages to be administered can be readily determined by one skilled in the art and will vary with the particular adenoviral particle used, the mode of administration, the strength of the preparation, and the advancement of the disease condition (e.g., Zika virus infection). In addition, factors associated with the particular subject being treated, including subject age, weight, diet and time of administration, will result in the need to adjust the dose to an appropriate therapeutic level.

The pharmaceutically-acceptable salts of the adenoviral particles of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention can be administered by any means that accomplish their intended purpose. As used herein, by "administering" is meant a method of giving a dosage of a pharmaceutical composition (e.g., an immunogenic composition (e.g., a vaccine (e.g., a Zika virus (ZIKV) vaccine))) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

Methods of Use

The present invention provides methods for generating an immune response against a Zika virus in a human subject in need thereof. The methods comprise administering to the subject a pharmaceutical composition comprising adenoviral vectors comprising a nucleic acid sequence encoding a Zika virus antigen and a pharmaceutically acceptable carrier. The methods are for preventing, treating, delaying the onset of, or ameliorating a Zika virus infection or any one or more symptoms of said Zika virus infection, the method comprising administering to the subject in need thereof an effective amount of a pharmaceutical composition of the invention.

According to particular embodiments, an immunogenic or effective or protective amount refers to the amount of an immunogen which is sufficient to achieve one, two, three, four, or more of the following effects: (i) reduce or ameliorate the severity of the Zika virus infection to be treated or a symptom associated therewith; (ii) reduce the duration of the Zika virus infection to be treated, or a symptom associated therewith; (iii) prevent the progression of the Zika virus infection to be treated, or a symptom associated therewith; (iv) cause regression of the Zika virus infection to be treated, or a symptom associated therewith; (v) prevent the development or onset of the Zika virus infection to be treated, or a symptom associated therewith; (vi) prevent the recurrence of the Zika virus infection to be treated, or a symptom associated therewith; (vii) reduce hospitalization of a subject having the Zika virus infection or condition to be treated, or a symptom associated therewith; (viii) reduce hospitalization length of a subject having the Zika virus infection to be treated, or a symptom associated therewith; (ix) increase the survival of a subject with the Zika virus infection to be treated, or a symptom associated therewith; (xi) inhibit or reduce the Zika virus infection to be treated, or a symptom associated therewith in a subject; and/or (xii) enhance or improve the prophylactic or therapeutic effect(s) of another therapy; (xiii) prevent transmission of zika virus through sexual and maternal to fetal routes; (xiv) prevent and/or reduces the severity of fetal brain abnormalities associated with Zika virus.

Examples of symptoms of diseases caused by a viral infection, such as ZIKV, that can be prevented using the compositions of the invention include, for example, fever, joint pain, rash, conjunctivitis, muscle pain, headache, retro-orbital pain, edema, lymphadenopathy, malaise, asthenia, sore throat, cough, nausea, vomiting, diarrhea, and hematospermia. These symptoms, and their resolution during treatment, can be measured by, for example, a physician during a physical examination or by other tests and methods known in the art.

The immunogenic or effective amount or dosage can vary according to various factors, such as the Zika virus infection to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related to the Zika virus infection, which is not necessarily discernible in the subject, but can be discernible in the subject. The terms "treat," "treating," and "treatment," can also refer to causing regression, preventing the progression, or at least slowing down the progression of the Zika virus infection. In a particular embodiment, "treat," "treating," and "treatment" refer to an alleviation, prevention of the development or onset, or reduction in the duration of one or more symptoms associated with the Zika virus infection. In a particular embodiment, "treat," "treating," and "treatment" refer to prevention of the recurrence of the Zika virus infection. In a particular embodiment, "treat," "treating," and "treatment" refer to an increase in the survival of a subject having the Zika virus infection. In a particular embodiment, "treat," "treating," and "treatment" refer to elimination of the Zika virus infection in the subject.

In certain embodiments, administration of an immunogenic or effective amount of a pharmaceutical composition of the invention reduces ZIKV serum viral loads determined from a subject having a ZIKV infection by at least about 5%, 10%, 20%, 30%, 40%, 50%, 60%, 70%, 80%, 90%, or more compared to viral loads determined from the subject prior to administration of an effective amount of a composition of the invention. In some instances, administration of an effective amount of a composition of the invention reduces serum viral loads to an undetectable level compared to viral loads determined from the subject prior to administration of an effective amount of a composition of the invention. In some instances, administration of an effective amount of a composition of the invention results in a reduced and/or undetectable serum viral load that may be maintained for at least about 1, 2, 3, 4, 5, 6, 7 days; 1, 2, 3, 4, weeks; 1, 2, 3, 4, 5, 6, 7, 8, 9, 10, 11, or 12 months; or 1 year or more.

In addition, single or multiple administrations of the compositions of the present invention can be given (pre- or post-exposure and/or pre- or post-diagnosis) to a subject (e.g., one administration or administration two or more times). For example, subjects who are particularly susceptible to, for example, viral infection (e.g., a ZIKV infection) can require multiple administrations of the compositions of the present invention to establish and/or maintain protection against the virus. Levels of induced immunity provided by the pharmaceutical compositions described herein can be monitored by, for example, measuring amounts of neutralizing secretory and serum antibodies. The dosages can then be adjusted or repeated as necessary to trigger the desired level of immune response. For example, the immune response triggered by a single administration (prime) of a composition of the invention may not sufficiently potent and/or persistent to provide effective protection. Accordingly, in some embodiments, repeated administration (boost), such that a prime boost regimen is established, can significantly enhance humoral and cellular responses to the antigen of the composition.

Alternatively, the efficacy of treatment can be determined by monitoring the level of the antigenic or therapeutic gene product, or fragment thereof, expressed in a subject (e.g., a human) following administration of the pharmaceutical compositions of the invention. For example, the blood or lymph of a subject can be tested for antigenic or therapeutic gene product, or fragment thereof, using, for example, standard assays known in the art.

In some instances, efficacy of treatment can be determined by monitoring a change in the serum viral load from a sample from the subject obtained prior to and after administration of an effective amount of a pharmaceutical composition of the invention. A reduction in serum viral load of at least about 5%, 10%, 20%, 30%, 40%, 50%, 60%, 70%, 80%, 90%, or more compared to viral load determined from the subject prior to administration of an effective amount of a composition of the invention can indicate that the subject is receiving benefit from the treatment. If a viral load does not decrease by at least about 10%, 20%, 30%, or more after administration of a composition of the invention, the dosage of the composition to be administered can be increased. For example, by increasing the number of viral particles (VP) of an adenovirus vector-based vaccine.

Immunogenicity of the pharmaceutical compositions of the invention can be improved if it is co-administered with an immunostimulatory agent and/or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

The term "immunostimulatory agent" refers to substances (e.g., drugs and nutrients) that stimulate the immune system by inducing activation or increasing activity of any of its components. An immunostimulatory agent can, for example, include a cytokine (e.g., the granulocyte macrophage colony-stimulating factor) and interferon (e.g., IFN-α and/or IFN-γ).

The term "adjuvant" is defined as a pharmacological or immunological agent that modifies the effect of other agents (e.g., a ZIKV antigen) while having few if any direct effects when administered alone. An adjuvant can be one or more substances that cause stimulation of the immune system. In this context, an adjuvant is used to enhance an immune response to the adenoviral particles of the invention.

EMBODIMENTS

The invention provides also the following non-limiting embodiments.

Embodiment 1 is a method for generating an immune response against a Zika virus in a human subject in need thereof, the method comprising administering to the subject a pharmaceutical composition comprising adenoviral vectors comprising a nucleic acid sequence encoding a Zika virus antigen and a pharmaceutically acceptable carrier, wherein about $5\times10^{10}$ adenoviral vectors (or particles) to about $1\times10^{11}$ adenoviral vectors (or particles) are administered per dose to the subject in need thereof.

Embodiment 2 is the method of embodiment 1, for generating a protective immune response against a Zika virus in a human subject in need thereof.

Embodiment 3 is the method of embodiment 1 or 2, wherein the pharmaceutical composition is administered via an intramuscular injection to the human subject in need thereof.

Embodiment 4 is the method of any one of embodiments 1-3, wherein the pharmaceutical composition is administered to the human subject as a single dose.

Embodiment 5 is the method of any one of embodiments 1-3, wherein the pharmaceutical composition is administered to the human subject as a double dose.

Embodiment 6 is the method of embodiment 5, wherein the first and second dose of the pharmaceutical composition are administered to the human subject about four weeks, about eight weeks, about twelve weeks, about three months, about six months, about nine months, about one year, or about two years apart.

Embodiment 7 is the method of embodiment 5, wherein the first and second dose of the pharmaceutical composition are administered to the human subject about eight weeks apart.

Embodiment 8 is the method of any one of embodiments 1-7, wherein about $5\times10^{10}$, about $6\times10^{10}$, about $7\times10^{10}$, about $8\times10^{10}$, about $9\times10^{10}$, or about $1\times10^{11}$ of the adenoviral vectors (or particles) are administered to the human subject in need thereof.

Embodiment 9 is the method of embodiment 8, wherein about $5\times10^{10}$ adenoviral vectors (or particles) are administered to the human subject in need thereof.

Embodiment 10 is the method of embodiment 8, wherein about $1\times10^{11}$ adenoviral vectors (or particles) are administered to the human subject in need thereof.

Embodiment 11 is the method of any one of embodiments 1-10, wherein the Zika virus antigen comprises the amino acid sequence of SEQ ID NO:2, 4, 6, 8, 10, or 12.

Embodiment 12 is the method of embodiment 11, wherein the Zika virus antigen comprises the amino acid sequence of SEQ ID NO:2.

Embodiment 13 is the method of embodiment 11, wherein the Zika virus antigen comprises the amino acid sequence of SEQ ID NO:4.

Embodiment 14 is the method of embodiment 11, wherein the Zika virus antigen comprises the amino acid sequence of SEQ ID NO:6.

Embodiment 15 is the method of embodiment 11, wherein the Zika virus antigen comprises the amino acid sequence of SEQ ID NO:8.

Embodiment 16 is the method of embodiment 11, wherein the Zika virus antigen comprises the amino acid sequence of SEQ ID NO:10.

Embodiment 17 is the method of embodiment 11, wherein the Zika virus antigen comprises the amino acid sequence of SEQ ID NO:12.

Embodiment 18 is the method of any one of embodiments 1-17, wherein the adenoviral vector serotype is selected from the group consisting of Ad2, Ad5, Ad11, Ad12, Ad24, Ad26, Ad34, Ad35, Ad40, Ad48, Ad49, Ad50, Ad52, and Pan9.

Embodiment 19 is the method of embodiment 18, wherein the adenoviral vector serotype is the Ad26 serotype.

Embodiment 20 is a method for preventing a Zika virus infection or the progression of a Zika virus infection in a human subject in need thereof, the method comprising administering to the subject a pharmaceutical composition comprising adenoviral vectors comprising a nucleic acid sequence encoding a Zika virus antigen and a pharmaceutically acceptable carrier, wherein the pharmaceutical composition comprises a total dosage of about $5\times10^{10}$ adenoviral vectors (or particles) to about $1\times10^{11}$ adenoviral vectors (or particles) per administration.

Embodiment 21 is the method of embodiment 20, wherein the pharmaceutical composition is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion, by catheter, by lavage, or by gavage.

Embodiment 22 is the method of embodiment 21, wherein the pharmaceutical composition is administered in an intramuscular injection.

Embodiment 23 is the method of any one of embodiments 20-22, wherein the pharmaceutical composition is administered as a single dose.

Embodiment 24 is the method of any one of embodiments 20-22, wherein the pharmaceutical composition is administered as a double dose.

Embodiment 25 is the method of embodiment 24, wherein the first and second dose of the pharmaceutical composition are administered to the human subject about four weeks, about eight weeks, about twelve weeks, about three months, about six months, about nine months, about one year, or about two years apart.

Embodiment 26 is the method of embodiment 25, wherein the first and second dose of the pharmaceutical composition are administered to the human subject about eight weeks apart.

Embodiment 27 is the method of any one of the embodiments 20-26, wherein about $5\times10^{10}$, about $6\times10^{10}$, about $7\times10^{10}$, about $8\times10^{10}$, about $9\times10^{10}$, or about $1\times10^{11}$ adenoviral vectors (or particles) are administered to the human subject in need thereof.

Embodiment 28 is the method of embodiment 27, wherein about $5\times10^{10}$ adenoviral vectors (or particles) are administered to the human subject in need thereof.

Embodiment 29 is the method of embodiment 27, wherein about $1\times10^{11}$ adenoviral vectors (or particles) are administered to the human subject in need thereof.

Embodiment 30 is the method of any one of embodiments 20-29, wherein the Zika virus antigen comprises the amino acid sequence of SEQ ID NO:2, 4, 6, 8, 10, or 12.

Embodiment 31 is the method of embodiment 30, wherein the Zika virus antigen comprises the amino acid sequence of SEQ ID NO:2.

Embodiment 32 is the method of embodiment 30, wherein the Zika virus antigen comprises the amino acid sequence of SEQ ID NO:4.

Embodiment 33 is the method of embodiment 30, wherein the Zika virus antigen comprises the amino acid sequence of SEQ ID NO:6.

Embodiment 34 is the method of embodiment 30, wherein the Zika virus antigen comprises the amino acid sequence of SEQ ID NO:8.

Embodiment 35 is the method of embodiment 30, wherein the Zika virus antigen comprises the amino acid sequence of SEQ ID NO:10.

Embodiment 36 is the method of embodiment 30, wherein the Zika virus antigen comprises the amino acid sequence of SEQ ID NO:12.

Embodiment 37 is the method of any one of embodiments 20-36, wherein the adenoviral vector serotype is selected from the group consisting of Ad2, Ad5, Ad11, Ad12, Ad24, Ad26, Ad34, Ad35, Ad40, Ad48, Ad49, Ad50, Ad52, and Pan9.

Embodiment 38 is the method of embodiment 37, wherein the adenoviral vector serotype is the Ad26 serotype.

Embodiment 39 is the use of a pharmaceutical composition for the preparation of a vaccine for generating an immune response against a Zika virus in a human subject in need thereof, comprising adenoviral vectors comprising a nucleic acid sequence encoding a Zika virus antigen and a pharmaceutically acceptable carrier, wherein about $5\times10^{10}$ adenoviral vectors (or particles) to about $1\times10^{11}$ adenoviral vectors (or particles) are administered per dose to the subject in need thereof.

Embodiment 40 is the use of embodiment 39, wherein the vaccine is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion, by catheter, by lavage, or by gavage.

Embodiment 41 is the use of embodiment 40, wherein the vaccine is administered in an intramuscular injection.

Embodiment 42 is the use of any one of embodiments 39-41, wherein the vaccine is administered as a single dose.

Embodiment 43 is the use of any one of embodiments 39-41, wherein the vaccine is administered as a double dose.

Embodiment 44 is the use of embodiment 43, wherein the first and second dose of the vaccine are administered to the human subject about four weeks, about eight weeks, about twelve weeks, about three months, about six months, about nine months, about one year, or about two years apart.

Embodiment 45 is the use of embodiment 44, wherein the first and second dose of the vaccine are administered to the human subject about eight weeks apart.

Embodiment 46 is the use of any one of the embodiments 39-45, wherein about $5\times10^{10}$, about $6\times10^{10}$, about $7\times10^{10}$, about $8\times10^{10}$, about $9\times10^{10}$, or about $1\times10^{11}$ adenoviral vectors (or particles) are administered to the human subject in need thereof.

Embodiment 47 is the use of embodiment 46, wherein about $5\times10^{10}$ adenoviral vectors (or particles) are administered to the human subject in need thereof.

Embodiment 48 is the use of embodiment 46, wherein about $1\times10^{11}$ adenoviral vectors (or particles) are administered to the human subject in need thereof.

Embodiment 49 is the use of any one of embodiments 39-48, wherein the Zika virus antigen comprises the amino acid sequence of SEQ ID NO:2, 4, 6, 8, 10, or 12.

Embodiment 50 is the use of embodiment 49, wherein the Zika virus antigen comprises the amino acid sequence of SEQ ID NO:2.

Embodiment 51 is the use of embodiment 49, wherein the Zika virus antigen comprises the amino acid sequence of SEQ ID NO:4.

Embodiment 52 is the use of embodiment 49, wherein the Zika virus antigen comprises the amino acid sequence of SEQ ID NO:6.

Embodiment 53 is the use of embodiment 49, wherein the Zika virus antigen comprises the amino acid sequence of SEQ ID NO:8.

Embodiment 54 is the use of embodiment 49, wherein the Zika virus antigen comprises the amino acid sequence of SEQ ID NO:10.

Embodiment 55 is the use of embodiment 49, wherein the Zika virus antigen comprises the amino acid sequence of SEQ ID NO:12.

Embodiment 56 is the use of any one of embodiments 39-55, wherein the adenoviral vector serotype is selected from the group consisting of Ad2, Ad5, Ad11, Ad12, Ad24, Ad26, Ad34, Ad35, Ad40, Ad48, Ad49, Ad50, Ad52, and Pan9.

Embodiment 57 is the use of embodiment 56, wherein the adenoviral vector serotype is the Ad26 serotype.

EXAMPLES

Example 1: Clinical Study to Evaluate Safety, Tolerability, and Immunogenicity of Intramuscularly Administered Adenoviral Particles Comprising a Zika Virus Antigen A clinical study was conducted for evaluating the safety, tolerability and immunogenicity of Ad26.ZIKV.001 vectors at a dose of $5 \times 10^{10}$ viral particles (vp) or $1 \times 10^{11}$ vp, which were administered intramuscularly as single dose or in a two dose schedule in healthy adults.

The study was a randomized, placebo-controlled, double-blind first in human phase 1 study conducted in 100 healthy adult male and female subjects (≥18 to ≤50 years of age). The study consists of a vaccination period in which subjects were administered the Ad26.ZIKV.001 vaccine at either a $5 \times 10^{10}$ vp or $1 \times 10^{11}$ vp dose at baseline (Day 1) followed by a second administration on Day 57 of either a placebo or the Ad26.ZIKV.001 vaccine at a similar dose as the first administration.

Subjects were enrolled into 5 different groups of 20 healthy subjects each. Overall, subjects were randomized in parallel in 1:1:1:1:1 ratio to 1 of 5 vaccination groups to receive active vaccine or placebo (0.9% saline) through intramuscular (IM) injections (0.5 ml) as follows:

Group 1: Ad26.ZIKV.001 ($5 \times 10^{10}$ vp) on Day 1, followed by a second administration of Ad26.ZIKV.001 ($5 \times 10^{10}$ vp) on Day 57, or Group 2: Ad26.ZIKV.001 ($5 \times 10^{10}$ vp) on Day 1, followed by a Placebo on Day 57.

Group 3: Ad26.ZIKV.001 ($1 \times 10^{11}$ vp) on Day 1, followed by a second administration of Ad26.ZIKV.001 ($1 \times 10^{11}$ vp) on Day 57, or Group 4: Ad26.ZIKV.001 ($1 \times 10^{11}$ vp) on Day 1, followed by a Placebo on Day 57.

Group 5: Placebo on Day 1, followed by a Placebo on Day 57.

The exemplary study vaccination schedules are summarized in Table 1.

TABLE 1

Study Vaccination Schedules

| Group | Immunization 1 (Dose 1) | Immunization 2 (Dose 2) | Immunization Schedule (Weeks) | Group Size N |
|---|---|---|---|---|
| 1 | Ad26.ZIKV.001 ($5 \times 10^{10}$ vp) | Ad26.ZIKV.001 ($5 \times 10^{10}$ vp) | 0-8 | 20 |
| 2 | Ad26.ZIKV.001 ($5 \times 10^{10}$ vp) | Placebo | 0-8 | 20 |
| 3 | Ad26.ZIKV.001 ($1 \times 10^{11}$ vp) | Ad26.ZIKV.001 ($1 \times 10^{11}$ vp) | 0-8 | 20 |
| 4 | Ad26.ZIKV.001 ($1 \times 10^{11}$ vp) | Placebo | 0-8 | 20 |
| 5 | Placebo | Placebo | 0-8 | 20 |

Abbreviations:
vp: viral particles;
N: number of subjects to receive study vaccine Vaccine Material Ad26.ZIKV.001 is a monovalent vaccine composed of a recombinant, replication-incompetent adenovirus serotype 26 (Ad26) vector, constructed to encode the Zika virus (ZIKV) membrane (M) and envelope (Env) proteins (M-Env) (SEQ ID NO:2) derived from the ZIKV strain from Brazil (ZIKV-BR) BeH815744 strain.

Safety Endpoint

Safety was assessed by a collection of solicited local and systemic adverse events, unsolicited adverse events, serious adverse events, and immediately reportable events. Other safety assessments included clinical laboratory tests (hematology, biochemistry), vital signs measurements (heart rate, supine systolic and diastolic blood pressure, body temperature), and physical examinations at multiple time points.

Immunogenicity Endpoints

Blood samples for immunogenicity assessments (humoral and cellular immune responses) were collected at different time points. Blood samples (serum) for assessment of humoral immune responses were obtained from all subjects. Blood samples (PBMC) for assessment of cellular immune responses were obtained from a subset of subjects only.

Humoral and cellular immunogenicity assays can include, but are not limited to, the assays summarized in Tables 2 and 3.

TABLE 2

Summary of Humoral Immunogenicity Assays

| Assay | Purpose |
|---|---|
| Secondary endpoints | |
| ZIKV neutralization (VNA) | Analysis of neutralizing antibodies to the vaccine strain (or other strain) |
| Exploratory endpoints | |
| ZIKV antibody (ELISA) | Analysis of antibodies binding to ZIKV, or individual ZIKV proteins (e.g., Env-protein, M-protein) |
| ZIKV neutralization (neutralization assay) | Analysis of neutralizing antibodies to vaccine strain (or other strain), as measured by an alternative neutralization assay (different from the VNA used for the secondary endpoint) |
| Flavivirus neutralization (VNA) | Analysis of neutralizing antibodies to flaviviruses other than ZIKV, such as YFV, JEV, WNV, DENV, and TBEV |

ELISA: enzyme-linked immunosorbent assay

TABLE 3

Summary of Cellular Immunogenicity Assays

| Assay | Purpose |
|---|---|
| Exploratory endpoints | |
| Flow cytometry (ICS) | Analysis of T-cell responses to ZIKV M-, Env-, and/or other protein peptides (including, but not limited to CD4+/CD8+, IL2, IFNγ, TNFα, other markers determining functionality, memory differentiation, activation or T-helper [Th]1/Th2 status) |
| IFNγ ELISpot | T-cell IFNγ responses to ZIKV M-, Env-, and/or other ZIKV protein peptides, or adenoviral protein peptide |

ELISpot: enzyme-linked immunspot;
ICS: intracellular cytokine staining;
IFN: interferon;
IL: interleukin;
TNF: tumor necrosis factor Immunogenicity was assessed in a subset of 75 subjects at baseline (Day 1), at 14 days and 28 days after the first vaccination (Days 15 and 29), at the day of the boost vaccination (pre-dose, D57), and 14 days and 28 days after the boost vaccination (D71 and 85) using a virus neutralization assay (VNA) to analyze the neutralizing antibody response against ZIKV (Zika Microneutralization Assay (MN50)). This in vitro assay determines the capacity of vaccine-induced antibodies to prevent infection of a cell line by live ZIKV (Modjarrad et al., The Lancet, Vol. 391, issue 10120, 10-16 Feb. 2018, p. 563-571). Results from the remaining 25 subjects, from any other immunological assessment measuring response against ZIKV, or from further time points in the ongoing study were not yet available.

The actual values, geometric mean titers (GMT) and percentage of responders are shown in FIGS. 1A and B (Zika Microneutralization Assay (MN50). Table 4 shows the GMTs, the percentage of subjects with MN50 titers above 10 (lower limit of quantification of the MN50 VNA and assay positivity criterium) and 100 MN50 units, respectively, and the geometric fold increase for the Zika microneutralization assay. Titers above 100 MN50 units have been associated with protection against ZIKV challenge in mouse and NHP models (Modjarrad et al., The Lancet, Vol. 391, issue 10120, 10-16 Feb. 2018, p. 563-571; Abbink et al., Science, 9 Sep. 2016, Vol. 353, Issue 6304, pp. 1129-1132; Abbink et al., Sci Transl Med. 2017, Dec. 13, 9(420)).

At baseline all subjects had a geometric mean titer below LLOQ. None of the placebo recipients developed Zika MN50 titers above the LLOQ of 10 at any time point post vaccination. Fifteen days post dose 1, a majority of vaccinated subjects developed ZIKV neutralizing antibody titers, irrespective of the dose given, and geometric mean titers increased to levels above 100 MN50 units in all groups by day 28. Specifically, geometric mean titers at Day 15 after the first vaccination were 58.8 and 29.8 respectively for the groups receiving Ad26.ZIKV.001 at $5 \times 10^{10}$ viral particles (vp), resulting in a seroconversion rate (i.e. subjects with MN50 titers ≥10) of 80% (12/15) and 53% (8/15), and 53.5 and 52.9 for the groups that received Ad26.ZIKV.001 at $1 \times 10^{11}$ vp, resulting in a seroconversion rate of 78.6% (11/14) and 66.7% (10/15), respectively. Geometric mean titers at Day 29 after the first vaccination increased to 121.4 and 139.4 respectively for the groups receiving Ad26.ZIKV.001 at $5 \times 10^{10}$ vp, resulting in seroconversion rates of 93.3% (14/15) and 86.7% (13/15), and 125 and 169 for the groups that received Ad26.ZIKV.001 at $1 \times 10^{11}$ vp, resulting in seroconversion rates of 92.2% (13/14) for both groups. The percentage of subjects whose MN50 titers exceeded 100—a level that showed protection against ZIKV challenge in mouse and NHP models—increased from 36.7% (11/30) on day 15 to 56.7% (17/30) on day 28 in the combined groups receiving $5 \times 10^{10}$ vp of Ad26.ZIKV.001. In the combined groups that received Ad26.ZIKV.001 at $1 \times 10^{11}$ vp, 13/29 (46.7%) and 16/28 (58.6%) subjects reached MN50 titers of ≥100 at 14 days and 28 days after prime vaccination, respectively.

Geometric mean titers at Day 57, prior to the second dose of either vaccine or placebo, were 37.5 and 64.9 respectively for the groups receiving $5 \times 10^{10}$ vp of Ad26.ZIKV.001 and slightly higher, 127 and 120.3, for the groups that received $1 \times 10^{11}$ vp of Ad26.ZIKV.001 as prime. In the group that received placebo after prime with $5 \times 10^{10}$ vp of Ad26.ZIKV.001, geometric mean titers remained at 64.2, 14 days after the second vaccination (day 71) and decreased slightly further to 44.8, 28 days after the second vaccination (day 85).

In the group that received a boost of $5 \times 10^{10}$ vp of Ad26.ZIKV.001 on day 57, however, geometric mean MN50 titers increased almost 200-fold to 1980.3 on day 71 and remained at 1284 on day 85, demonstrating a strong boost effect.

In the group that received placebo after prime with $1 \times 10^{11}$ vp of Ad26.ZIKV.001, geometric mean titers remained at 173.2 and 142.4 on day 71 and 85, respectively, while they substantially increased to 1016.8 and 1131 on days 71 and 85, respectively, in the group that received $1 \times 10^{11}$ vp of Ad26.ZIKV.001 as boost, again demonstrating a strong boost effect. All subjects receiving Ad26.ZIKV.001 at two doses, irrespective of the dose, developed MN50 titers ≥10 at both time points, resulting in a 100% seroconversion rate. In addition, 100% (14/14) in the group that received two vaccinations of Ad26.ZIKV.001 at $5 \times 10^{10}$ vp and 92.3% (12/13) in the group that received two vaccinations of Ad26.ZIKV.001 at $1 \times 10^{11}$ vp developed MN50 titers ≥100—the threshold associated with protection against ZIKV challenge in animal models—at 28 days after the second vaccination. In contrast, in the groups that received placebo after the first vaccination of Ad26.ZIKV.001 at $5 \times 10^{10}$ vp or at $1 \times 10^{11}$ vp the percentage of subjects whose MN50 titers reached this threshold was 20% (3/15) and 61.5% (8/13) (at 28 days after the second vaccination, respectively.

In summary, the results show that a robust humoral response was induced within 4 weeks after priming with Ad26.ZIKV.001, and that a second dose of Ad26.ZIKV.001 administered eight weeks after priming was able to boost these responses to substantial levels.

TABLE 4

Zika Microneutralization Assay (MN50): Actual Values, Fold Increases from Baseline and Percentage of Responders over Time; Per Protocol Immunogenicity Population (Study VAC26911ZIK1001)

| | Ad26.ZIKV.001 LD/LD | Ad26.ZIKV.001 LD/PL | Ad26.ZIKV.001 HD/HD | Ad26.ZIKV.001 HD/PL | Placebo |
|---|---|---|---|---|---|
| ZIKV MN50 titer | | | | | |
| Baseline | | | | | |
| N | 15 | 15 | 14 | 15 | 14 |
| Geometric mean | 5 (5; 5) | 5 (5; 5) | 5 (5; 5) | 5 (5; 5) | 5 (5; 5) |
| (95% CI) | | | | | |
| MN50 >= 10 n (%) | 0 | 0 | 0 | 0 | 0 |
| MN50 >= 100 n (%) | 0 | 0 | 0 | 0 | 0 |
| Day 15 | | | | | |
| N | 15 | 15 | 14 | 15 | 14 |
| Geometric mean | 58.8 | 29.8 | 53.5 | 52.9 | 5 (5; 5) |
| (95% CI) | (22.5; 153.7) | (9.6; 92.6) | (17.1; 167.2) | (17.9; 156.2) | |
| Geometric mean fold increase | 6.8 | 4.1 | 6.2 | 6.7 | 1 |
| Responders n (%) | 12 (80.0%) | 8 (53.3%) | 11 (78.6%) | 10 (66.7%) | 0 |
| MN50 >= 10 n (%) | 12 (80.0%) | 8 (53.3%) | 11 (78.6%) | 10 (66.7%) | 0 |
| MN50 >= 100 n (%) | 7 (46.7%) | 4 (26.7%) | 6 (42.9%) | 7 (46.7%) | 0 |
| Day 29 | | | | | |
| N | 15 | 15 | 14 | 14 | 13 |
| Geometric mean | 121.4 | 139.4 | 125 | 169 | 5 (5; 5) |
| (95% CI) | (46.6; 316.6) | (50.1; 388.3) | (53.4; 292.5) | (63.4; 450.7) | |
| Geometric mean fold increase | 12.7 | 15.3 | 13.1 | 17.8 | 1 |
| Responders n (%) | 14 (93.3%) | 13 (86.7%) | 13 (92.9%) | 13 (92.9%) | 0 |
| MN50 >= 10 n (%) | 14 (93.3%) | 13 (86.7%) | 13 (92.9%) | 13 (92.9%) | 0 |
| MN50 >= 100 n (%) | 8 (53.3%) | 9 (60.0%) | 8 (57.1%) | 8 (57.1%) | 0 |
| Day 57 | | | | | |
| N | 14 | 15 | 13 | 13 | 13 |
| Geometric mean | 37.5 | 64.9 | 127 | 120.3 | 5 (5; 5) |
| (95% CI) | (14.7; 95.8) | (32; 131.6) | (49.1; 328.3) | (49.7; 290.9) | |
| Geometric mean fold increase | 4.6 | 6.8 | 13.4 | 12 | 1 |
| Responders n (%) | 10 (71.4%) | 14 (93.3%) | 12 (92.3%) | 13 (100.0%) | 0 |
| MN50 >= 10 n (%) | 10 (71.4%) | 14 (93.3%) | 12 (92.3%) | 13 (100.0%) | 0 |
| MN50 >= 100 n (%) | 4 (28.6%) | 5 (33.3%) | 8 (61.5%) | 8 (61.5%) | 0 |
| Day 71 | | | | | |
| N | 14 | 15 | 13 | 13 | 13 |
| Geometric mean | 1980.3 | 64.2 | 1016.8 | 173.2 | 5 (5; 5) |
| (95% CI) | (1296; 3025.7) | (32.9; 125.1) | (531.4; 1945.6) | (72.3; 415.1) | |
| Geometric mean fold increase | 198 | 7 | 101.7 | 17.3 | 1 |
| Responders n (%) | 14 (100.0%) | 13 (86.7%) | 13 (100.0%) | 13 (100.0%) | 0 |
| MN50 >= 10 n (%) | 14 (100.0%) | 13 (86.7%) | 13 (100.0%) | 13 (100.0%) | 0 |
| MN50 >= 100 n (%) | 14 (100.0%) | 7 (46.7%) | 12 (92.3%) | 7 (53.8%) | 0 |
| Day 85 | | | | | |
| N | 14 | 15 | 13 | 13 | 13 |
| Geometric mean | 1284 | 44.8 | 1131 | 142.4 | 5 (5; 5) |
| (95% CI) | (818.6; 2014) | (24.6; 81.5) | (561.8; 2276.6) | (47.2; 429.7) | |
| Geometric mean fold increase | 128.4 | 4.9 | 113.1 | 15 | 1 |
| Responders n (%) | 14 (100.0%) | 13 (86.7%) | 13 (100.0%) | 12 (92.3%) | 0 |
| MN50 >= 10 n (%) | 14 (100.0%) | 13 (86.7%) | 13 (100.0%) | 12 (92.3%) | 0 |
| MN50 >= 100 n (%) | 14 (100.0%) | 3 (20.0%) | 12 (92.3%) | 8 (61.5%) | 0 |

N: number of subjects with data
Responder: 1) if baseline < LLOQ, R >= LLOQ 2) if baseline >= LLOQ, R = 4-fold increase from baseline
Fold Increase: 1) if baseline < LLOQ, FI = value post-baseline/LLOQ 2) if baseline >= LLOQ, FI = Value post-baseline/Baseline Value
Note:
Ad26.ZIKV.001 LD: Ad26.ZIKV.001 $5 \times 10^{10}$ vp;
Ad26.ZIKV.001 HD: Ad26.ZIKV.001 $1 \times 10^{11}$ vp;
PL: Placebo It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. A method for generating an immune response against a Zika virus in a human subject in need thereof, the method comprising administering to the subject a pharmaceutical composition comprising adenoviral vectors of the Ad26 serotype comprising a nucleic acid sequence encoding a Zika virus antigen, wherein the Zika virus antigen comprises the amino acid sequence of SEQ ID NO:2, and a pharmaceutically acceptable carrier, wherein about 5×1010 adenoviral vectors to about 1×1011 adenoviral vectors are administered per dose to the subject in need thereof, and wherein the pharmaceutical composition is administered in two doses to the human subject in a prime-boost regimen.

2. The method of claim 1, wherein about $5\times10^{10}$ adenoviral vectors are administered per dose to the subject in need thereof.

3. The method of claim 1, wherein about $1\times10^{11}$ adenoviral vectors are administered per dose to the subject in need thereof.

4. The method of claim 1, wherein the pharmaceutical composition is administered via an intramuscular injection to the subject in need thereof.

5. The method of claim 1, wherein the first and second dose of the pharmaceutical composition are administered to the human subject about four weeks, about eight weeks, about twelve weeks, about three months, about six months, about nine months, about one year, or about two years apart.

6. The method of claim 5, wherein the first and second dose of the pharmaceutical composition are administered to the human subject about eight weeks apart.

* * * * *

SEQUENCE LISTING

<160> NUMBER OF SEQ ID NOS: 27

<210> SEQ ID NO 1
<211> LENGTH: 1740
<212> TYPE: DNA
<213> ORGANISM: Artificial Sequence
<220> FEATURE:
<223> OTHER INFORMATION: Synthetic construct

<400> SEQUENCE: 1

| | | | | | |
|---|---|---|---|---|---|
| gctgtgacac | tgcctagcca | cagcacccgg | aagctgcaga | ccagaagcca | gacctggctg | 60 |
| gaaagcagag | agtacaccaa | gcacctgatc | cgggtggaaa | actggatctt | ccggaacccc | 120 |
| ggcttcgccc | tggccgctgc | tgctattgct | tggctgctgg | gcagcagcac | cagccagaaa | 180 |
| gtgatctacc | tcgtgatgat | cctgctgatc | gcccctgcct | acagcatccg | gtgtatcggc | 240 |
| gtgtccaacc | gggacttcgt | ggaaggcatg | agcggcggca | catgggtgga | cgtggtgctg | 300 |
| gaacatggcg | gctgcgtgac | agtgatggcc | caggacaagc | ccaccgtgga | catcgagctc | 360 |
| gtgaccacca | ccgtgtccaa | tatggccgaa | gtgcggagct | actgctacga | ggccagcatc | 420 |
| agcgacatgg | ccagcgacag | cagatgccct | acacagggcg | aggcctacct | ggacaagcag | 480 |
| tccgacaccc | agtacgtgtg | caagcggacc | ctggtggata | gaggctgggg | caatggctgc | 540 |
| ggcctgtttg | gcaagggcag | cctcgtgacc | tgcgccaagt | tcgcctgcag | caagaagatg | 600 |
| accggcaaga | gcatccagcc | cgagaacctg | gaataccgga | tcatgctgag | cgtgcacggc | 660 |
| agccagcact | ccggcatgat | cgtgaacgac | accggccacg | agacagacga | gaaccgggcc | 720 |
| aaggtggaaa | tcacccccaa | cagccctaga | gccgaggcca | cactgggcgg | ctttggatct | 780 |
| ctgggcctgg | actgcgagcc | tagaaccggc | ctggatttca | cgacctgta | ctacctgacc | 840 |
| atgaacaaca | aacactggct | ggtgcacaaa | gagtggttcc | acgacatccc | cctgccctgg | 900 |
| catgccggcg | ctgatacagg | cacaccccac | tggaacaaca | agaggccct | ggtggagttc | 960 |
| aaggacgccc | acgccaagag | gcagaccgtg | gtggtgctgg | atctcagga | aggcgccgtg | 1020 |
| catacagctc | tggctggcgc | cctggaagcc | gaaatggatg | cgctaaggg | cagactgtcc | 1080 |
| agcggccacc | tgaagtgccg | gctgaagatg | gacaagctgc | ggctgaaggg | cgtgtcctac | 1140 |
| agcctgtgta | ccgccgcctt | caccttcacc | aagatccccg | ccgagacact | gcacggcacc | 1200 |
| gtgactgtgg | aagtgcagta | cgccggcacc | gacggccctt | gtaaagtgcc | tgctcagatg | 1260 |
| gccgtggata | tgcagaccct | gaccctgtgt | ggcaggctga | tcaccgccaa | ccctgtgatc | 1320 |
| accgagagca | ccgagaacag | caagatgatg | ctggaactgg | acccaccctt | cggcgacagc | 1380 |
| tacatcgtga | tcggcgtggg | agagaagaag | atcacccacc | actggcacag | aagcggcagc | 1440 |
| accatcggca | aggcctttga | ggctacagtg | cggggagcca | agagaatggc | cgtgctggga | 1500 |
| gataccgcct | gggacttgg | ctctgtgggc | ggagccctga | actctctggg | caagggaatc | 1560 |
| caccagatct | tcggcgctgc | cttcaagagc | ctgttcggcg | gcatgagctg | gttcagccag | 1620 |
| atcctgatcg | gcaccctgct | gatgtggctg | ggcctgaaca | ccaagaacgg | ctccatcagc | 1680 |
| ctgatgtgcc | tggctctggg | aggcgtgctg | atcttcctga | gcacagccgt | gtccgcctga | 1740 |

<210> SEQ ID NO 2
<211> LENGTH: 579
<212> TYPE: PRT
<213> ORGANISM: Artificial Sequence
<220> FEATURE:
<223> OTHER INFORMATION: Synthetic construct

<400> SEQUENCE: 2

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
            35                  40                  45

Ile Ala Trp Leu Leu Gly Ser Ser Thr Ser Gln Lys Val Ile Tyr Leu
50                      55                  60

Val Met Ile Leu Leu Ile Ala Pro Ala Tyr Ser Ile Arg Cys Ile Gly
65                  70                  75                  80

Val Ser Asn Arg Asp Phe Val Glu Gly Met Ser Gly Thr Trp Val
                85                  90                  95

Asp Val Val Leu Glu His Gly Gly Cys Val Thr Val Met Ala Gln Asp
                100                 105                 110

Lys Pro Thr Val Asp Ile Glu Leu Val Thr Thr Thr Val Ser Asn Met
            115                 120                 125

Ala Glu Val Arg Ser Tyr Cys Tyr Glu Ala Ser Ile Ser Asp Met Ala
            130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
                180                 185                 190

Lys Phe Ala Cys Ser Lys Lys Met Thr Gly Lys Ser Ile Gln Pro Glu
            195                 200                 205

Asn Leu Glu Tyr Arg Ile Met Leu Ser Val His Gly Ser Gln His Ser
            210                 215                 220

Gly Met Ile Val Asn Asp Thr Gly His Glu Thr Asp Glu Asn Arg Ala
225                 230                 235                 240

Lys Val Glu Ile Thr Pro Asn Ser Pro Arg Ala Glu Ala Thr Leu Gly
                245                 250                 255

Gly Phe Gly Ser Leu Gly Leu Asp Cys Glu Pro Arg Thr Gly Leu Asp
                260                 265                 270

Phe Ser Asp Leu Tyr Tyr Leu Thr Met Asn Asn Lys His Trp Leu Val
            275                 280                 285

His Lys Glu Trp Phe His Asp Ile Pro Leu Pro Trp His Ala Gly Ala
            290                 295                 300

Asp Thr Gly Thr Pro His Trp Asn Asn Lys Glu Ala Leu Val Glu Phe
305                 310                 315                 320

Lys Asp Ala His Ala Lys Arg Gln Thr Val Val Val Leu Gly Ser Gln
                325                 330                 335

Glu Gly Ala Val His Thr Ala Leu Ala Gly Ala Leu Glu Ala Glu Met
                340                 345                 350

Asp Gly Ala Lys Gly Arg Leu Ser Ser Gly His Leu Lys Cys Arg Leu
            355                 360                 365

Lys Met Asp Lys Leu Arg Leu Lys Gly Val Ser Tyr Ser Leu Cys Thr
            370                 375                 380

Ala Ala Phe Thr Phe Thr Lys Ile Pro Ala Glu Thr Leu His Gly Thr
385                 390                 395                 400

Val Thr Val Glu Val Gln Tyr Ala Gly Thr Asp Gly Pro Cys Lys Val
                405                 410                 415
```

```
Pro Ala Gln Met Ala Val Asp Met Gln Thr Leu Thr Pro Val Gly Arg
            420                 425                 430

Leu Ile Thr Ala Asn Pro Val Ile Thr Glu Ser Thr Glu Asn Ser Lys
        435                 440                 445

Met Met Leu Glu Leu Asp Pro Pro Phe Gly Asp Ser Tyr Ile Val Ile
    450                 455                 460

Gly Val Gly Glu Lys Lys Ile Thr His His Trp His Arg Ser Gly Ser
465                 470                 475                 480

Thr Ile Gly Lys Ala Phe Glu Ala Thr Val Arg Gly Ala Lys Arg Met
                485                 490                 495

Ala Val Leu Gly Asp Thr Ala Trp Asp Phe Gly Ser Val Gly Gly Ala
            500                 505                 510

Leu Asn Ser Leu Gly Lys Gly Ile His Gln Ile Phe Gly Ala Ala Phe
        515                 520                 525

Lys Ser Leu Phe Gly Gly Met Ser Trp Phe Ser Gln Ile Leu Ile Gly
    530                 535                 540

Thr Leu Leu Met Trp Leu Gly Leu Asn Thr Lys Asn Gly Ser Ile Ser
545                 550                 555                 560

Leu Met Cys Leu Ala Leu Gly Gly Val Leu Ile Phe Leu Ser Thr Ala
                565                 570                 575

Val Ser Ala
```

<210> SEQ ID NO 3
<211> LENGTH: 1559
<212> TYPE: DNA
<213> ORGANISM: Artificial Sequence
<220> FEATURE:
<223> OTHER INFORMATION: Synthetic construct

<400> SEQUENCE: 3

```
gctgtgacac tgcctagcca cagcacccgg aagctgcaga ccagaagcca gacctggctg      60
gaaagcagag agtacaccaa gcacctgatc cgggtggaaa actggatctt ccggaacccc     120
ggcttcgccc tggccgctgc tgctattgct tggctgctgg gcagcagcac cagccagaaa     180
gtgatctacc tcgtgatgat cctgctgatc gcccctgcct acagcatccg tgtatcggc      240
gtgtccaacc gggacttcgt ggaaggcatg agcggcggca catgggtgga cgtggtgctg     300
gaacatggcg gctgcgtgac agtgatggcc caggacaagc ccaccgtgga catcgagctc     360
gtgaccacca ccgtgtccaa tatggccgaa gtgcggagct actgctacga ggccagcatc     420
agcgacatgg ccagcgacag cagatgccct acacagggcg aggcctacct ggacaagcag     480
tccgacaccc agtacgtgtg caagcggacc ctggtggata gaggctgggg caatggctgc     540
ggcctgtttg gcaagggcag cctcgtgacc tgcgccaagt tcgcctgcag caagaagatg     600
accggcaaga gcatccagcc cgagaacctg gaataccgga tcatgctgag cgtgcacggc     660
agccagcact ccggcatgat cgtgaacgac accggccacg agacagacga gaaccgggcc     720
aaggtggaaa tcacccccaa cagccctaga gccgaggcca cactgggcgg ctttggatct     780
ctgggcctgg actgcgagcc tagaaccggc ctggatttca gcgacctgta ctacctgacc     840
atgaacaaca aacactggct ggtgcacaaa gagtggttcc acgacatccc cctgccctgg     900
catgccggcg ctgatacagg cacaccccac tggaacaaca agaggccct ggtggagttc      960
aaggacgccc acgccaagag gcagaccgtg gtggtgctgg atctcaggaa ggcgccgtg     1020
catacagctc tggctggcgc cctggaagcc gaaatggatg cgctaaggg cagactgtcc     1080
agcggccacc tgaagtgccg gctgaagatg gacaagctgc ggctgaaggg cgtgtcctac    1140
```

```
agcctgtgta ccgccgcctt caccttcacc aagatccccg ccgagacact gcacggcacc    1200
gtgactgtgg aagtgcagta cgccggcacc gacggcccct gtaaagtgcc tgctcagatg    1260
gccgtggata tgcagaccct gacccctgtg gcaggctga tcaccgccaa ccctgtgatc     1320
accgagagca ccgagaacag caagatgatg ctggaactgg acccacccctt cggcgacagc   1380 tacatcgtga tcggcgtggg agagaagaag atcacccacc actggcacag aagcggcagc   1440
accatcggca aggcctttga ggctacagtg cggggagcca agagaatggc cgtgctggga   1500
gataccgcct gggactttgg ctctgtgggc ggagccctga actctctggg caagggtga    1559
```

<210> SEQ ID NO 4
<211> LENGTH: 519
<212> TYPE: PRT
<213> ORGANISM: Artificial Sequence
<220> FEATURE:
<223> OTHER INFORMATION: Synthetic construct

<400> SEQUENCE: 4

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser Ile Arg Cys Ile Gly
65                  70                  75                  80

Val Ser Asn Arg Asp Phe Val Glu Gly Met Ser Gly Gly Thr Trp Val
                85                  90                  95

Asp Val Val Leu Glu His Gly Gly Cys Val Thr Val Met Ala Gln Asp
            100                 105                 110

Lys Pro Thr Val Asp Ile Glu Leu Val Thr Thr Thr Val Ser Asn Met
        115                 120                 125

Ala Glu Val Arg Ser Tyr Cys Tyr Glu Ala Ser Ile Ser Asp Met Ala
    130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
            180                 185                 190

Lys Phe Ala Cys Ser Lys Lys Met Thr Gly Lys Ser Ile Gln Pro Glu
        195                 200                 205

Asn Leu Glu Tyr Arg Ile Met Leu Ser Val His Gly Ser Gln His Ser
    210                 215                 220

Gly Met Ile Val Asn Asp Thr Gly His Glu Thr Asp Glu Asn Arg Ala
225                 230                 235                 240

Lys Val Glu Ile Thr Pro Asn Ser Pro Arg Ala Glu Ala Thr Leu Gly
                245                 250                 255

Gly Phe Gly Ser Leu Gly Leu Asp Cys Glu Pro Arg Thr Gly Leu Asp
            260                 265                 270

Phe Ser Asp Leu Tyr Tyr Leu Thr Met Asn Asn Lys His Trp Leu Val
        275                 280                 285
```

His Lys Glu Trp Phe His Asp Ile Pro Leu Pro Trp His Gly Ala
290                 295                 300

Asp Thr Gly Thr Pro His Trp Asn Asn Lys Glu Ala Leu Val Glu Phe
305                 310                 315                 320

Lys Asp Ala His Ala Lys Arg Gln Thr Val Val Leu Gly Ser Gln
            325                 330                 335

Glu Gly Ala Val His Thr Ala Leu Ala Gly Ala Leu Glu Ala Glu Met
            340                 345                 350

Asp Gly Ala Lys Gly Arg Leu Ser Ser Gly His Leu Lys Cys Arg Leu
            355                 360                 365

Lys Met Asp Lys Leu Arg Leu Lys Gly Val Ser Tyr Ser Leu Cys Thr
370                 375                 380

Ala Ala Phe Thr Phe Thr Lys Ile Pro Ala Glu Thr Leu His Gly Thr
385                 390                 395                 400

Val Thr Val Glu Val Gln Tyr Ala Gly Thr Asp Gly Pro Cys Lys Val
                405                 410                 415

Pro Ala Gln Met Ala Val Asp Met Gln Thr Leu Thr Pro Val Gly Arg
            420                 425                 430

Leu Ile Thr Ala Asn Pro Val Ile Thr Glu Ser Thr Glu Asn Ser Lys
            435                 440                 445

Met Met Leu Glu Leu Asp Pro Pro Phe Gly Asp Ser Tyr Ile Val Ile
450                 455                 460

Gly Val Gly Glu Lys Lys Ile Thr His His Trp His Arg Ser Gly Ser
465                 470                 475                 480

Thr Ile Gly Lys Ala Phe Glu Ala Thr Val Arg Gly Ala Lys Arg Met
                485                 490                 495

Ala Val Leu Gly Asp Thr Ala Trp Asp Phe Gly Ser Val Gly Gly Ala
            500                 505                 510

Leu Asn Ser Leu Gly Lys Gly
            515

<210> SEQ ID NO 5
<211> LENGTH: 1449
<212> TYPE: DNA
<213> ORGANISM: Artificial Sequence
<220> FEATURE:
<223> OTHER INFORMATION: Synthetic construct

<400> SEQUENCE: 5

```
gctgtgacac tgcctagcca cagcacccgg aagctgcaga ccagaagcca gacctggctg      60
gaaagcagag agtacaccaa gcacctgatc cgggtggaaa actggatctt ccggaacccc     120
ggcttcgccc tggccgctgc tgctattgct tggctgctgg gcagcagcac cagccagaaa     180
gtgatctacc tcgtgatgat cctgctgatc gccgctgcct acagcatccg tgtatcggc      240 gtgtccaacc gggacttcgt ggaaggcatg agcggcggca catgggtgga cgtggtgctg     300
gaacatggcg gctgcgtgac cgtgatggcc caggacaagc ccaccgtgga catcgagctc     360
gtgaccacca ccgtgtccaa tatggccgaa gtgcggagct actgctacga ggccagcatc     420
agcgacatgg ccagcgacag cagatgccct acacagggcg aggcctacct ggacaagcag     480
tccgacaccc agtacgtgtg caagcggacc ctggtggata gaggctgggg caatggctgc     540
ggcctgtttg gcaagggcag cctcgtgacc tgcgccaagt tcgcctgcag caagaagatg     600
accggcaaga gcatccagcc cgagaacctg gaataccgga tcatgctgag cgtgcacggc     660
agccagcact ccggcatgat cgtgaacgac accggccacg agacagacga gaaccgggcc     720
```

```
aaggtggaaa tcacccccaa cagccctaga gccgaggcca cactgggcgg ctttggatct    780
ctgggcctgg actgcgagcc tagaaccggc tggatttca gcgacctgta ctacctgacc     840
atgaacaaca aacactggct ggtgcacaaa gagtggttcc acgacatccc cctgccctgg    900
catgccggcg ctgatacagg cacccccac tggaacaaca agaggccct ggtggagttc      960 aaggacgccc acgccaagag gcagaccgtg gtggtgctgg atctcagga aggcgccgtg    1020 catacagctc tggctggcgc cctggaagcc gaaatggatg cgctaaggg cagactgtcc    1080 agcggccacc tgaagtgccg gctgaagatg gacaagctgc ggctgaaggg cgtgtcctac    1140
agcctgtgta ccgccgcctt caccttcacc aagatcccg ccgagacact gcacggcacc     1200
gtgactgtgg aagtgcagta cgccggcacc gacggcccttgtaaagtgcc tgctcagatg    1260 gccgtggata tgcagaccct gacccctgtg ggcaggctga tcaccgccaa ccctgtgatc    1320
accgagagca ccgagaacag caagatgatg ctggaactgg acccaccctt cggcgacagc    1380
tacatcgtga tcggcgtggg agagaagaag atcacccacc actggcacag aagcggcagc    1440
accatctga                                                           1449
```

<210> SEQ ID NO 6
<211> LENGTH: 482
<212> TYPE: PRT
<213> ORGANISM: Artificial Sequence
<220> FEATURE:
<223> OTHER INFORMATION: Synthetic construct

<400> SEQUENCE: 6

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser Ile Arg Cys Ile Gly
65                  70                  75                  80

Val Ser Asn Arg Asp Phe Val Glu Gly Met Ser Gly Gly Thr Trp Val
                85                  90                  95

Asp Val Val Leu Glu His Gly Gly Cys Val Thr Val Met Ala Gln Asp
            100                 105                 110

Lys Pro Thr Val Asp Ile Glu Leu Val Thr Thr Thr Val Ser Asn Met
        115                 120                 125

Ala Glu Val Arg Ser Tyr Cys Tyr Glu Ala Ser Ile Ser Asp Met Ala
    130                 135                 140

Ser Asp Ser Arg Cys Pro Thr Gln Gly Glu Ala Tyr Leu Asp Lys Gln
145                 150                 155                 160

Ser Asp Thr Gln Tyr Val Cys Lys Arg Thr Leu Val Asp Arg Gly Trp
                165                 170                 175

Gly Asn Gly Cys Gly Leu Phe Gly Lys Gly Ser Leu Val Thr Cys Ala
            180                 185                 190

Lys Phe Ala Cys Ser Lys Lys Met Thr Gly Lys Ser Ile Gln Pro Glu
        195                 200                 205

Asn Leu Glu Tyr Arg Ile Met Leu Ser Val His Gly Ser Gln His Ser
    210                 215                 220

Gly Met Ile Val Asn Asp Thr Gly His Glu Thr Asp Glu Asn Arg Ala
```

```
                    225                 230                 235                 240
        Lys Val Glu Ile Thr Pro Asn Ser Pro Arg Ala Glu Ala Thr Leu Gly
                        245                 250                 255

Gly Phe Gly Ser Leu Gly Leu Asp Cys Glu Pro Arg Thr Gly Leu Asp
                    260                 265                 270

Phe Ser Asp Leu Tyr Tyr Leu Thr Met Asn Asn Lys His Trp Leu Val
                275                 280                 285

His Lys Glu Trp Phe His Asp Ile Pro Leu Pro Trp His Ala Gly Ala
                290                 295                 300

Asp Thr Gly Thr Pro His Trp Asn Asn Lys Glu Ala Leu Val Glu Phe
        305                 310                 315                 320

Lys Asp Ala His Ala Lys Arg Gln Thr Val Val Leu Gly Ser Gln
                        325                 330                 335

Glu Gly Ala Val His Thr Ala Leu Ala Gly Ala Leu Glu Ala Glu Met
                    340                 345                 350

Asp Gly Ala Lys Gly Arg Leu Ser Ser Gly His Leu Lys Cys Arg Leu
                    355                 360                 365

Lys Met Asp Lys Leu Arg Leu Lys Gly Val Ser Tyr Ser Leu Cys Thr
                370                 375                 380

Ala Ala Phe Thr Phe Thr Lys Ile Pro Ala Glu Thr Leu His Gly Thr
        385                 390                 395                 400

Val Thr Val Glu Val Gln Tyr Ala Gly Thr Asp Gly Pro Cys Lys Val
                        405                 410                 415

Pro Ala Gln Met Ala Val Asp Met Gln Thr Leu Thr Pro Val Gly Arg
                    420                 425                 430

Leu Ile Thr Ala Asn Pro Val Ile Thr Glu Ser Thr Glu Asn Ser Lys
                    435                 440                 445

Met Met Leu Glu Leu Asp Pro Pro Phe Gly Asp Ser Tyr Ile Val Ile
                450                 455                 460

Gly Val Gly Glu Lys Lys Ile Thr His His Trp His Arg Ser Gly Ser
        465                 470                 475                 480

Thr Ile

<210> SEQ ID NO 7
<211> LENGTH: 1515
<212> TYPE: DNA
<213> ORGANISM: Artificial Sequence
<220> FEATURE:
<223> OTHER INFORMATION: Synthetic construct

<400> SEQUENCE: 7
atcagatgca tcggcgtgtc caaccgggac ttcgtggaag gcatgagcgg cggcacatgg       60
gtggacgtgg tgctggaaca tggcggctgc gtgacagtga tggcccagga caagcccacc      120
gtggacatcg agctcgtgac caccaccgtg tccaatatgg ccgaagtgcg gagctactgc      180
tacgaggcca gcatcagcga catggccagc gacagcagat gccctacaca gggcgaggcc      240
tacctggaca gcagagcga cacccagtac gtgtgcaagc ggaccctggt ggatagaggc      300
tggggcaatg gctgcggcct gtttggcaag ggcagcctcg tgacctgcgc caagttcgcc      360
tgcagcaaga gatgaccgg caagagcatc cagcccgaga acctggaata ccggatcatg      420
ctgagcgtgc acggcagcca gcactccggc atgatcgtga cgacaccgg ccacgagaca      480 gacgagaacc gggccaaggt ggaaatcacc cccaacagcc ctagagccga ggccacactg      540
ggcggctttg gatctctggg cctggactgc gagcctagaa ccggcctgga tttcagcgac      600
```

```
ctgtactacc tgaccatgaa caacaagcac tggctggtgc acaaagagtg gttccacgac      660
atccccctgc cctggcatgc tggcgctgat acaggcaccc ctcactgaa caacaaagag       720 gctctggtgg agttcaagga cgcccacgcc aagaggcaga ccgtggtggt gctgggatct     780
caggaaggcg ccgtgcatac agctctggct ggcgccctgg aagccgaaat ggatggcgct     840
aagggcagac tgagcagcgg ccacctgaag tgccggctga agatggacaa gctgcggctg     900
aagggcgtgt cctacagcct gtgtaccgcc gccttcacct tcaccaagat ccccgccgag     960
acactgcacg gcaccgtgac tgtggaagtg cagtacgccg gcaccgacgg cccttgtaaa     1020
gtgcctgctc agatggccgt ggatatgcag accctgaccc ctgtgggcag gctgatcacc     1080
gccaaccctg tgatcaccga gcaccgag aacagcaaga tgatgctgga actggaccca       1140
cccttcggcg acagctacat cgtgatcggc gtgggagaga agaagatcac ccaccactgg     1200
cacagaagcg gcagcaccat cggcaaggcc tttgaggcta cagtgcgggg agccaagaga     1260
atggccgtgc tggagatac cgcctggac tttggctctg tgggcggagc cctgaactct       1320
ctgggcaagg gaatccacca gatcttcggc gctgccttca gagcctgtt cggcggcatg      1380 agctggttca gccagatcct gatcggcacc ctgctgatgt ggctgggcct gaacaccaag     1440
aacggctcca tcagcctgat gtgcctggct ctggaggcg tgctgatctt cctgagcaca      1500
gccgtgtccg cctga                                                      1515
```

<210> SEQ ID NO 8
<211> LENGTH: 504
<212> TYPE: PRT
<213> ORGANISM: Artificial Sequence
<220> FEATURE:
<223> OTHER INFORMATION: Synthetic construct

<400> SEQUENCE: 8

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
```

|     |     |     |     | 195 |     |     |     |     | 200 |     |     |     |     | 205 |     |     |     |
| --- | --- | --- | --- | --- | --- | --- | --- | --- | --- | --- | --- | --- | --- | --- | --- | --- | --- |
| Lys | His | Trp | Leu | Val | His | Lys | Glu | Trp | Phe | His | Asp | Ile | Pro | Leu | Pro |     |     |
|     | 210 |     |     |     |     | 215 |     |     |     |     | 220 |     |     |     |     |     |     |
| Trp | His | Ala | Gly | Ala | Asp | Thr | Gly | Thr | Pro | His | Trp | Asn | Asn | Lys | Glu |     |     |
| 225 |     |     |     |     | 230 |     |     |     |     | 235 |     |     |     |     | 240 |     |     |
| Ala | Leu | Val | Glu | Phe | Lys | Asp | Ala | His | Ala | Lys | Arg | Gln | Thr | Val | Val |     |     |
|     |     |     |     | 245 |     |     |     |     | 250 |     |     |     |     | 255 |     |     |     |
| Val | Leu | Gly | Ser | Gln | Glu | Gly | Ala | Val | His | Thr | Ala | Leu | Ala | Gly | Ala |     |     |
|     |     |     | 260 |     |     |     |     | 265 |     |     |     |     | 270 |     |     |     |     |
| Leu | Glu | Ala | Glu | Met | Asp | Gly | Ala | Lys | Gly | Arg | Leu | Ser | Ser | Gly | His |     |     |
|     |     |     | 275 |     |     |     |     | 280 |     |     |     |     | 285 |     |     |     |     |
| Leu | Lys | Cys | Arg | Leu | Lys | Met | Asp | Lys | Leu | Arg | Leu | Lys | Gly | Val | Ser |     |     |
|     | 290 |     |     |     |     | 295 |     |     |     |     | 300 |     |     |     |     |     |     |
| Tyr | Ser | Leu | Cys | Thr | Ala | Ala | Phe | Thr | Phe | Thr | Lys | Ile | Pro | Ala | Glu |     |     |
| 305 |     |     |     |     | 310 |     |     |     |     | 315 |     |     |     |     | 320 |     |     |
| Thr | Leu | His | Gly | Thr | Val | Thr | Val | Glu | Val | Gln | Tyr | Ala | Gly | Thr | Asp |     |     |
|     |     |     |     | 325 |     |     |     |     | 330 |     |     |     |     | 335 |     |     |     |
| Gly | Pro | Cys | Lys | Val | Pro | Ala | Gln | Met | Ala | Val | Asp | Met | Gln | Thr | Leu |     |     |
|     |     |     | 340 |     |     |     |     | 345 |     |     |     |     | 350 |     |     |     |     |
| Thr | Pro | Val | Gly | Arg | Leu | Ile | Thr | Ala | Asn | Pro | Val | Ile | Thr | Glu | Ser |     |     |
|     |     |     | 355 |     |     |     |     | 360 |     |     |     |     | 365 |     |     |     |     |
| Thr | Glu | Asn | Ser | Lys | Met | Met | Leu | Glu | Leu | Asp | Pro | Pro | Phe | Gly | Asp |     |     |
|     | 370 |     |     |     |     | 375 |     |     |     |     | 380 |     |     |     |     |     |     |
| Ser | Tyr | Ile | Val | Ile | Gly | Val | Gly | Glu | Lys | Lys | Ile | Thr | His | His | Trp |     |     |
| 385 |     |     |     |     | 390 |     |     |     |     | 395 |     |     |     |     | 400 |     |     |
| His | Arg | Ser | Gly | Ser | Thr | Ile | Gly | Lys | Ala | Phe | Glu | Ala | Thr | Val | Arg |     |     |
|     |     |     |     | 405 |     |     |     |     | 410 |     |     |     |     | 415 |     |     |     |
| Gly | Ala | Lys | Arg | Met | Ala | Val | Leu | Gly | Asp | Thr | Ala | Trp | Asp | Phe | Gly |     |     |
|     |     |     | 420 |     |     |     |     | 425 |     |     |     |     | 430 |     |     |     |     |
| Ser | Val | Gly | Gly | Ala | Leu | Asn | Ser | Leu | Gly | Lys | Gly | Ile | His | Gln | Ile |     |     |
|     |     |     | 435 |     |     |     |     | 440 |     |     |     |     | 445 |     |     |     |     |
| Phe | Gly | Ala | Ala | Phe | Lys | Ser | Leu | Phe | Gly | Gly | Met | Ser | Trp | Phe | Ser |     |     |
|     | 450 |     |     |     |     | 455 |     |     |     |     | 460 |     |     |     |     |     |     |
| Gln | Ile | Leu | Ile | Gly | Thr | Leu | Leu | Met | Trp | Leu | Gly | Leu | Asn | Thr | Lys |     |     |
| 465 |     |     |     |     | 470 |     |     |     |     | 475 |     |     |     |     | 480 |     |     |
| Asn | Gly | Ser | Ile | Ser | Leu | Met | Cys | Leu | Ala | Leu | Gly | Gly | Val | Leu | Ile |     |     |
|     |     |     |     | 485 |     |     |     |     | 490 |     |     |     |     | 495 |     |     |     |
| Phe | Leu | Ser | Thr | Ala | Val | Ser | Ala |     |     |     |     |     |     |     |     |     |     |
|     |     |     | 500 |     |     |     |     |     |     |     |     |     |     |     |     |     |     |

<210> SEQ ID NO 9
<211> LENGTH: 1335
<212> TYPE: DNA
<213> ORGANISM: Artificial Sequence
<220> FEATURE:
<223> OTHER INFORMATION: Synthetic construct

<400> SEQUENCE: 9

| atcagatgca tcggcgtgtc caaccgggac ttcgtggaag gcatgagcgg cggcacatgg | 60 |
| gtggacgtgg tgctggaaca tggcggctgc gtgacagtga tggcccagga caagcccacc | 120 |
| gtggacatcg agctcgtgac caccaccgtg tccaatatgg ccgaagtgcg gagctactgc | 180 |
| tacgaggcca gcatcagcga catggccagc gacagcagat gccctacaca gggcgaggcc | 240 |
| tacctggaca agcagagcga cacccagtac gtgtgcaagc ggaccctggt ggatagaggc | 300 |

```
tggggcaatg gctgcggcct gtttggcaag ggcagcctcg tgacctgcgc caagttcgcc     360
tgcagcaaga agatgaccgg caagagcatc cagcccgaga acctggaata ccggatcatg     420
ctgagcgtgc acggcagcca gcactccggc atgatcgtga acgacaccgg ccacgagaca     480
gacgagaacc gggccaaggt ggaaatcacc cccaacagcc ctagagccga ggccacactg     540
ggcggctttg gatctctggg cctggactgc gagcctagaa ccggcctgga tttcagcgac     600
ctgtactacc tgaccatgaa caacaagcac tggctggtgc acaaagagtg gttccacgac     660 atcccctgc cctggcatgc tggcgctgat acaggcaccc ctcactggaa caacaaagag     720
gctctggtgg agttcaagga cgcccacgcc aagaggcaga ccgtggtggt gctgggatct     780
caggaaggcg ccgtgcatac agctctggct ggcgccctgg aagccgaaat ggatggcgct     840
aagggcagac tgagcagcgg ccacctgaag tgccggctga agatggacaa gctgcggctg     900
aagggcgtgt cctacagcct gtgtaccgcc gccttcacct tcaccaagat ccccgccgag     960
acactgcacg gcaccgtgac tgtggaagtg cagtacgccg gcaccgacgg cccttgtaaa    1020
gtgcctgctc agatggccgt ggatatgcag accctgaccc ctgtgggcag gctgatcacc    1080
gccaaccctg tgatcaccga gagcaccgag aacagcaaga tgatgctgga actggaccca    1140
cccttcggcg acagctacat cgtgatcggc gtggagaga agaagatcac ccaccactgg    1200
cacagaagcg gcagcaccat cggcaaggcc tttgaggcta cagtgcgggg agccaagaga    1260
atggccgtgc tgggagatac cgcctgggac tttggctctg tgggcggagc cctgaactct    1320
ctgggcaagg gatga                                                    1335
```

<210> SEQ ID NO 10
<211> LENGTH: 444
<212> TYPE: PRT
<213> ORGANISM: Artificial Sequence
<220> FEATURE:
<223> OTHER INFORMATION: Synthetic construct

<400> SEQUENCE: 10

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175
```

Glu Ala Thr Leu Gly Gly Phe Gly Ser Leu Gly Leu Asp Cys Glu Pro
                180                 185                 190

Arg Thr Gly Leu Asp Phe Ser Asp Leu Tyr Tyr Leu Thr Met Asn Asn
            195                 200                 205

Lys His Trp Leu Val His Lys Glu Trp Phe His Asp Ile Pro Leu Pro
        210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
        340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
        370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly
        435                 440

<210> SEQ ID NO 11
<211> LENGTH: 1224
<212> TYPE: DNA
<213> ORGANISM: Artificial Sequence
<220> FEATURE:
<223> OTHER INFORMATION: Synthetic construct

<400> SEQUENCE: 11
atcagatgca tcggcgtgtc caaccgggac ttcgtggaag gcatgagcgg cggcacatgg     60
gtggacgtgg tgctggaaca tggcggctgc gtgacagtga tggcccagga caagcccacc    120
gtggacatcg agctcgtgac caccaccgtg tccaatatgg ccgaagtgcg gagctactgc    180
tacgaggcca gcatcagcga catggccagc gacagcagat gccctacaca gggcgaggcc    240
tacctggaca gcagagcga cacccagtac gtgtgcaagc ggaccctggt ggatagaggc    300
tggggcaatg gctgcggcct gtttggcaag ggcagcctcg tgacctgcgc caagttcgcc    360
tgcagcaaga agatgaccgg caagagcatc cagcccgaga acctggaata ccggatcatg    420
ctgagcgtgc acggcagcca gcactccggc atgatcgtga cgacaccggg ccacgagaca    480
gacgagaacc gggccaaggt ggaaatcacc cccaacagcc ctagagccga ggccacactg    540

```
ggcggctttg gatctctggg cctggactgc gagcctagaa ccggcctgga tttcagcgac    600
ctgtactacc tgaccatgaa caacaagcac tggctggtgc acaaagagtg gttccacgac    660
atccccctgc cctggcatgc tggcgctgat acaggcaccc tcactggaa caacaaagag     720
gctctggtgg agttcaagga cgcccacgcc aagaggcaga ccgtggtggt gctgggatct    780
caggaaggcg ccgtgcatac agctctggct ggcgccctgg aagccgaaat ggatggcgct    840
aagggcagac tgagcagcgg ccacctgaag tgccggctga agatggacaa gctgcggctg    900
aagggcgtgt cctacagcct gtgtaccgcc gccttcacct tcaccaagat ccccgccgag    960
acactgcacg gcaccgtgac tgtggaagtg cagtacgccg gcaccgacgg ccttgtaaa   1020
gtgcctgctc agatggccgt ggatatgcag accctgaccc ctgtgggcag gctgatcacc   1080
gccaaccctg tgatcaccga gagcaccgag aacagcaaga tgatgctgga actggaccca   1140
cccttcggcg acagctacat cgtgatcggc gtgggagaga agaagatcac ccaccactgg   1200
cacagaagcg gcagcaccat ctga                                         1224
```

<210> SEQ ID NO 12
<211> LENGTH: 407
<212> TYPE: PRT
<213> ORGANISM: Artificial Sequence
<220> FEATURE:
<223> OTHER INFORMATION: Synthetic construct

<400> SEQUENCE: 12

```
Ile Arg Cys Ile Gly Val Ser Asn Arg Asp Phe Val Glu Gly Met Ser
1               5                  10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile
                405
```

<210> SEQ ID NO 13
<211> LENGTH: 72
<212> TYPE: DNA
<213> ORGANISM: Artificial Sequence
<220> FEATURE:
<223> OTHER INFORMATION: Synthetic construct

<400> SEQUENCE: 13

```
atgggcaaaa gatccgccgg cagcatcatg tggctggcca gtctggctgt cgtgatcgcc    60
tgtgctggcg cc                                                        72
```

<210> SEQ ID NO 14
<211> LENGTH: 24
<212> TYPE: PRT
<213> ORGANISM: Artificial Sequence
<220> FEATURE:
<223> OTHER INFORMATION: Synthetic construct

<400> SEQUENCE: 14

```
Met Gly Lys Arg Ser Ala Gly Ser Ile Met Trp Leu Ala Ser Leu Ala
1               5                   10                  15

Val Val Ile Ala Cys Ala Gly Ala
            20
```

<210> SEQ ID NO 15
<211> LENGTH: 10662
<212> TYPE: DNA
<213> ORGANISM: Artificial Sequence
<220> FEATURE:
<223> OTHER INFORMATION: Synthetic construct

<400> SEQUENCE: 15

```
gtgaatcaga ctgcgacagt tcgagtttga agcgaaagct agcaacagta tcaacaggtt    60
ttatttggaa tttggaaacg agagtttctg tcatgaaaaa acccaaaaaa gaaatccgga   120
ggattccgga ttgtcaatat gctaaaacgc ggagtagccc gtgtgagccc ctttggggc    180
```

```
ttgaagaggc tgccagccgg acttctgctg ggtcatgggc ccatcaggat ggtcttggcg    240
attctagcct ttttgagatt cacggcaatc aagccatcac tgggtctcat caatagatgg    300
ggttcagtgg ggaaaaaaga ggctatggaa ataataaaga agttcaagaa agatctggct    360
gccatgctga gaataatcaa tgctaggaag gagaagaaga gacgaggcgc agatactagt    420
gtcggaattg ttggcctcct gctgaccaca gctatggcag cggaggtcac tagacgtggg    480
agtgcatact atatgtactt ggacagaaac gatgctgggg aggccatatc ttttccaacc    540
acattgggga tgaataagtg ttatatacag atcatggatc ttggacacat gtgtgatgcc    600
accatgagct atgaatgccc tatgctggat gaggggtgg aaccagatga cgtcgattgt    660
tggtgcaaca cgacgtcaac ttgggttgtg tacggaacct gccatcacaa aaaggtgaa    720 gcacggagat ctagaagagc tgtgacgctc ccctcccatt ccactaggaa gctgcaaacg    780
cggtcgcaaa cctggttgga atcaagagaa tacacaaagc acttgattag agtcgaaaat    840
tggatattta ggaaccctgg cttcgcgtta gcagcagctg ccatcgcttg gcttttggga    900
agctcaacga gccaaaaagt catatacttg gtcatgatac tgctgattgc cccggcatac    960
agcatcaggt gcataggagt cagcaatagg gactttgtgg aaggtatgtc aggtgggacc   1020
tgggttgatg ttgtcttgga acatggaggt tgtgtcaccg taatggcaca ggacaaaccg   1080
actgtcgaca tagagctggt tacaacaaca gtcagcaaca tggcggaggt aagatcctac   1140
tgctatgagg catcaatatc agacatggct tcggacagcc gctgcccaac acaaggtgaa   1200
gcctaccttg acaagcaatc agacactcaa tatgtctgca aaagaacgtt agtggacaga   1260 ggctgggaa atggatgtgg acttttggc aaagggagcc tggtgacatg cgctaagttt   1320
gcatgctcca gaaaatgac cgggaagagc atccagccag agaatctgga gtaccggata   1380
atgctgtcag ttcatggctc ccagcacagt gggatgattg ttaatgacac aggacatgaa   1440
actgatgaga atagagcgaa agttgagata acgcccaatt caccaagagc cgaagccacc   1500
ctggggggtt ttggaagcct aggacttgat tgtgaaccga ggacaggcct tgacttttca   1560
gatttgtatt acttgactat gaataacaag cactggttgg ttcacaagga gtggttccac   1620
gacattccat accttggca cgctggggca gacaccggaa ctccacactg gaacaacaaa   1680
gaagcactgg tagagttcaa ggacgcacat gccaaaaggc aaactgtcgt ggttctaggg   1740
agtcaagaag gagcagttca cacggcccctt gctggagctc tggaggctga tgatggatggt   1800 gcaaagggaa ggctgtcctc tggccacttg aaatgtcgcc tgaaaatgga taaacttaga   1860
ttgaagggcg tgtcatactc cttgtgtact gcagcgttca cattcaccaa gatcccggct   1920
gaaacactgc acgggacagt cacagtggag gtacagtacg cagggacaga tggaccttgc   1980
aaggttccag ctcagatggc ggtggacatg caaactctga ccccagttgg gaggttgata   2040
accgctaacc ccgtaatcac tgaaagcact gagaactcta agatgatgct ggaacttgat   2100
ccaccatttg gggactctta cattgtcata ggagtcgggg agaagaagat cacccaccac   2160
tggcacagga gtggcagcac cattggaaaa gcatttgaag ccactgtgag aggtgccaag   2220
agaatggcag tcttgggaga cacagcctgg gactttggat cagttggagg cgctctcaac   2280 tcattggca agggcatcca tcaaattttt ggagcagctt tcaaatcatt gtttggagga   2340
atgtcctggt tctcacaaat tctcattgga acgttgctga tgtggttggg tctgaacaca   2400
aagaatggat ctatttccct tatgtgcttg gccttagggg gagtgttgat cttcttatcc   2460
acagccgtct ctgctgatgt ggggtgctcg gtggacttct caaagaagga gacgagatgc   2520
ggtacagggg tgttcgtcta taacgacgtt gaagcctgga gggacaggta caagtaccat   2580
```

```
cctgactccc cccgtagatt ggcagcagca gtcaagcaag cctgggaaga tggtatctgc    2640
gggatctcct ctgtttcaag aatggaaaac atcatgtgga gatcagtaga aggggagctc    2700
aacgcaatcc tggaagagaa tggagttcaa ctgacggtcg ttgtgggatc tgtaaaaaac    2760
cccatgtgga gaggtccaca gagattgccc gtgcctgtga acgagctgcc ccacggctgg    2820
aaggcttggg ggaaatcgta cttcgtcaga gcagcaaaga caaataacag ctttgtcgtg    2880
gatggtgaca cactgaagga atgcccactc aaacatagag catggaacag ctttcttgtg    2940
gaggatcatg ggttcggggt atttcacact agtgtctggc tcaaggttag agaagattat    3000
tcattagagt gtgatccagc cgttattgga acagctgtta agggaaagga ggctgtacac    3060
agtgatctag gctactggat tgagagtgag aagaatgaca catggaggct gaagagggcc    3120
catctgatcg agatgaaaac atgtgaatgg ccaaagtccc acacattgtg gacagatgga    3180
atagaagaga gtgatctgat catacccaag tctttagctg gccactcag ccatcacaat     3240 accagagagg gctacaggac ccaaatgaaa gggccatggc acagtgaaga gcttgaaatt    3300
cggtttgagg aatgcccagg cactaaggtc cacgtggagg aaacatgtgg aacaagagga    3360
ccatctctga gatcaaccac tgcaagcgga agggtgatcg aggaatggtg ctgcagggag    3420
tgcacaatgc ccccactgtc gttccgggct aaagatggct gttggtatgg aatggagata    3480
aggcccagga agaaccaga aagcaactta gtaaggtcaa tggtgactgc aggatcaact      3540
gatcacatgg accacttctc ccttggagtg cttgtgattc tgctcatggt gcaggaaggg    3600
ctgaagaaga gaatgaccac aaagatcatc ataagcacat caatggcagt gctggtagct    3660
atgatcctgg gaggatttc aatgagtgac ctggctaagc ttgcaatttt gatgggtgcc     3720
accttcgcgg aaatgaacac tggaggagat gtagctcatc tggcgctgat agcggcattc    3780
aaagtcagac cagcgttgct ggtatctttc atcttcagag ctaattggac ccccgtgaa     3840 agcatgctgc tggccttggc ctcgtgtctt ttgcaaactg cgatctccgc cttgaaggc     3900 gacctgatgg ttctcatcaa tggttttgct ttggcctggt tggcaatacg agcgatggtt    3960
gttccacgca ctgataacat caccttggca atcctggctg ctctgacacc actggcccgg    4020
ggcacactgc ttgtggcgtg gagagcaggc cttgctactt gcggggggtt tatgctcctc    4080
tctctgaagg gaaaaggcag tgtgaagaag aacttaccat tgtcatggc cctgggacta    4140 accgctgtga ggctggtcga ccccatcaac gtggtggac tgctgttgct cacaaggagt    4200
gggaagcgga gctggccccc tagcgaagta ctcacagctg ttggcctgat atgcgcattg    4260
gctggagggt tcgccaaggc agatatagag atggctgggc ccatgccgc ggtcggtctg    4320 ctaattgtca gttacgtggt ctcaggaaag agtgtggaca tgtacattga aagagcaggt    4380
gacatcacat gggaaaaaga tgcggaagtc actggaaaca gtccccggct cgatgtggcg    4440
ctagatgaga gtggtgattt ctccctggtg gaggatgacg gtccccccat gagagagatc    4500
atactcaagg tggtcctgat gaccatctgt ggcatgaacc caatagccat acccttttgca   4560 gctggagcgt ggtacgtata cgtgaagact ggaaaaagga gtggtgctct atgggatgtg    4620
cctgctccca aggaagtaaa aaaggggag accacagatg gagtgtacag agtaatgact    4680
cgtagactgc taggttcaac acaagttgga gtgggagtta tgcaagaggg ggtctttcac    4740
actatgtggc acgtcacaaa aggatccgcg ctgagaagcg gtgaagggag acttgatcca    4800
tactggggag atgtcaagca ggatctggtc tcatactgtg gtccatggaa gctagatgcc    4860
gcctgggacg ggcacagcga ggtgcagctc ttggccgtgc cccccggaga gagagcgagg    4920
```

```
aacatccaga ctctgcccgg aatatttaag acaaaggatg gggacattgg agcggttgcg      4980
ctggattacc cagcaggaac ttcaggatct ccaatcctag acaagtgtgg gagagtgata      5040
ggactttatg gcaatggggt cgtgatcaaa aatgggagtt atgttagtgc catcacccaa      5100
gggaggaggg aggaagagac tcctgttgag tgcttcgagc cttcgatgct gaagaagaag      5160
cagctaactg tcttagactt gcatcctgga gctgggaaaa ccaggagagt tcttcctgaa      5220
atagtccgtg aagccataaa acaagactc cgcaccgtga tcttagctcc aaccaggctt       5280
gtcgctgctg aaatggagga ggcccttaga gggcttccag tgcgttatat gacaacagca      5340
gtcaatgtca cccactctgg aacagaaatc gtcgacttaa tgtgccatgc cccttcact        5400
tcacgtctac tacagccaat cagagtcccc aactataatc tgtatattat ggatgaggcc      5460
cacttcacag atccctcaag tatagcagca agaggataca tttcaacaag ggttgagatg      5520
ggcgaggcgg ctgccatctt catgaccgcc acgccaccag gaacccgtga cgcatttccg      5580
gactccaact caccaattat ggacaccgaa gtggaagtcc cagagagagc ctggagctca      5640
ggctttgatt gggtgacgga tcattctgga aaaacagttt ggtttgttcc aagcgtgagg      5700
aacggcaatg agatcgcagc ttgtctgaca aaggctggaa aacgggtcat acagctcagc      5760
agaaagactt ttgagacaga gttccagaaa acaaaacatc aagagtggga ctttgtcgtg      5820
acaactgaca tttcagagat gggcgccaac tttaaagctg accgtgtcat agattccagg      5880
agatgcctaa agccggtcat acttgatggc gagagagtca ttctggctgg acccatgcct      5940
gtcacacatg ccagcgctgc ccagaggagg gggcgcatag gcaggaatcc caacaaacct      6000
ggagatgagt atctgtatgg aggtgggtgc gcagagactg acgaagacca tgcacactgg      6060
cttgaagcaa gaatgctcct tgacaatatt tacctccaag atggcctcat agcctcgctc      6120
tatcgacctg aggccgacaa agtagcagcc attgaggag agttcaagct taggacggag       6180
caaaggaaga cctttgtgga actcatgaaa agaggagatc ttcctgtttg gctggcctat      6240
caggttgcat ctgccggaat aacctacaca gatagaagat ggtgctttga tggcacgacc      6300
aacaacacca taatggaaga cagtgtgccg gcagaggtgt ggaccagaca cggagagaaa      6360
agagtgctca aaccgaggtg gatggacgcc agagtttgtt cagatcatgc ggccctgaag      6420
tcattcaagg agtttgccgc tgggaaaaga ggagcggctt ttggagtgat ggaagccctg      6480
ggaacactgc caggacacat gacagagaga ttccaggaag ccattgacaa cctcgctgtg      6540
ctcatgcggg cagagactgg aagcaggcct tacaaagccg cggcggccca attgccggag      6600
accctagaga ccattatgct tttggggttg ctgggaacag tctcgctggg aatcttcttc      6660
gtcttgatga ggaacaaggg catagggaag atgggctttg gaatggtgac tcttggggcc      6720
agcgcatggc tcatgtggct ctcggaaatt gagccagcca gaattgcatg tgtcctcatt      6780
gttgtgtttc tattgctggt ggtgctcata cctgagccag aaaagcaaag atctccccag      6840
gacaaccaaa tggcaatcat catcatggta gcagtaggtc ttctgggctt gattaccgcc      6900
aatgaactcg gatggttgga gagaacaaag agtgacctaa gccatctaat gggaaggaga      6960
gaggaggggg caaccatagg attctcaatg gacattgacc tgcggccagc ctcagcttgg      7020
gccatctatg ctgccttgac aactttcatt accccagccg tccaacatgc agtgaccact      7080
tcatacaaca actactcctt aatggcgatg gccacgcaag ctggagtgtt gtttggtatg      7140
ggcaaaggga tgccattcta cgcatgggac tttggagtcc cgctgctaat gataggttgc      7200
tactcacaat taacacccct gacctaata gtggccatca ttttgctcgt ggcgcactac       7260
atgtacttga tcccagggct gcaggcagca gctgcgcgtg ctgcccagaa gagaacggca      7320
```

```
gctggcatca tgaagaaccc tgttgtggat ggaatagtgg tgactgacat tgacacaatg    7380
acaattgacc cccaagtgga gaaaaagatg ggacaggtgc tactcatagc agtagccgtc    7440
tccagcgcca tactgtcgcg gaccgcctgg gggtggggg aggctgggc cctgatcaca      7500 gccgcaactt ccactttgtg ggaaggctct ccgaacaagt actggaactc ctctacagcc    7560
acttcactgt gtaacatttt taggggaagt tacttggctg gagcttctct aatctacaca    7620
gtaacaagaa acgctggctt ggtcaagaga cgtgggggtg gaacaggaga ccctggga      7680 gagaaatgga aggcccgctt gaaccagatg tcggccctgg agttctactc ctacaaaaag    7740
tcaggcatca ccgaggtgtg cagagaagag gcccgccgcg ccctcaagga cggtgtggca    7800
acgggaggcc atgctgtgtc ccgaggaagt gcaaagctga gatggttggt ggagcgggga    7860
tacctgcagc cctatggaaa ggtcattgat cttggatgtg gcagaggggg ctggagttac    7920
tacgccgcca ccatccgcaa agttcaagaa gtgaaggat acacaaaagg aggccctggt    7980
catgaagaac ccgtgttggt gcaaagctat gggtggaaca tagtccgtct taagagtggg    8040
gtggacgtct ttcatatggc ggctgagccg tgtgacacgt tgctgtgtga cataggtgag    8100
tcatcatcta gtcctgaagt ggaagaagca cggacgctca gagtcctctc catggtgggg    8160
gattggcttg aaaaaagacc aggagccttt tgtataaagg tgttgtgccc atacaccagc    8220
actatgatgg aaaccctgga gcgactgcag cgtaggtatg ggggaggact ggtcagagtg    8280
ccactctccc gcaactctac acatgagatg tattgggtct ctggagcgaa aagcaacacc    8340
ataaaaagtg tgtccaccac gagccagctc ctcttgggc gcatggacgg gcctaggagg    8400
ccagtgaaat atgaggagga tgtggatctc ggctctggcc cgcgggctgt ggtaagctgc    8460
gctgaagctc ccaacatgaa gatcattggt aaccgcattg aaaggatccg cagtgagcac    8520
gcggaaacgt ggttctttga cgagaaccac ccatatagga catgggctta ccatggaagc    8580
tatgaggccc ccacacaagg gtcagcgtcc tctctaataa acggggttgt caggctcctg    8640
tcaaacccct gggatgtggt gactggagtc acaggaatag ccatgaccga caccacaccg    8700
tatggtcagc aaagagtttt caaggaaaaa gtggacacta gggtgccaga ccccaagaa    8760 ggcactcgtc aggttatgag catggtctct tcctggttgt ggaaagagct aggcaaacac    8820
aaacggccac gagtctgtac caaagaagag ttcatcaaca aggttcgtag caatgcagca    8880 ttagggggcaa tatttgaaga ggaaaaagag tggaagactg cagtggaagc tgtgaacgat    8940
ccaaggttct gggctctagt ggataaggaa agagagcacc acctgagagg agagtgccag    9000
agttgtgtgt acaacatgat gggaaaaaga gaaaagaaac aaggggaatt tggaaaggcc    9060
aagggcagcc gcgccatctg gtatatgtgg ctaggggcta gatttctaga gttcgaagcc    9120
cttggattct tgaacgagga tcactggatg ggagagaga actcaggagg tggtgttgaa    9180
gggctgggat tacaaagact cggatatgtc ctagaagaga tgagtcgtat accaggagga    9240
aggatgtatg cagatgacac tgctggctgg gacacccgca tcagcaggtt tgatctggag    9300
aatgaagctc taatcaccaa ccaaatggaa aaagggcaca gggccttggc attggccata    9360
atcaagtaca cataccaaaa caagtggta aaggtcctta gaccagctga aaagggaaa    9420 acagttatgg acattatttc gagacaagac caaaggggga gcgacaagt tgtcacttac    9480 gctcttaaca catttaccaa cctagtggtg caactcattc ggaatatgga ggctgaggaa    9540
gttctagaga tgcaagactt gtggctgctg cggaggtcag agaaagtgac caactggttg    9600
cagagcaacg gatgggatag gctcaaacga atggcagtca gtggagatga ttgcgttgtg    9660
```

-continued

```
aagccaattg atgataggtt tgcacatgcc ctcaggttct tgaatgatat gggaaaagtt    9720
aggaaggaca cacaagagtg aaaccctca actggatggg acaactggga agaagttccg    9780
ttttgctccc accacttcaa caagctccat ctcaaggacg ggaggtccat tgtggttccc    9840
tgccgccacc aagatgaact gattggccgg gcccgcgtct ctccagggc gggatggagc     9900 atccgggaga ctgcttgcct agcaaaatca tatgcgcaaa tgtggcagct cctttatttc    9960
cacagaaggg acctccgact gatggccaat gccatttgtt catctgtgcc agttgactgg   10020
gttccaactg ggagaactac ctggtcaatc catggaaagg gagaatggat gaccactgaa   10080
gacatgcttg tggtgtggaa cagagtgtgg attgaggaga cgaccacat ggaagacaag    10140 accccagtta cgaaatggac agacattccc tatttgggaa aaagggaaga cttgtggtgt   10200
ggatctctca tagggcacag accgcgcacc acctgggctg agaacattaa aaacacagtc   10260
aacatggtgc gcaggatcat aggtgatgaa gaaaagtaca tggactacct atccacccaa   10320
gttcgctact tgggtgaaga agggtctaca cctggagtgc tgtaagcacc aatcttaatg   10380
ttgtcaggcc tgctagtcag ccacagcttg gggaaagctg tgcagcctgt gacccccag    10440 gagaagctgg gaaaccaagc ctatagtcag gccgagaacg ccatggcacg gaagaagcca   10500
tgctgcctgt gagcccctca gaggacactg agtcaaaaaa ccccacgcgc ttggaggcgc   10560
aggatgggaa agaaggtgg cgaccttccc cacccttcaa tctgggcct gaactggaga     10620 tcagctgtgg atctccagaa gagggactag tggttagagg ag                      10662
```

<210> SEQ ID NO 16
<211> LENGTH: 3423
<212> TYPE: PRT
<213> ORGANISM: Artificial Sequence
<220> FEATURE:
<223> OTHER INFORMATION: Synthetic construct

<400> SEQUENCE: 16

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
                100                 105                 110

Val Gly Leu Leu Leu Thr Thr Ala Met Ala Ala Glu Val Thr Arg Arg
            115                 120                 125

Gly Ser Ala Tyr Tyr Met Tyr Leu Asp Arg Asn Asp Ala Gly Glu Ala
        130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
                180                 185                 190
```

-continued

```
Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605
```

-continued

```
Ala Glu Thr Leu His Gly Thr Val Thr Val Glu Val Gln Tyr Ala Gly
610             615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
            645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
755                 760                 765

Thr Lys Asn Gly Ser Ile Ser Leu Met Cys Leu Ala Leu Gly Gly Val
770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
            835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
```

```
                 1025                1030                1035

Lys Ser Leu Ala Gly Pro Leu Ser His His Asn Thr Arg Glu Gly
        1040                1045                1050

Tyr Arg Thr Gln Met Lys Gly Pro Trp His Ser Glu Glu Leu Glu
        1055                1060                1065

Ile Arg Phe Glu Glu Cys Pro Gly Thr Lys Val His Val Glu Glu
        1070                1075                1080

Thr Cys Gly Thr Arg Gly Pro Ser Leu Arg Ser Thr Thr Ala Ser
        1085                1090                1095

Gly Arg Val Ile Glu Glu Trp Cys Cys Arg Glu Cys Thr Met Pro
        1100                1105                1110

Pro Leu Ser Phe Arg Ala Lys Asp Gly Cys Trp Tyr Gly Met Glu
        1115                1120                1125

Ile Arg Pro Arg Lys Glu Pro Glu Ser Asn Leu Val Arg Ser Met
        1130                1135                1140

Val Thr Ala Gly Ser Thr Asp His Met Asp His Phe Ser Leu Gly
        1145                1150                1155

Val Leu Val Ile Leu Leu Met Val Gln Glu Gly Leu Lys Lys Arg
        1160                1165                1170

Met Thr Thr Lys Ile Ile Ile Ser Thr Ser Met Ala Val Leu Val
        1175                1180                1185

Ala Met Ile Leu Gly Gly Phe Ser Met Ser Asp Leu Ala Lys Leu
        1190                1195                1200

Ala Ile Leu Met Gly Ala Thr Phe Ala Glu Met Asn Thr Gly Gly
        1205                1210                1215

Asp Val Ala His Leu Ala Leu Ile Ala Ala Phe Lys Val Arg Pro
        1220                1225                1230

Ala Leu Leu Val Ser Phe Ile Phe Arg Ala Asn Trp Thr Pro Arg
        1235                1240                1245

Glu Ser Met Leu Leu Ala Leu Ala Ser Cys Leu Leu Gln Thr Ala
        1250                1255                1260

Ile Ser Ala Leu Glu Gly Asp Leu Met Val Leu Ile Asn Gly Phe
        1265                1270                1275

Ala Leu Ala Trp Leu Ala Ile Arg Ala Met Val Val Pro Arg Thr
        1280                1285                1290

Asp Asn Ile Thr Leu Ala Ile Leu Ala Ala Leu Thr Pro Leu Ala
        1295                1300                1305

Arg Gly Thr Leu Leu Val Ala Trp Arg Ala Gly Leu Ala Thr Cys
        1310                1315                1320

Gly Gly Phe Met Leu Leu Ser Leu Lys Gly Lys Gly Ser Val Lys
        1325                1330                1335

Lys Asn Leu Pro Phe Val Met Ala Leu Gly Leu Thr Ala Val Arg
        1340                1345                1350

Leu Val Asp Pro Ile Asn Val Val Gly Leu Leu Leu Leu Thr Arg
        1355                1360                1365

Ser Gly Lys Arg Ser Trp Pro Pro Ser Glu Val Leu Thr Ala Val
        1370                1375                1380

Gly Leu Ile Cys Ala Leu Ala Gly Gly Phe Ala Lys Ala Asp Ile
        1385                1390                1395

Glu Met Ala Gly Pro Met Ala Ala Val Gly Leu Leu Ile Val Ser
        1400                1405                1410

Tyr Val Val Ser Gly Lys Ser Val Asp Met Tyr Ile Glu Arg Ala
        1415                1420                1425
```

Gly Asp Ile Thr Trp Glu Lys Asp Ala Glu Val Thr Gly Asn Ser
1430                1435                1440

Pro Arg Leu Asp Val Ala Leu Asp Glu Ser Gly Asp Phe Ser Leu
1445                1450                1455

Val Glu Asp Asp Gly Pro Pro Met Arg Glu Ile Ile Leu Lys Val
1460                1465                1470

Val Leu Met Thr Ile Cys Gly Met Asn Pro Ile Ala Ile Pro Phe
1475                1480                1485

Ala Ala Gly Ala Trp Tyr Val Tyr Val Lys Thr Gly Lys Arg Ser
1490                1495                1500

Gly Ala Leu Trp Asp Val Pro Ala Pro Lys Glu Val Lys Lys Gly
1505                1510                1515

Glu Thr Thr Asp Gly Val Tyr Arg Val Met Thr Arg Arg Leu Leu
1520                1525                1530

Gly Ser Thr Gln Val Gly Val Gly Val Met Gln Glu Gly Val Phe
1535                1540                1545

His Thr Met Trp His Val Thr Lys Gly Ser Ala Leu Arg Ser Gly
1550                1555                1560

Glu Gly Arg Leu Asp Pro Tyr Trp Gly Asp Val Lys Gln Asp Leu
1565                1570                1575

Val Ser Tyr Cys Gly Pro Trp Lys Leu Asp Ala Ala Trp Asp Gly
1580                1585                1590

His Ser Glu Val Gln Leu Leu Ala Val Pro Pro Gly Glu Arg Ala
1595                1600                1605

Arg Asn Ile Gln Thr Leu Pro Gly Ile Phe Lys Thr Lys Asp Gly
1610                1615                1620

Asp Ile Gly Ala Val Ala Leu Asp Tyr Pro Ala Gly Thr Ser Gly
1625                1630                1635

Ser Pro Ile Leu Asp Lys Cys Gly Arg Val Ile Gly Leu Tyr Gly
1640                1645                1650

Asn Gly Val Val Ile Lys Asn Gly Ser Tyr Val Ser Ala Ile Thr
1655                1660                1665

Gln Gly Arg Arg Glu Glu Glu Thr Pro Val Glu Cys Phe Glu Pro
1670                1675                1680

Ser Met Leu Lys Lys Lys Gln Leu Thr Val Leu Asp Leu His Pro
1685                1690                1695

Gly Ala Gly Lys Thr Arg Arg Val Leu Pro Glu Ile Val Arg Glu
1700                1705                1710

Ala Ile Lys Thr Arg Leu Arg Thr Val Ile Leu Ala Pro Thr Arg
1715                1720                1725

Val Val Ala Ala Glu Met Glu Glu Ala Leu Arg Gly Leu Pro Val
1730                1735                1740

Arg Tyr Met Thr Thr Ala Val Asn Val Thr His Ser Gly Thr Glu
1745                1750                1755

Ile Val Asp Leu Met Cys His Ala Thr Phe Thr Ser Arg Leu Leu
1760                1765                1770

Gln Pro Ile Arg Val Pro Asn Tyr Asn Leu Tyr Ile Met Asp Glu
1775                1780                1785

Ala His Phe Thr Asp Pro Ser Ser Ile Ala Ala Arg Gly Tyr Ile
1790                1795                1800

Ser Thr Arg Val Glu Met Gly Glu Ala Ala Ile Phe Met Thr
1805                1810                1815

```
Ala Thr Pro Pro Gly Thr Arg Asp Ala Phe Pro Asp Ser Asn Ser
    1820            1825            1830

Pro Ile Met Asp Thr Glu Val Glu Val Pro Glu Arg Ala Trp Ser
    1835            1840            1845

Ser Gly Phe Asp Trp Val Thr Asp His Ser Gly Lys Thr Val Trp
    1850            1855            1860

Phe Val Pro Ser Val Arg Asn Gly Asn Glu Ile Ala Ala Cys Leu
    1865            1870            1875

Thr Lys Ala Gly Lys Arg Val Ile Gln Leu Ser Arg Lys Thr Phe
    1880            1885            1890

Glu Thr Glu Phe Gln Lys Thr Lys His Gln Glu Trp Asp Phe Val
    1895            1900            1905

Val Thr Thr Asp Ile Ser Glu Met Gly Ala Asn Phe Lys Ala Asp
    1910            1915            1920

Arg Val Ile Asp Ser Arg Arg Cys Leu Lys Pro Val Ile Leu Asp
    1925            1930            1935

Gly Glu Arg Val Ile Leu Ala Gly Pro Met Pro Val Thr His Ala
    1940            1945            1950

Ser Ala Ala Gln Arg Arg Gly Arg Ile Gly Arg Asn Pro Asn Lys
    1955            1960            1965

Pro Gly Asp Glu Tyr Leu Tyr Gly Gly Gly Cys Ala Glu Thr Asp
    1970            1975            1980

Glu Asp His Ala His Trp Leu Glu Ala Arg Met Leu Leu Asp Asn
    1985            1990            1995

Ile Tyr Leu Gln Asp Gly Leu Ile Ala Ser Leu Tyr Arg Pro Glu
    2000            2005            2010

Ala Asp Lys Val Ala Ala Ile Glu Gly Glu Phe Lys Leu Arg Thr
    2015            2020            2025

Glu Gln Arg Lys Thr Phe Val Glu Leu Met Lys Arg Gly Asp Leu
    2030            2035            2040

Pro Val Trp Leu Ala Tyr Gln Val Ala Ser Ala Gly Ile Thr Tyr
    2045            2050            2055

Thr Asp Arg Arg Trp Cys Phe Asp Gly Thr Thr Asn Asn Thr Ile
    2060            2065            2070

Met Glu Asp Ser Val Pro Ala Glu Val Trp Thr Arg His Gly Glu
    2075            2080            2085

Lys Arg Val Leu Lys Pro Arg Trp Met Asp Ala Arg Val Cys Ser
    2090            2095            2100

Asp His Ala Ala Leu Lys Ser Phe Lys Glu Phe Ala Ala Gly Lys
    2105            2110            2115

Arg Gly Ala Ala Phe Gly Val Met Glu Ala Leu Gly Thr Leu Pro
    2120            2125            2130

Gly His Met Thr Glu Arg Phe Gln Glu Ala Ile Asp Asn Leu Ala
    2135            2140            2145

Val Leu Met Arg Ala Glu Thr Gly Ser Arg Pro Tyr Lys Ala Ala
    2150            2155            2160

Ala Ala Gln Leu Pro Glu Thr Leu Glu Thr Ile Met Leu Leu Gly
    2165            2170            2175

Leu Leu Gly Thr Val Ser Leu Gly Ile Phe Phe Val Leu Met Arg
    2180            2185            2190

Asn Lys Gly Ile Gly Lys Met Gly Phe Gly Met Val Thr Leu Gly
    2195            2200            2205

Ala Ser Ala Trp Leu Met Trp Leu Ser Glu Ile Glu Pro Ala Arg
```

-continued

```
            2210                2215                2220
Ile Ala Cys Val Leu Ile Val Val Phe Leu Leu Val Val Leu
    2225                2230                2235
Ile Pro Glu Pro Glu Lys Gln Arg Ser Pro Gln Asp Asn Gln Met
    2240                2245                2250
Ala Ile Ile Ile Met Val Ala Val Gly Leu Leu Gly Leu Ile Thr
    2255                2260                2265
Ala Asn Glu Leu Gly Trp Leu Glu Arg Thr Lys Ser Asp Leu Ser
    2270                2275                2280
His Leu Met Gly Arg Arg Glu Glu Gly Ala Thr Ile Gly Phe Ser
    2285                2290                2295
Met Asp Ile Asp Leu Arg Pro Ala Ser Ala Trp Ala Ile Tyr Ala
    2300                2305                2310
Ala Leu Thr Thr Phe Ile Thr Pro Ala Val Gln His Ala Val Thr
    2315                2320                2325
Thr Ser Tyr Asn Asn Tyr Ser Leu Met Ala Met Ala Thr Gln Ala
    2330                2335                2340
Gly Val Leu Phe Gly Met Gly Lys Gly Met Pro Phe Tyr Ala Trp
    2345                2350                2355
Asp Phe Gly Val Pro Leu Leu Met Ile Gly Cys Tyr Ser Gln Leu
    2360                2365                2370
Thr Pro Leu Thr Leu Ile Val Ala Ile Ile Leu Leu Val Ala His
    2375                2380                2385
Tyr Met Tyr Leu Ile Pro Gly Leu Gln Ala Ala Ala Ala Arg Ala
    2390                2395                2400
Ala Gln Lys Arg Thr Ala Ala Gly Ile Met Lys Asn Pro Val Val
    2405                2410                2415
Asp Gly Ile Val Val Thr Asp Ile Asp Thr Met Thr Ile Asp Pro
    2420                2425                2430
Gln Val Glu Lys Lys Met Gly Gln Val Leu Leu Ile Ala Val Ala
    2435                2440                2445
Val Ser Ser Ala Ile Leu Ser Arg Thr Ala Trp Gly Trp Gly Glu
    2450                2455                2460
Ala Gly Ala Leu Ile Thr Ala Ala Thr Ser Thr Leu Trp Glu Gly
    2465                2470                2475
Ser Pro Asn Lys Tyr Trp Asn Ser Ser Thr Ala Thr Ser Leu Cys
    2480                2485                2490
Asn Ile Phe Arg Gly Ser Tyr Leu Ala Gly Ala Ser Leu Ile Tyr
    2495                2500                2505
Thr Val Thr Arg Asn Ala Gly Leu Val Lys Arg Arg Gly Gly Gly
    2510                2515                2520
Thr Gly Glu Thr Leu Gly Glu Lys Trp Lys Ala Arg Leu Asn Gln
    2525                2530                2535
Met Ser Ala Leu Glu Phe Tyr Ser Tyr Lys Lys Ser Gly Ile Thr
    2540                2545                2550
Glu Val Cys Arg Glu Glu Ala Arg Arg Ala Leu Lys Asp Gly Val
    2555                2560                2565
Ala Thr Gly Gly His Ala Val Ser Arg Gly Ser Ala Lys Leu Arg
    2570                2575                2580
Trp Leu Val Glu Arg Gly Tyr Leu Gln Pro Tyr Gly Lys Val Ile
    2585                2590                2595
Asp Leu Gly Cys Gly Arg Gly Gly Trp Ser Tyr Tyr Ala Ala Thr
    2600                2605                2610
```

```
Ile Arg Lys Val Gln Glu Val Lys Gly Tyr Thr Lys Gly Gly Pro
2615                 2620                2625

Gly His Glu Glu Pro Val Leu Val Gln Ser Tyr Gly Trp Asn Ile
2630                 2635                2640

Val Arg Leu Lys Ser Gly Val Asp Val Phe His Met Ala Ala Glu
2645                 2650                2655

Pro Cys Asp Thr Leu Leu Cys Asp Ile Gly Glu Ser Ser Ser Ser
2660                 2665                2670

Pro Glu Val Glu Glu Ala Arg Thr Leu Arg Val Leu Ser Met Val
2675                 2680                2685

Gly Asp Trp Leu Glu Lys Arg Pro Gly Ala Phe Cys Ile Lys Val
2690                 2695                2700

Leu Cys Pro Tyr Thr Ser Thr Met Met Glu Thr Leu Glu Arg Leu
2705                 2710                2715

Gln Arg Arg Tyr Gly Gly Gly Leu Val Arg Val Pro Leu Ser Arg
2720                 2725                2730

Asn Ser Thr His Glu Met Tyr Trp Val Ser Gly Ala Lys Ser Asn
2735                 2740                2745

Thr Ile Lys Ser Val Ser Thr Thr Ser Gln Leu Leu Leu Gly Arg
2750                 2755                2760

Met Asp Gly Pro Arg Arg Pro Val Lys Tyr Glu Glu Asp Val Asp
2765                 2770                2775

Leu Gly Ser Gly Thr Arg Ala Val Val Ser Cys Ala Glu Ala Pro
2780                 2785                2790

Asn Met Lys Ile Ile Gly Asn Arg Ile Glu Arg Ile Arg Ser Glu
2795                 2800                2805

His Ala Glu Thr Trp Phe Phe Asp Glu Asn His Pro Tyr Arg Thr
2810                 2815                2820

Trp Ala Tyr His Gly Ser Tyr Glu Ala Pro Thr Gln Gly Ser Ala
2825                 2830                2835

Ser Ser Leu Ile Asn Gly Val Val Arg Leu Leu Ser Lys Pro Trp
2840                 2845                2850

Asp Val Val Thr Gly Val Thr Gly Ile Ala Met Thr Asp Thr Thr
2855                 2860                2865

Pro Tyr Gly Gln Gln Arg Val Phe Lys Glu Lys Val Asp Thr Arg
2870                 2875                2880

Val Pro Asp Pro Gln Glu Gly Thr Arg Gln Val Met Ser Met Val
2885                 2890                2895

Ser Ser Trp Leu Trp Lys Glu Leu Gly Lys His Lys Arg Pro Arg
2900                 2905                2910

Val Cys Thr Lys Glu Glu Phe Ile Asn Lys Val Arg Ser Asn Ala
2915                 2920                2925

Ala Leu Gly Ala Ile Phe Glu Glu Glu Lys Glu Trp Lys Thr Ala
2930                 2935                2940

Val Glu Ala Val Asn Asp Pro Arg Phe Trp Ala Leu Val Asp Lys
2945                 2950                2955

Glu Arg Glu His His Leu Arg Gly Glu Cys Gln Ser Cys Val Tyr
2960                 2965                2970

Asn Met Met Gly Lys Arg Glu Lys Lys Gln Gly Glu Phe Gly Lys
2975                 2980                2985

Ala Lys Gly Ser Arg Ala Ile Trp Tyr Met Trp Leu Gly Ala Arg
2990                 2995                3000
```

Phe Leu Glu Phe Glu Ala Leu Gly Phe Leu Asn Glu Asp His Trp
3005                3010                3015

Met Gly Arg Glu Asn Ser Gly Gly Val Glu Gly Leu Gly Leu
3020                3025                3030

Gln Arg Leu Gly Tyr Val Leu Glu Glu Met Ser Arg Ile Pro Gly
3035                3040                3045

Gly Arg Met Tyr Ala Asp Asp Thr Ala Gly Trp Asp Thr Arg Ile
3050                3055                3060

Ser Arg Phe Asp Leu Glu Asn Glu Ala Leu Ile Thr Asn Gln Met
3065                3070                3075

Glu Lys Gly His Arg Ala Leu Ala Leu Ala Ile Ile Lys Tyr Thr
3080                3085                3090

Tyr Gln Asn Lys Val Val Lys Val Leu Arg Pro Ala Glu Lys Gly
3095                3100                3105

Lys Thr Val Met Asp Ile Ile Ser Arg Gln Asp Gln Arg Gly Ser
3110                3115                3120

Gly Gln Val Val Thr Tyr Ala Leu Asn Thr Phe Thr Asn Leu Val
3125                3130                3135

Val Gln Leu Ile Arg Asn Met Glu Ala Glu Glu Val Leu Glu Met
3140                3145                3150

Gln Asp Leu Trp Leu Leu Arg Arg Ser Glu Lys Val Thr Asn Trp
3155                3160                3165

Leu Gln Ser Asn Gly Trp Asp Arg Leu Lys Arg Met Ala Val Ser
3170                3175                3180

Gly Asp Asp Cys Val Val Lys Pro Ile Asp Asp Arg Phe Ala His
3185                3190                3195

Ala Leu Arg Phe Leu Asn Asp Met Gly Lys Val Arg Lys Asp Thr
3200                3205                3210

Gln Glu Trp Lys Pro Ser Thr Gly Trp Asp Asn Trp Glu Glu Val
3215                3220                3225

Pro Phe Cys Ser His His Phe Asn Lys Leu His Leu Lys Asp Gly
3230                3235                3240

Arg Ser Ile Val Val Pro Cys Arg His Gln Asp Glu Leu Ile Gly
3245                3250                3255

Arg Ala Arg Val Ser Pro Gly Ala Gly Trp Ser Ile Arg Glu Thr
3260                3265                3270

Ala Cys Leu Ala Lys Ser Tyr Ala Gln Met Trp Gln Leu Leu Tyr
3275                3280                3285

Phe His Arg Arg Asp Leu Arg Leu Met Ala Asn Ala Ile Cys Ser
3290                3295                3300

Ser Val Pro Val Asp Trp Val Pro Thr Gly Arg Thr Thr Trp Ser
3305                3310                3315

Ile His Gly Lys Gly Glu Trp Met Thr Thr Glu Asp Met Leu Val
3320                3325                3330

Val Trp Asn Arg Val Trp Ile Glu Glu Asn Asp His Met Glu Asp
3335                3340                3345

Lys Thr Pro Val Thr Lys Trp Thr Asp Ile Pro Tyr Leu Gly Lys
3350                3355                3360

Arg Glu Asp Leu Trp Cys Gly Ser Leu Ile Gly His Arg Pro Arg
3365                3370                3375

Thr Thr Trp Ala Glu Asn Ile Lys Asn Thr Val Asn Met Val Arg
3380                3385                3390

Arg Ile Ile Gly Asp Glu Glu Lys Tyr Met Asp Tyr Leu Ser Thr

```
                3395                3400                3405
Gln  Val  Arg  Tyr  Leu  Gly  Glu  Glu  Gly  Ser  Thr  Pro  Gly  Val  Leu
      3410                3415                3420

<210> SEQ ID NO 17
<211> LENGTH: 10793
<212> TYPE: DNA
<213> ORGANISM: Artificial Sequence
<220> FEATURE:
<223> OTHER INFORMATION: Synthetic construct

<400> SEQUENCE: 17
ccaatctgtg aatcagactg cgacagttcg agtttgaagc gaaagctagc aacagtatca     60
acaggtttta ttttggattt ggaaacgaga gtttctggtc atgaaaaacc caaaaagaa    120
atccggagga ttccggattg tcaatatgct aaaacgcgga gtagcccgtg tgagcccctt    180
tgggggcttg aagaggctgc agccggact tctgctgggt catgggccca tcaggatggt    240
cttggcgatt ctagcctttt tgagattcac ggcaatcaag ccatcactgg gtctcatcaa    300
tagatggggt tcagtgggga aaaagaggc tatggaaata taaagaagt tcaagaaaga    360
tctggctgcc atgctgagaa taatcaatgc caggaaggag aagaagagac gaggcgcaga    420
tactagtgtc ggaatcgttg gcctcctgct gaccacagct atggcagcgg aggtcactag    480
acgtgggagt gcatactata tgtacttgga cagaaacgat gctggggagg ccatatcttt    540
tccaaccaca ttggggatga ataagtgtta tatacagatc atggatcttg acacatgtg    600
tgatgccacc atgagctatg aatgccctat gctggatgag ggggtggaac cagatgacgt    660
cgattgttgg tgcaacacga cgtcaacttg ggttgtgtac ggaacctgcc atcacaaaaa    720
aggtgaagca cggagatcta aagagctgt gacgctcccc tcccattcca ctaggaagct    780
gcaaacgcgg tcgcaaacct ggttggaatc aagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caataggga tttgtggaag gtatgtcagg   1020
tgggacttgg gttgatgttg tcttggaaca tggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg acagccgct gcccaacaca   1200
aggtgaagcc taccttgaca agcaatcaga cactcaatat gtctgcaaaa gaacgttagt   1260
ggacagaggc tggggaaatg gatgtggact ttttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500
agccaccctg ggggttttg aagcttagg acttgattgt gaaccgagga caggccttga   1560
cttttcagat ttgtattact tgactatgaa taacaagcac tggttggttc acaaggagtg   1620
gttccacgac attccattac cttggcacgc tgggcagac accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aatggataaa   1860
acttagattg aagggcgtgt catactccct tgtgtaccgc agcgttcacat tcaccaagat   1920
```

```
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca ttgggcaagg gcatccatca aattttggga gcagctttca aatcattgtt   2340
tggaggaatg tcctggttct cacaaattct cattggaacg ttgctgatgt ggttgggtct   2400
gaacacaaag aatggatcta tttcccttat gtgcttggcc ttaggggagt gttgatctt    2460 cttatccaca gccgtctctg ctgatgtggg gtgctcggtg gacttctcaa gaaggagac    2520 gagatgtggt acagggtgt tcgtctataa cgacgttgaa gcctggaggg acaggtacaa    2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgccccca  2820 cggctggaag gcttggggga atcgtactt cgtcagagca gcaaagacaa ataacagctt    2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg aaaggaggc    3060 tgtacacagt gatctaggct actggattga gagtgagaag aatgacacat ggaggctgaa   3120
gagggcccat ctgatcgaga tgaaaacatg tgaatggcca aagtcccaca cattgtggac   3180
agatggaata gaagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgttttttg caaactgcga tctccgcctt   3900
ggaaggcgac ctgatggttc tcatcaatgg ttttgctttg gcctggttgg caatacgagc   3960
gatggttgtt ccacgcactg acaacatcac cttggcaatc ctggctgctc tgacaccact   4020
ggcccggggc acactgcttg tggcgtggag agcaggcctt gctacttgcg ggggtttat    4080 gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
cgcattggct ggagggttcg ccaaggcaga tatagagatg gctgggccca tggccgcggt   4320
```

```
cggtctgcta attgtcagtt acgtggtctc aggaaagagt gtggacatgt acattgaaag    4380
agcaggtgac atcacatggg aaaaagatgc ggaagtcact ggaaacagtc cccggctcga    4440
tgtggcgcta gatgagagtg gtgacttctc cctggtggag gatgacggtc cccccatgag    4500
agagatcata ctcaaggtgg tcctgatgac catctgtggc atgaacccaa tagccatacc    4560
ctttgcagct ggagcgtggt acgtatacgt gaagactgga aaaggagtg gtgctctatg     4620 ggatgtgcct gctcccaagg aagtaaaaaa gggggagacc acagatggag tgtacagagt    4680
aatgactcgt agactgctag gttcaacaca agttggagtg ggagttatgc aagagggggt    4740 cttttcacact atgtggcacg tcacaaaagg atccgcgctg agaagcggtg aagggagact    4800
tgatccatac tggggagatg tcaagcagga tctggtgtca tactgtggtc catggaagct    4860
agatgccgcc tgggacgggc acagcgaggt gcagctcttg gccgtgcccc ccggagagag    4920
agcgaggaac atccagactc tgcccggaat atttaagaca aaggatgggg acattggagc    4980
ggttgcgctg gattacccag caggaacttc aggatctcca atcctagaca agtgtgggag    5040
agtgatagga ctttatggca atggggtcgt gataaaaaat gggagttatg ttagtgccat    5100
cacccaaggg aggagggagg aagagactcc tgttgagtgc ttcgagcctt cgatgctgaa    5160
gaagaagcag ctaactgtct tagacttgca tcctggagct gggaaaacca ggagagttct    5220
tcctgaaata gtccgtgaag ccataaaaac aagactccgt actgtgatct tagctccaac    5280
cagggttgtc gctgctgaaa tggaggaagc ccttagaggg cttccagtgc gttatatgac    5340
aacagcagtc aatgtcaccc actctggaac agaaatcgtc gacttaatgt gccatgccac    5400
cttcacttca cgtctactac agccaatcag agtccccaac tataatctgt atattatgga    5460
tgaggcccac ttcacagatc cctcaagcat agcagcaaga ggatacattt caacaagggt    5520
tgagatgggc gaggcggctg ccatcttcat gaccgccacg ccaccaggaa cccgtgacgc    5580
atttccggac tccaactcac caattatgga caccgaagtg gaagtcccag agagagcctg    5640
gagctcaggc tttgattggg tgacggatca ttctggaaaa acagtttggt tgttccaag    5700 cgtgaggaac ggcaatgaga tcgcagcttg tctgacaaag gctggaaaac gggtcataca    5760
gctcagcaga aagacttttg agacagagtt ccagaaaaca aacatcaag agtgggactt    5820 tgtcgtgaca actgacattt cagagatggg cgccaacttt aaagctgacc gtgtcataga    5880
ttccaggaga tgcctaaagc cggtcatact tgatggcgag agagtcattc tggctggacc    5940
catgcctgtc acacatgcca gcgctgccca gaggaggggg cgcataggca ggaatcccaa    6000
caaacctgga gatgagtacc tgtatggagg tgggtgcgca gagactgacg aagaccatgc    6060
acactggctt gaagcaagaa tgctccttga caatatttac ctccaagatg gcctcatagc    6120
ctcgctctat cgacctgagg ccgacaaagt agcagccatt gagggagagt tcaagcttag    6180
gacggagcaa aggaagacct tgtggaact catgaaaaga ggagatcttc ctgtttggct    6240
ggcctatcag gttgcatctg ccggaataac ctacacagat agaagatggt gctttgatgg    6300
cacgaccaac aacaccataa tggaagacag tgtgccggca gaggtgtgga ccagacacgg    6360
agagaaaaga gtgctcaaac cgaggtggat ggacgccaga gtttgttcag atcatgcggc    6420
cctgaagtca ttcaaggagt ttgccgctgg gaaaagagga gcggcttttg gagtgatgga    6480
agccctggga acactgccag acacatgac agagagattc caggaagcca ttgacaacct    6540
cgctgtgctc atgcgggcag agactggaag caggccttac aaagccgcgg cggcccaatt    6600
gccggagacc ctagagacca ttatgctttt ggggttgctg ggaacagtct cgctgggaat    6660
```

```
cttttttcgtc ttgatgagga acaagggcat agggaagatg ggctttggaa tggtgactct    6720
tggggccagc gcatggctca tgtggctctc ggaaattgag ccagccagaa ttgcatgtgt    6780
cctcattgtt gtgttcctat tgctggtggt gctcatacct gagccagaaa agcaaagatc    6840
tccccaggac aaccaaatgg caatcatcat catggtagca gtaggtcttc tgggcttgat    6900
taccgccaat gaactcggat ggttggagag aacaaagagt gacctaagcc atctaatggg    6960
aaggagagag gaggggggcaa ccataggatt ctcaatggac attgacctgc ggccagcctc    7020
agcttgggcc atctatgctg ccttgacaac tttcattacc ccagccgtcc aacatgcagt    7080
gaccacttca tacaacaact actccttaat ggcgatggcc acgcaagctg gagtgttgtt    7140
tggtatgggc aaagggatgc cattctacgc atgggacttt ggagtcccgc tgctaatgat    7200
aggttgctac tcacaattaa caccccctgac cctaatagtg ccatcatttt gctcgtggc    7260
gcactacatg tacttgatcc cagggctgca ggcagcagct gcgcgtgctg cccagaagag    7320
aacggcagct ggcatcatga agaaccctgt tgtggatgga atagtggtga ctgacattga    7380
cacaatgaca attgaccccc aagtggagaa aaagatggga caggtgctac tcatagcagt    7440
agccgtctcc agcgccatac tgtcgcggac cgcctggggg tgggggagg ctggggccct    7500
gatcacagcc gcaacttcca cttttgtggga aggctctccg aacaagtact ggaactcctc    7560
tacagccact tcactgtgta acatttttag gggaagttac ttggctggag cttctctaat    7620
ctacacagta acaagaaacg ctggcttggt caagagacgt ggggggtggaa caggagagac    7680
cctgggagag aaatggaagg cccgcttgaa ccagatgtcg gccctggagt tctactccta    7740
caaaaagtca ggcatcaccg aggtgtgcag agaagaggcc cgccgcgccc tcaaggacgg    7800
tgtggcaacg ggaggccatg ctgtgtcccg aggaagtgca aagctgagat ggttggtgga    7860
gcggggatac ctgcagccct atggaaaggt cattgatctt ggatgtggca gaggggctg    7920
gagttactac gccgccacca tccgcaaagt tcaagaagtg aaaggataca caaaaggagg    7980
ccctggtcat gaagaacccg tgttggtgca aagctatggg tggaacatag tccgtcttaa    8040
gagtggggtg gacgtctttc atatggcggc tgagccgtgt gacacgttgc tgtgtgacat    8100
aggtgagtca tcatctagtc ctgaagtgga agaagcacgg acgctcagag tcctctccat    8160
ggtgggggat tggcttgaaa aaagaccagg agcctttgc ataaaagtgt tgtgcccata    8220
caccagcact atgatggaaa ccctggagcg actgcagcgt aggtatgggg gaggactggt    8280
cagagtgcca ctctcccgca actctacaca tgagatgtac tgggtctctg gagcgaaaag    8340
caacaccata aaaagtgtgt ccaccacgag ccagctcctc ttggggcgca tggacgggcc    8400
taggaggcca gtgaaatatg aggaggatgt gaatctcggc tctggcacgc gggctgtggt    8460
aagctgcgct gaagctccca catgaagat cattggtaac cgcattgaaa ggatccgcag    8520
tgagcacgcg gaaacgtggt tctttgacga aaaccaccca tataggacat gggcttacca    8580
tggaagctat gtggcccca cacaagggtc agcgtcctct ctaataaacg ggttgtcag    8640
gctcctgtca aaaccctggg atgtggtgac tggagtcaca ggaatagcca tgaccgacac    8700
cacaccgtat ggtcagcaaa gagttttcaa ggaaaaagtg acactaggg tgccagaccc    8760
ccaagaaggc actcgtcagg ttatgagcat ggtctcttcc tggttgtgga aagagctagg    8820
caaacacaaa cgaccacgag tctgtaccaa agaagagttc atcaacaagg ttcgtagcaa    8880
tgcagcatta gggcaatat ttgaagagga aaaagagtgg aagactgcag tggaagctgt    8940
gaacgatcca aggttctggg ctctagtgga caaggaaaga gagcaccacc tgagaggaga    9000
gtgccagagt tgtgtgtaca acatgatggg aaaaagagaa aagaaacaag gggaatttgg    9060
```

```
aaaggccaag ggcagccgcg ccatctggta tatgtggcta ggggctagat ttctagagtt    9120
cgaagccctt ggattcttga acgaggatca ctggatgggg agagagaact caggaggtgg    9180
tgttgaaggg ctgggattac aaagactcgg atatgtccta aagagatga gtcgcatacc     9240 aggaggaagg atgtatgcag atgacactgc tggctgggac acccgcatca gcaggtttga    9300
tctggagaat gaagctctaa tcaccaacca aatggagaaa gggcacaggg ccttggcatt    9360
ggccataatc aagtacacat accaaaacaa agtggtaaag gtccttagac cagctgaaaa    9420
agggaaaaca gttatggaca ttatttcgag acaagaccaa aggggagcg gacaagttgt     9480 cacttacgct cttaacacat ttccaacct agtggtgcaa ctcattcgga atatggaggc     9540
tgaggaagtt ctagagatgc aagacttgtg gctgctgcgg aggtcagaga agtgaccaa     9600 ctggttgcag agcaacggat gggataggct caaacgaatg gcagtcagtg agatgattg     9660 cgttgtgaag ccaattgatg ataggtttgc acatgccctc aggttcttga atgatatggg    9720
aaaagttagg aaggacacac aagagtggaa accctcaact ggatgggaca actgggaaga    9780
agttccgttt tgctcccacc acttcaacaa gctccatctc aaggacggga ggtccattgt    9840
ggttccctgc cgccaccaag atgaactgat tggccgggcc cgcgtctctc caggggcggg    9900
atggagcatc cgggagactg cttgcctagc aaaatcatat gcgcaaatgt ggcagctcct    9960
ttatttccac agaagggacc tccgactgat ggccaatgcc atttgttcat ctgtgccagt    10020
tgactgggtt ccaactggga gaactacctg gtcaatccat ggaaagggag aatggatgac    10080
cactgaagac atgcttgtgg tgtggaacag agtgtggatt gaggagaacg accacatgga    10140
agacaagacc ccagttacga aatggacaga cattccctat ttgggaaaaa gggaagactt    10200
gtggtgtgga tctctcatag gcacagacc gcgcaccacc tggctgaga acattaaaaa      10260 tacagtcaac atggtgcgca ggatcatagg tgatgaagaa aagtacatgg actacctatc    10320
cacccaagtt cgctacttgg gtgaagaagg gtctacacct ggagtgctgt gagcaccaat    10380
cttaatgttg tcaggcctgc tagtcagcca cagcttgggg aaagctgtgc agcctgtgac    10440
ccctccagga gaagctgggt aaccaagcct atagtcaggc cgagaacgcc atggcacgga    10500
agaagccatg ctgcctgtga gccctcaga ggacactgag tcaaaaaacc ccacgcgctt     10560
ggaggcgcag gatgggaaaa gaaggtggcg accttcccca cccttcaatc tggggcctga    10620
actggagatc agctgtggat ctccagaaga gggactagtg gttagaggag accccccgga    10680
aaacgcaaaa cagcatattg acgctgggaa agaccagaga ctccatgagt tccaccacg     10740 ctggccgcca ggcacagatc gccgaatagc ggcggccggt gtggggaaat cca           10793
```

<210> SEQ ID NO 18
<211> LENGTH: 3423
<212> TYPE: PRT
<213> ORGANISM: Artificial Sequence
<220> FEATURE:
<223> OTHER INFORMATION: Synthetic construct

<400> SEQUENCE: 18

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
                20                  25                  30

Leu Pro Ala Gly Leu Leu Leu Gly His Gly Pro Ile Arg Met Val Leu
            35                  40                  45

Ala Ile Leu Ala Phe Leu Arg Phe Thr Ala Ile Lys Pro Ser Leu Gly
```

```
                50                  55                  60
Leu Ile Asn Arg Trp Gly Ser Val Gly Lys Lys Glu Ala Met Glu Ile
 65                  70                  75                  80

Ile Lys Lys Phe Lys Lys Asp Leu Ala Ala Met Leu Arg Ile Ile Asn
                 85                  90                  95

Ala Arg Lys Glu Lys Lys Arg Arg Gly Ala Asp Thr Ser Val Gly Ile
                100                 105                 110

Val Gly Leu Leu Leu Thr Thr Ala Met Ala Ala Glu Val Thr Arg Arg
                115                 120                 125

Gly Ser Ala Tyr Tyr Met Tyr Leu Asp Arg Asn Asp Ala Gly Glu Ala
                130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
                180                 185                 190

Thr Thr Ser Thr Trp Val Val Tyr Gly Thr Cys His His Lys Lys Gly
                195                 200                 205

Glu Ala Arg Arg Ser Arg Arg Ala Val Thr Leu Pro Ser His Ser Thr
210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
                275                 280                 285

Tyr Ser Ile Arg Cys Ile Gly Val Ser Asn Arg Asp Phe Val Glu Gly
                290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
                340                 345                 350

Ala Ser Ile Ser Asp Met Ala Ser Asp Ser Arg Cys Pro Thr Gln Gly
                355                 360                 365

Glu Ala Tyr Leu Asp Lys Gln Ser Asp Thr Gln Tyr Val Cys Lys Arg
                370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
                435                 440                 445

Glu Thr Asp Glu Asn Arg Ala Lys Val Glu Ile Thr Pro Asn Ser Pro
                450                 455                 460

Arg Ala Glu Ala Thr Leu Gly Gly Phe Gly Ser Leu Gly Leu Asp Cys
465                 470                 475                 480
```

```
Glu Pro Arg Thr Gly Leu Asp Phe Ser Asp Leu Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Thr Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895
```

-continued

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
            930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
            965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
            1010                1015                1020

Thr Leu Trp Thr Asp Gly Ile Glu Glu Ser Asp Leu Ile Ile Pro
            1025                1030                1035

Lys Ser Leu Ala Gly Pro Leu Ser His His Asn Thr Arg Glu Gly
            1040                1045                1050

Tyr Arg Thr Gln Met Lys Gly Pro Trp His Ser Glu Glu Leu Glu
            1055                1060                1065

Ile Arg Phe Glu Glu Cys Pro Gly Thr Lys Val His Val Glu Glu
            1070                1075                1080

Thr Cys Gly Thr Arg Gly Pro Ser Leu Arg Ser Thr Thr Ala Ser
            1085                1090                1095

Gly Arg Val Ile Glu Glu Trp Cys Cys Arg Glu Cys Thr Met Pro
            1100                1105                1110

Pro Leu Ser Phe Arg Ala Lys Asp Gly Cys Trp Tyr Gly Met Glu
            1115                1120                1125

Ile Arg Pro Arg Lys Glu Pro Glu Ser Asn Leu Val Arg Ser Met
            1130                1135                1140

Val Thr Ala Gly Ser Thr Asp His Met Asp His Phe Ser Leu Gly
            1145                1150                1155

Val Leu Val Ile Leu Leu Met Val Gln Glu Gly Leu Lys Lys Arg
            1160                1165                1170

Met Thr Thr Lys Ile Ile Ile Ser Thr Ser Met Ala Val Leu Val
            1175                1180                1185

Ala Met Ile Leu Gly Gly Phe Ser Met Ser Asp Leu Ala Lys Leu
            1190                1195                1200

Ala Ile Leu Met Gly Ala Thr Phe Ala Glu Met Asn Thr Gly Gly
            1205                1210                1215

Asp Val Ala His Leu Ala Leu Ile Ala Ala Phe Lys Val Arg Pro
            1220                1225                1230

Ala Leu Leu Val Ser Phe Ile Phe Arg Ala Asn Trp Thr Pro Arg
            1235                1240                1245

Glu Ser Met Leu Leu Ala Leu Ala Ser Cys Phe Leu Gln Thr Ala
            1250                1255                1260

Ile Ser Ala Leu Glu Gly Asp Leu Met Val Leu Ile Asn Gly Phe
            1265                1270                1275

Ala Leu Ala Trp Leu Ala Ile Arg Ala Met Val Val Pro Arg Thr
            1280                1285                1290

Asp Asn Ile Thr Leu Ala Ile Leu Ala Ala Leu Thr Pro Leu Ala

```
              1295                1300                1305

Arg  Gly  Thr  Leu  Leu  Val  Ala  Trp  Arg  Ala  Gly  Leu  Ala  Thr  Cys
              1310                1315                1320

Gly  Gly  Phe  Met  Leu  Leu  Ser  Leu  Lys  Gly  Lys  Gly  Ser  Val  Lys
              1325                1330                1335

Lys  Asn  Leu  Pro  Phe  Val  Met  Ala  Leu  Gly  Leu  Thr  Ala  Val  Arg
              1340                1345                1350

Leu  Val  Asp  Pro  Ile  Asn  Val  Val  Gly  Leu  Leu  Leu  Thr  Arg
              1355                1360                1365

Ser  Gly  Lys  Arg  Ser  Trp  Pro  Pro  Ser  Glu  Val  Leu  Thr  Ala  Val
              1370                1375                1380

Gly  Leu  Ile  Cys  Ala  Leu  Ala  Gly  Gly  Phe  Ala  Lys  Ala  Asp  Ile
              1385                1390                1395

Glu  Met  Ala  Gly  Pro  Met  Ala  Ala  Val  Gly  Leu  Leu  Ile  Val  Ser
              1400                1405                1410

Tyr  Val  Val  Ser  Gly  Lys  Ser  Val  Asp  Met  Tyr  Ile  Glu  Arg  Ala
              1415                1420                1425

Gly  Asp  Ile  Thr  Trp  Glu  Lys  Asp  Ala  Glu  Val  Thr  Gly  Asn  Ser
              1430                1435                1440

Pro  Arg  Leu  Asp  Val  Ala  Leu  Asp  Glu  Ser  Gly  Asp  Phe  Ser  Leu
              1445                1450                1455

Val  Glu  Asp  Asp  Gly  Pro  Pro  Met  Arg  Glu  Ile  Ile  Leu  Lys  Val
              1460                1465                1470

Val  Leu  Met  Thr  Ile  Cys  Gly  Met  Asn  Pro  Ile  Ala  Ile  Pro  Phe
              1475                1480                1485

Ala  Ala  Gly  Ala  Trp  Tyr  Val  Tyr  Val  Lys  Thr  Gly  Lys  Arg  Ser
              1490                1495                1500

Gly  Ala  Leu  Trp  Asp  Val  Pro  Ala  Pro  Lys  Glu  Val  Lys  Lys  Gly
              1505                1510                1515

Glu  Thr  Thr  Asp  Gly  Val  Tyr  Arg  Val  Met  Thr  Arg  Arg  Leu  Leu
              1520                1525                1530

Gly  Ser  Thr  Gln  Val  Gly  Val  Gly  Val  Met  Gln  Glu  Gly  Val  Phe
              1535                1540                1545

His  Thr  Met  Trp  His  Val  Thr  Lys  Gly  Ser  Ala  Leu  Arg  Ser  Gly
              1550                1555                1560

Glu  Gly  Arg  Leu  Asp  Pro  Tyr  Trp  Gly  Asp  Val  Lys  Gln  Asp  Leu
              1565                1570                1575

Val  Ser  Tyr  Cys  Gly  Pro  Trp  Lys  Leu  Asp  Ala  Ala  Trp  Asp  Gly
              1580                1585                1590

His  Ser  Glu  Val  Gln  Leu  Leu  Ala  Val  Pro  Pro  Gly  Glu  Arg  Ala
              1595                1600                1605

Arg  Asn  Ile  Gln  Thr  Leu  Pro  Gly  Ile  Phe  Lys  Thr  Lys  Asp  Gly
              1610                1615                1620

Asp  Ile  Gly  Ala  Val  Ala  Leu  Asp  Tyr  Pro  Ala  Gly  Thr  Ser  Gly
              1625                1630                1635

Ser  Pro  Ile  Leu  Asp  Lys  Cys  Gly  Arg  Val  Ile  Gly  Leu  Tyr  Gly
              1640                1645                1650

Asn  Gly  Val  Val  Ile  Lys  Asn  Gly  Ser  Tyr  Val  Ser  Ala  Ile  Thr
              1655                1660                1665

Gln  Gly  Arg  Arg  Glu  Glu  Thr  Pro  Val  Glu  Cys  Phe  Glu  Pro
              1670                1675                1680

Ser  Met  Leu  Lys  Lys  Lys  Gln  Leu  Thr  Val  Leu  Asp  Leu  His  Pro
              1685                1690                1695
```

```
Gly Ala Gly Lys Thr Arg Arg Val Leu Pro Glu Ile Val Arg Glu
    1700            1705                1710

Ala Ile Lys Thr Arg Leu Arg Thr Val Ile Leu Ala Pro Thr Arg
    1715            1720                1725

Val Val Ala Ala Glu Met Glu Glu Ala Leu Arg Gly Leu Pro Val
    1730            1735                1740

Arg Tyr Met Thr Thr Ala Val Asn Val Thr His Ser Gly Thr Glu
    1745            1750                1755

Ile Val Asp Leu Met Cys His Ala Thr Phe Thr Ser Arg Leu Leu
    1760            1765                1770

Gln Pro Ile Arg Val Pro Asn Tyr Asn Leu Tyr Ile Met Asp Glu
    1775            1780                1785

Ala His Phe Thr Asp Pro Ser Ser Ile Ala Ala Arg Gly Tyr Ile
    1790            1795                1800

Ser Thr Arg Val Glu Met Gly Glu Ala Ala Ile Phe Met Thr
    1805            1810                1815

Ala Thr Pro Pro Gly Thr Arg Asp Ala Phe Pro Asp Ser Asn Ser
    1820            1825                1830

Pro Ile Met Asp Thr Glu Val Glu Val Pro Glu Arg Ala Trp Ser
    1835            1840                1845

Ser Gly Phe Asp Trp Val Thr Asp His Ser Gly Lys Thr Val Trp
    1850            1855                1860

Phe Val Pro Ser Val Arg Asn Gly Asn Glu Ile Ala Ala Cys Leu
    1865            1870                1875

Thr Lys Ala Gly Lys Arg Val Ile Gln Leu Ser Arg Lys Thr Phe
    1880            1885                1890

Glu Thr Glu Phe Gln Lys Thr Lys His Gln Glu Trp Asp Phe Val
    1895            1900                1905

Val Thr Thr Asp Ile Ser Glu Met Gly Ala Asn Phe Lys Ala Asp
    1910            1915                1920

Arg Val Ile Asp Ser Arg Arg Cys Leu Lys Pro Val Ile Leu Asp
    1925            1930                1935

Gly Glu Arg Val Ile Leu Ala Gly Pro Met Pro Val Thr His Ala
    1940            1945                1950

Ser Ala Ala Gln Arg Arg Gly Arg Ile Gly Arg Asn Pro Asn Lys
    1955            1960                1965

Pro Gly Asp Glu Tyr Leu Tyr Gly Gly Gly Cys Ala Glu Thr Asp
    1970            1975                1980

Glu Asp His Ala His Trp Leu Glu Ala Arg Met Leu Leu Asp Asn
    1985            1990                1995

Ile Tyr Leu Gln Asp Gly Leu Ile Ala Ser Leu Tyr Arg Pro Glu
    2000            2005                2010

Ala Asp Lys Val Ala Ala Ile Glu Gly Glu Phe Lys Leu Arg Thr
    2015            2020                2025

Glu Gln Arg Lys Thr Phe Val Glu Leu Met Lys Arg Gly Asp Leu
    2030            2035                2040

Pro Val Trp Leu Ala Tyr Gln Val Ala Ser Ala Gly Ile Thr Tyr
    2045            2050                2055

Thr Asp Arg Arg Trp Cys Phe Asp Gly Thr Thr Asn Asn Thr Ile
    2060            2065                2070

Met Glu Asp Ser Val Pro Ala Glu Val Trp Thr Arg His Gly Glu
    2075            2080                2085
```

-continued

```
Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
```

```
                    2480                    2485                    2490
Asn Ile Phe Arg Gly Ser Tyr Leu Ala Gly Ala Ser Leu Ile Tyr
    2495                    2500                    2505

Thr Val Thr Arg Asn Ala Gly Leu Val Lys Arg Arg Gly Gly Gly
    2510                    2515                    2520

Thr Gly Glu Thr Leu Gly Glu Lys Trp Lys Ala Arg Leu Asn Gln
    2525                    2530                    2535

Met Ser Ala Leu Glu Phe Tyr Ser Tyr Lys Lys Ser Gly Ile Thr
    2540                    2545                    2550

Glu Val Cys Arg Glu Glu Ala Arg Arg Ala Leu Lys Asp Gly Val
    2555                    2560                    2565

Ala Thr Gly Gly His Ala Val Ser Arg Gly Ser Ala Lys Leu Arg
    2570                    2575                    2580

Trp Leu Val Glu Arg Gly Tyr Leu Gln Pro Tyr Gly Lys Val Ile
    2585                    2590                    2595

Asp Leu Gly Cys Gly Arg Gly Gly Trp Ser Tyr Tyr Ala Ala Thr
    2600                    2605                    2610

Ile Arg Lys Val Gln Glu Val Lys Gly Tyr Thr Lys Gly Gly Pro
    2615                    2620                    2625

Gly His Glu Glu Pro Val Leu Val Gln Ser Tyr Gly Trp Asn Ile
    2630                    2635                    2640

Val Arg Leu Lys Ser Gly Val Asp Val Phe His Met Ala Ala Glu
    2645                    2650                    2655

Pro Cys Asp Thr Leu Leu Cys Asp Ile Gly Glu Ser Ser Ser Ser
    2660                    2665                    2670

Pro Glu Val Glu Glu Ala Arg Thr Leu Arg Val Leu Ser Met Val
    2675                    2680                    2685

Gly Asp Trp Leu Glu Lys Arg Pro Gly Ala Phe Cys Ile Lys Val
    2690                    2695                    2700

Leu Cys Pro Tyr Thr Ser Thr Met Met Glu Thr Leu Glu Arg Leu
    2705                    2710                    2715

Gln Arg Arg Tyr Gly Gly Gly Leu Val Arg Val Pro Leu Ser Arg
    2720                    2725                    2730

Asn Ser Thr His Glu Met Tyr Trp Val Ser Gly Ala Lys Ser Asn
    2735                    2740                    2745

Thr Ile Lys Ser Val Ser Thr Thr Ser Gln Leu Leu Leu Gly Arg
    2750                    2755                    2760

Met Asp Gly Pro Arg Arg Pro Val Lys Tyr Glu Glu Asp Val Asn
    2765                    2770                    2775

Leu Gly Ser Gly Thr Arg Ala Val Val Ser Cys Ala Glu Ala Pro
    2780                    2785                    2790

Asn Met Lys Ile Ile Gly Asn Arg Ile Glu Arg Ile Arg Ser Glu
    2795                    2800                    2805

His Ala Glu Thr Trp Phe Phe Asp Glu Asn His Pro Tyr Arg Thr
    2810                    2815                    2820

Trp Ala Tyr His Gly Ser Tyr Val Ala Pro Thr Gln Gly Ser Ala
    2825                    2830                    2835

Ser Ser Leu Ile Asn Gly Val Val Arg Leu Leu Ser Lys Pro Trp
    2840                    2845                    2850

Asp Val Val Thr Gly Val Thr Gly Ile Ala Met Thr Asp Thr Thr
    2855                    2860                    2865

Pro Tyr Gly Gln Gln Arg Val Phe Lys Glu Lys Val Asp Thr Arg
    2870                    2875                    2880
```

```
Val Pro  Asp Pro Gln Glu Gly  Thr Arg Gln Val Met  Ser Met Val
    2885             2890              2895

Ser Ser  Trp Leu Trp Lys Glu  Leu Gly Lys His Lys  Arg Pro Arg
    2900             2905              2910

Val Cys  Thr Lys Glu Glu Phe  Ile Asn Lys Val Arg  Ser Asn Ala
    2915             2920              2925

Ala Leu  Gly Ala Ile Phe Glu  Glu Lys Glu Trp      Lys Thr Ala
    2930             2935              2940

Val Glu  Ala Val Asn Asp Pro  Arg Phe Trp Ala Leu  Val Asp Lys
    2945             2950              2955

Glu Arg  Glu His His Leu Arg  Gly Glu Cys Gln Ser  Cys Val Tyr
    2960             2965              2970

Asn Met  Met Gly Lys Arg Glu  Lys Lys Gln Gly Glu  Phe Gly Lys
    2975             2980              2985

Ala Lys  Gly Ser Arg Ala Ile  Trp Tyr Met Trp Leu  Gly Ala Arg
    2990             2995              3000

Phe Leu  Glu Phe Glu Ala Leu  Gly Phe Leu Asn Glu  Asp His Trp
    3005             3010              3015

Met Gly  Arg Glu Asn Ser Gly  Gly Gly Val Glu Gly  Leu Gly Leu
    3020             3025              3030

Gln Arg  Leu Gly Tyr Val Leu  Glu Glu Met Ser Arg  Ile Pro Gly
    3035             3040              3045

Gly Arg  Met Tyr Ala Asp Asp  Thr Ala Gly Trp Asp  Thr Arg Ile
    3050             3055              3060

Ser Arg  Phe Asp Leu Glu Asn  Glu Ala Leu Ile Thr  Asn Gln Met
    3065             3070              3075

Glu Lys  Gly His Arg Ala Leu  Ala Leu Ala Ile Ile  Lys Tyr Thr
    3080             3085              3090

Tyr Gln  Asn Lys Val Val Lys  Val Leu Arg Pro Ala  Glu Lys Gly
    3095             3100              3105

Lys Thr  Val Met Asp Ile Ile  Ser Arg Gln Asp Gln  Arg Gly Ser
    3110             3115              3120

Gly Gln  Val Val Thr Tyr Ala  Leu Asn Thr Phe Thr  Asn Leu Val
    3125             3130              3135

Val Gln  Leu Ile Arg Asn Met  Glu Ala Glu Glu Val  Leu Glu Met
    3140             3145              3150

Gln Asp  Leu Trp Leu Leu Arg  Arg Ser Glu Lys Val  Thr Asn Trp
    3155             3160              3165

Leu Gln  Ser Asn Gly Trp Asp  Arg Leu Lys Arg Met  Ala Val Ser
    3170             3175              3180

Gly Asp  Asp Cys Val Val Lys  Pro Ile Asp Asp Arg  Phe Ala His
    3185             3190              3195

Ala Leu  Arg Phe Leu Asn Asp  Met Gly Lys Val Arg  Lys Asp Thr
    3200             3205              3210

Gln Glu  Trp Lys Pro Ser Thr  Gly Trp Asp Asn Trp  Glu Glu Val
    3215             3220              3225

Pro Phe  Cys Ser His His Phe  Asn Lys Leu His Leu  Lys Asp Gly
    3230             3235              3240

Arg Ser  Ile Val Val Pro Cys  Arg His Gln Asp Glu  Leu Ile Gly
    3245             3250              3255

Arg Ala  Arg Val Ser Pro Gly  Ala Gly Trp Ser Ile  Arg Glu Thr
    3260             3265              3270
```

| Ala | Cys | Leu | Ala | Lys | Ser | Tyr | Ala | Gln | Met | Trp | Gln | Leu | Leu | Tyr |
| | 3275 | | | | 3280 | | | | 3285 | | | | | |

| Phe | His | Arg | Arg | Asp | Leu | Arg | Leu | Met | Ala | Asn | Ala | Ile | Cys | Ser |
| 3290 | | | | | 3295 | | | | | 3300 | | | | |

| Ser | Val | Pro | Val | Asp | Trp | Val | Pro | Thr | Gly | Arg | Thr | Thr | Trp | Ser |
| 3305 | | | | | 3310 | | | | | 3315 | | | | |

| Ile | His | Gly | Lys | Gly | Glu | Trp | Met | Thr | Thr | Glu | Asp | Met | Leu | Val |
| 3320 | | | | | 3325 | | | | | 3330 | | | | |

| Val | Trp | Asn | Arg | Val | Trp | Ile | Glu | Glu | Asn | Asp | His | Met | Glu | Asp |
| 3335 | | | | | 3340 | | | | | 3345 | | | | |

| Lys | Thr | Pro | Val | Thr | Lys | Trp | Thr | Asp | Ile | Pro | Tyr | Leu | Gly | Lys |
| 3350 | | | | | 3355 | | | | | 3360 | | | | |

| Arg | Glu | Asp | Leu | Trp | Cys | Gly | Ser | Leu | Ile | Gly | His | Arg | Pro | Arg |
| 3365 | | | | | 3370 | | | | | 3375 | | | | |

| Thr | Thr | Trp | Ala | Glu | Asn | Ile | Lys | Asn | Thr | Val | Asn | Met | Val | Arg |
| 3380 | | | | | 3385 | | | | | 3390 | | | | |

| Arg | Ile | Ile | Gly | Asp | Glu | Glu | Lys | Tyr | Met | Asp | Tyr | Leu | Ser | Thr |
| 3395 | | | | | 3400 | | | | | 3405 | | | | |

| Gln | Val | Arg | Tyr | Leu | Gly | Glu | Glu | Gly | Ser | Thr | Pro | Gly | Val | Leu |
| 3410 | | | | | 3415 | | | | | 3420 | | | | |

<210> SEQ ID NO 19
<211> LENGTH: 10675
<212> TYPE: DNA
<213> ORGANISM: Artificial Sequence
<220> FEATURE:
<223> OTHER INFORMATION: Synthetic construct

<400> SEQUENCE: 19

```
gttgttgatc tgtgtgaatc agactgcgac agttcgagtt tgaagcgaaa gctagcaaca      60
gtatcaacag gttttatttt ggatttggaa acgagagttt ctggtcatga aaaacccaaa     120
aaagaaatcc ggaggattcc ggattgtcaa tatgctaaaa cgcggagtag cccgtgtgag     180
cccctttggg ggcttgaaga ggctgccagc cggacttctg ctgggtcatg ggcccatcag     240
gatggtcttg gcgattctag ccttttttgag attcacggca atcaagccat cactgggtct     300
catcaataga tggggttcag tggggaaaaa agaggctatg gaaacaataa agaagttcaa     360
gaaagatctg gctgccatgc tgagaataat caatgctagg aaggagaaga agagacgagg     420
cgcagatact agtgtcggaa ttgttggcct cctgctgacc acagctatgg cagcggaggt     480
cactagacgt gggagtgcat actatatgta cttggacaga aacgatgctg gggaggccat     540
atcttttcca accacattgg ggatgaataa gtgttatata cagatcatgg atcttggaca     600
catgtgtgat gccaccatga gctatgaatg ccctatgctg gatgagggg tggaaccaga     660
tgacgtcgat tgttggtgca acacgacgtc aacttgggtt gtgtacggaa cctgccatca     720
caaaaaggt gaagcacgga gatctagaag agctgtgacg ctcccctccc attccaccag     780
gaagctgcaa acgcggtcgc aaacctggtt ggaatcaaga gaatacacaa agcacttgat     840
tagagtcgaa aattggatat tcaggaaccc tggcttcgcg ttagcagcag ctgccatcgc     900
ttggcttttg ggaagctcaa cgagccaaaa agtcatatac ttggtcatga tactgctgat     960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca acagtcagca acatggcgga    1140
ggtaagatcc tactgctatg aggcatcaat atcagacatg gcttctgaca gccgctgccc    1200
```

```
aacacaaggt gaagcctacc ttgacaagca atcagacact caatatgtct gcaaaagaac    1260
gttagtggac agaggctggg gaaatggatg tggactttt ggcaaaggga gcctggtgac     1320
atgcgctaag tttgcatgct ccaagaaaat gaccgggaag agcatccagc cagagaatct    1380
ggagtaccgg ataatgctgt cagttcatgg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg cacgctggg gcagacaccg gaactccaca     1680
ctggaacaac aaagaagcac tggtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccac ttgaaatgtc gcctgaaaat    1860
ggataaactt agattgaagg gcgtgtcata ctccttgtgt actgcagcgt tcacattcac    1920
caagatcccg gctgaaacac tgcacgggac agtcacagtg gaggtacagt acgcagggac    1980
agatggacct tgcaaggttc cagctcagat ggcggtggac atgcaaactc tgaccccagt    2040
tgggaggttg ataaccgcta accccgtaat cactgaaagc actgagaact ctaagatgat    2100
gctgaacttt gatccaccat ttgggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tggactttg gatcagttgg     2280 aggcgctctc aactcattgg gcaagggcat ccatcaaatt tttggagcag ctttcaaatc    2340 attgttttgga ggaatgtcct ggttctcaca aattctcatt ggaacgttgc tgatgtggtt    2400
gggtctgaac acaaagaatg gatctatttc ccttatgtgc ttggccttag ggggagtgtt    2460
gatcttctta tccacagccg tctctgctga tgtggggtgc tcggtggact ctcaaagaa     2520 ggagacgaga tgcggtacag gggtgttcgt ctataacgac gttgaagcct ggaggacag    2580 gtacaagtac catcctgact cccccgtag attggcagca gcagtcaagc aagcctggga     2640
agatggtatc tgcgggatct cctctgtttc aagaatggaa aacatcatgt ggagatcagt    2700
agaaggggag ctcaacgcaa tcctggaaga gaatggagtt caactgacgg tcgttgtggg    2760
atctgtaaaa aaccccatgt ggagaggtcc acagagattg cccgtgcctg tgaacgagct    2820
gccccacggc tggaaggctt gggggaaatc gtatttcgtc agagcagcaa agacaaataa    2880
cagctttgtc gtggatggtg acacactgaa ggaatgccca ctcaaacata gagcatggaa    2940
cagctttctt gtggaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gccatctga tcgagatgaa acatgtgaa tggccaaagt cccacacatt      3180
gtggacagat ggaatagaag agagtgatct gatcataccc aagtctttag ctgggccact    3240
cagccatcac aataccagag agggctacag gacccaaatg aaagggccat ggcacagtga    3300
agagcttgaa attcggtttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgccccccact gtcgttccgg gctaaagatg ctgttggta    3480 tggaatggag ataaggccca ggaaagaacc agaaagcaac ttagtaaggt caatggtgac    3540
```

```
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacaccccgt gaaagcatgc tgctggcctt ggcctcgtgt cttttgcaaa ctgcgatctc    3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggccttgcta cttgcggggg    4080
gtttatgctc ctctctctga agggaaaagg cagtgtgaag aagaacttac catttgtcat    4140
ggccctggga ctaaccgctg tgaggctggt cgaccccatc aacgtggtgg gactgctgtt    4200
gctcacaagg agtgggaagc ggagctggcc cctagcgaa gtactcacag ctgttggcct    4260
gatatgcgca ttggctggag ggttcgccaa ggcagatata gagatggctg ggcccatggc    4320
cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccc    4500
catgagagag atcatactca aggtggtcct gatgaccatc tgtggcatga cccaatagc    4560 cataccctt gcagctggag cgtggtacgt atacgtgaag actggaaaaa ggagtggtgc    4620
tctatgggat gtgcctgctc ccaaggaagt aaaaagggg gagaccacag atggagtgta    4680
cagagtaatg actcgtagac tgctaggttc aacacaagtt ggagtgggag ttatgcaaga    4740
gggggtcttt cacactatgt ggcacgtcac aaaaggatcc cgcgctgagaa gcggtgaagg    4800 gagacttgat ccatactggg gagatgtcaa gcaggatctg gtgtcatact gtggtccatg    4860
gaagctagat gccgcctggg atgggcacag cgaggtgcag ctcttggccg tgcccccgg    4920 agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt atggcaatgg ggtcgtgatc aaaaacggga gttatgttag    5100
tgccatcacc caaggagga gggaggaaga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccctt agagggcttc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaaccg    5580 tgacgcattt ccggactcca actcaccaat tatggacacc gaagtggaag tcccagagag    5640
agcctggagc tcaggctttg attgggtgac ggatcattct ggaaaaacag tttggtttgt    5700
tccaagcgtg aggaacggca tgagatcgc agcttgtctg acaaaggctg gaaaacgggt    5760
catacagctc agcagaaaga cttttgagac agagttccag aaaacaaaac atcaagagtg    5820
ggactttgtc gtgacaactg acatttcaga gatgggcgcc aactttaaag ctgaccgtgt    5880
catagattcc aggagatgcc taaagccggt catacttgat ggcgagagag tcattctggc    5940
```

```
tggacccatg cctgtcacac atgccagcgc tgcccagagg aggggcgca taggcaggaa    6000 tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agacctttgt ggaactcatg aaaagaggag atcttcctgt    6240
ttggctggcc tatcaggttg catctgccgg aataacctac acagatagaa gatggtgctt    6300
tgatggcacg accaacaaca ccataatgga agacagtgtg ccggcagagg tgtggaccag    6360
acacggagag aaaagagtgc tcaaaccgag gtggatggac gccagagttt gttcagatca    6420
tgcggccctg aagtcattca aggagtttgc cgctgggaaa agaggagcgg cttttggagt    6480
gatggaagcc ctgggaacac tgccaggaca catgacagag agattccagg aagccattga    6540
caacctcgct gtgctcatgc gggcagagac tggaagcagg ccttacaaag ccgcggcggc    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgtcctc attgttgtgt cctattgct ggtggtgctc atacctgagc cagaaaagca    6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg gggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atggccacgc aagctggagt    7140
gttgtttggc atgggcaaag gatgccatt ctacgcatgg gactttggag tcccgctgct    7200
aatgataggt tgctactcac aattaacacc cctgacccta atagtggcca tcattttgct    7260
cgtggcgcac tacatgtact tgatcccagg gctgcaggca gcagctgcgc gtgctgccca    7320
gaagagaacg gcagctggca tcatgaagaa ccctgttgtg gatggaatag tggtgactga    7380
cattgacaca atgacaattg accccaagt ggagaaaaag atgggacagg tgctactcat    7440
agcagtagcc gtctccagcg ccatactgtc gcggaccgcc tgggggtggg gggaggctgg    7500
ggctctgatc acagccgcaa cttccacttt gtgggaaggc tctccgaaca agtactggaa    7560
ctcctctaca gccacttcac tgtgtaacat ttttagggga agttacttgg ctggagcttc    7620
tctaatctac acagtaacaa gaaacgctgg cttggtcaag acgtgggg gtggaacagg    7680 agagaccctg ggagagaaat ggaaggcccg cttgaaccag atgtcggccc tggagttcta    7740
ctcctacaaa aagtcaggca tcaccgaggt gtgcagagaa gaggcccgcc gcgccctcaa    7800
ggacggtgtg caacgggag ccatgctgt gtcccgagga agtgcaaagc tgagatggtt    7860
ggtggagcgg ggatacctgc agccctatgg aaaggtcatt gatctggat gtggcagagg    7920 gggctggagt tactacgtcg ccaccatccg caaagttcaa gaagtgaaag gatacacaaa    7980
aggaggccct ggtcatgaag aacccgtgtt ggtgcaaagc tatgggtgga acatagtccg    8040
tcttaagagt ggggtggacg tctttcatat ggcggctgag ccgtgtgaca cgttgctgtg    8100
tgacataggt gagtcatcat ctagtcctga agtggaagaa gcacggacgc tcagagtcct    8160
ctccatggtg ggggattggc ttgaaaaaag accaggagcc ttttgtataa agtgttgtg    8220 cccatacacc agcactatga tggaaccct ggagcgactg cagcgtaggt atgggggagg    8280
```

```
actggtcaga gtgccactct cccgcaactc tacacatgag atgtactggg tctctggagc      8340
gaaaagcaac accataaaaa gtgtgtccac cacgagccag ctcctcttgg ggcgcatgga      8400
cgggcctagg aggccagtga aatatgagga ggatgtgaat ctcggctctg gcacgcgggc      8460
tgtggtaagc tgcgctgaag ctcccaacat gaagatcatt ggtaaccgca ttgaaaggat      8520
ccgcagtgag cacgcggaaa cgtggttctt tgacgagaac cacccatata ggacatgggc      8580
ttaccatgga agctatgagg cccccacaca agggtcagcg tcctctctaa taaacggggt      8640
tgtcaggctc ctgtcaaaac cctgggatgt ggtgactgga gtcacaggaa tagccatgac      8700
cgacaccaca ccgtatggtc agcaaagagt tttcaaggaa aaagtggaca ctagggtgcc      8760
agacccccaa gaaggcactc gtcaggttat gagcatggtc tcttcctggt tgtggaaaga      8820
gctaggcaaa cacaaacggc cacgagtctg caccaaagaa gagttcatca acaaggttcg      8880
tagcaatgca gcattagggg caatatttga agaggaaaaa gagtggaaga ctgcagtgga      8940
agctgtgaac gatccaaggt tctgggctct agtggacaag gaaagagagc accacctgag      9000
aggagagtgc cagagctgtg tgtacaacat gatgggaaaa agagaaaaga aacaagggga      9060
atttggaaag gccaagggca gccgcgccat ctggtatatg tggctagggg ctagatttct      9120
agagttcgaa gcccttggat tcttgaacga ggatcactgg atgggagag agaactcagg      9180 aggtggtgtt gaagggctgg gattacaaag actcggatat gtcctagaag agatgagtcg      9240
tataccagga ggaaggatgt atgcagatga cactgctggc tgggacaccc gcattagcag      9300
gtttgatctg gagaatgaag ctctaatcac caaccaaatg gagaaagggc acagggcctt      9360
ggcattggcc ataatcaagt acacatacca aaacaaagtg gtaaaggtcc ttagaccagc      9420
tgaaaagggg aaaacagtta tggacattat ttcgagacaa gaccaaaggg ggagcggaca      9480
agttgtcact tacgctctta acacatttac caacctagtg gtgcaactca ttcggaatat      9540
ggaggctgag gaagttctag agatgcaaga cttgtggctg ctgcggaggt cagagaaagt      9600
gaccaactgg ttgcagagca acggatggga taggctcaaa cgaatggcag tcagtggaga      9660
tgattgcgtt gtgaagccaa ttgatgatag gtttgcacat gccctcaggt tcttgaatga      9720
tatgggaaaa gttaggaagg acacacaaga gtggaaaccc tcaactggat gggacaactg      9780
ggaagaagtt ccgttttgct cccaccactt caacaagctc catctcaagg acgggaggtc      9840
cattgtggtt ccctgccgcc accaagatga actgattggc cgggcccgcg tctctccagg      9900
ggcgggatgg agcatccggg agactgcttg cctagcaaaa tcatatgcgc aaatgtggca      9960
gctcctttat ttccacagaa gggacctccg actgatggcc aatgccattt gttcatctgt     10020
gccagttgac tgggttccaa ctgggagaac tacctggtca atccatggaa agggagaatg     10080
gatgaccact gaagacatgc ttgtggtgtg aacagagtg tggattgagg agaacgacca     10140
catggaagac aagaccccag ttacgaaatg gacagacatt ccctatttgg gaaaagggga     10200
agacttgtgg tgtggatctc tcataggca cagaccgcgc accacctggg ctgagaacat     10260
taaaaacaca gtcaacatgg tgcgcaggat cataggtgat gaagaaaagt acatggacta     10320
cctatccacc caagttcgct acttgggtga agaagggtct acacctggag tgctgtaagc     10380
accaatctta atgttgtcag gcctgctagt cagccacagc ttggggaaag ctgtgcagcc     10440 tgtgacccccc ccaggagaag ctgggaaacc aagcctatag tcaggccgag aacgccatgg     10500
cacggaagaa gccatgctgc ctgtgagccc ctcagaggac actgagtcaa aaacccccac     10560
gcgcttggag gcgcaggatg ggaaaagaag gtggcgacct tccccaccct tcaatctggg     10620
gcctgaactg gagatcagct gtggatctcc agaagaggga ctagtggtta gagga         10675
```

<210> SEQ ID NO 20
<211> LENGTH: 3423
<212> TYPE: PRT
<213> ORGANISM: Artificial Sequence
<220> FEATURE:
<223> OTHER INFORMATION: Synthetic construct

<400> SEQUENCE: 20

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Gly His Gly Pro Ile Arg Met Val Leu
            35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
            85                  90                  95

Ala Arg Lys Glu Lys Lys Arg Gly Ala Asp Thr Ser Val Gly Ile
            100                 105                 110

Val Gly Leu Leu Leu Thr Thr Ala Met Ala Ala Glu Val Thr Arg Arg
            115                 120                 125

Gly Ser Ala Tyr Tyr Met Tyr Leu Asp Arg Asn Asp Ala Gly Glu Ala
            130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
            195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
            245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
            290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
            355                 360                 365
```

```
Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
    595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
            675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
    755                 760                 765

Thr Lys Asn Gly Ser Ile Ser Leu Met Cys Leu Ala Leu Gly Gly Val
770                 775                 780
```

```
Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
                835                 840                 845

Cys Gly Ile Ser Ser Val Ser Arg Met Glu Asn Ile Met Trp Arg Ser
850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
                900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
```

-continued

```
            1190                1195                1200
Ala Ile Leu Met Gly Ala Thr Phe Ala Glu Met Asn Thr Gly Gly
            1205                1210                1215
Asp Val Ala His Leu Ala Leu Ile Ala Ala Phe Lys Val Arg Pro
            1220                1225                1230
Ala Leu Leu Val Ser Phe Ile Phe Arg Ala Asn Trp Thr Pro Arg
            1235                1240                1245
Glu Ser Met Leu Leu Ala Leu Ala Ser Cys Leu Leu Gln Thr Ala
            1250                1255                1260
Ile Ser Ala Leu Glu Gly Asp Leu Met Val Leu Ile Asn Gly Phe
            1265                1270                1275
Ala Leu Ala Trp Leu Ala Ile Arg Ala Met Val Val Pro Arg Thr
            1280                1285                1290
Asp Asn Ile Thr Leu Ala Ile Leu Ala Ala Leu Thr Pro Leu Ala
            1295                1300                1305
Arg Gly Thr Leu Leu Val Ala Trp Arg Ala Gly Leu Ala Thr Cys
            1310                1315                1320
Gly Gly Phe Met Leu Leu Ser Leu Lys Gly Lys Gly Ser Val Lys
            1325                1330                1335
Lys Asn Leu Pro Phe Val Met Ala Leu Gly Leu Thr Ala Val Arg
            1340                1345                1350
Leu Val Asp Pro Ile Asn Val Val Gly Leu Leu Leu Leu Thr Arg
            1355                1360                1365
Ser Gly Lys Arg Ser Trp Pro Pro Ser Glu Val Leu Thr Ala Val
            1370                1375                1380
Gly Leu Ile Cys Ala Leu Ala Gly Gly Phe Ala Lys Ala Asp Ile
            1385                1390                1395
Glu Met Ala Gly Pro Met Ala Ala Val Gly Leu Leu Ile Val Ser
            1400                1405                1410
Tyr Val Val Ser Gly Lys Ser Val Asp Met Tyr Ile Glu Arg Ala
            1415                1420                1425
Gly Asp Ile Thr Trp Glu Lys Asp Ala Glu Val Thr Gly Asn Ser
            1430                1435                1440
Pro Arg Leu Asp Val Ala Leu Asp Glu Ser Gly Asp Phe Ser Leu
            1445                1450                1455
Val Glu Asp Asp Gly Pro Pro Met Arg Glu Ile Ile Leu Lys Val
            1460                1465                1470
Val Leu Met Thr Ile Cys Gly Met Asn Pro Ile Ala Ile Pro Phe
            1475                1480                1485
Ala Ala Gly Ala Trp Tyr Val Tyr Val Lys Thr Gly Lys Arg Ser
            1490                1495                1500
Gly Ala Leu Trp Asp Val Pro Ala Pro Lys Glu Val Lys Lys Gly
            1505                1510                1515
Glu Thr Thr Asp Gly Val Tyr Arg Val Met Thr Arg Arg Leu Leu
            1520                1525                1530
Gly Ser Thr Gln Val Gly Val Gly Val Met Gln Glu Gly Val Phe
            1535                1540                1545
His Thr Met Trp His Val Thr Lys Gly Ser Ala Leu Arg Ser Gly
            1550                1555                1560
Glu Gly Arg Leu Asp Pro Tyr Trp Gly Asp Val Lys Gln Asp Leu
            1565                1570                1575
Val Ser Tyr Cys Gly Pro Trp Lys Leu Asp Ala Ala Trp Asp Gly
            1580                1585                1590
```

```
His Ser Glu Val Gln Leu Leu Ala Val Pro Pro Gly Glu Arg Ala
    1595                1600                1605

Arg Asn Ile Gln Thr Leu Pro Gly Ile Phe Lys Thr Lys Asp Gly
    1610                1615                1620

Asp Ile Gly Ala Val Ala Leu Asp Tyr Pro Ala Gly Thr Ser Gly
    1625                1630                1635

Ser Pro Ile Leu Asp Lys Cys Gly Arg Val Ile Gly Leu Tyr Gly
    1640                1645                1650

Asn Gly Val Val Ile Lys Asn Gly Ser Tyr Val Ser Ala Ile Thr
    1655                1660                1665

Gln Gly Arg Arg Glu Glu Glu Thr Pro Val Glu Cys Phe Glu Pro
    1670                1675                1680

Ser Met Leu Lys Lys Lys Gln Leu Thr Val Leu Asp Leu His Pro
    1685                1690                1695

Gly Ala Gly Lys Thr Arg Arg Val Leu Pro Glu Ile Val Arg Glu
    1700                1705                1710

Ala Ile Lys Thr Arg Leu Arg Thr Val Ile Leu Ala Pro Thr Arg
    1715                1720                1725

Val Val Ala Ala Glu Met Glu Glu Ala Leu Arg Gly Leu Pro Val
    1730                1735                1740

Arg Tyr Met Thr Thr Ala Val Asn Val Thr His Ser Gly Thr Glu
    1745                1750                1755

Ile Val Asp Leu Met Cys His Ala Thr Phe Thr Ser Arg Leu Leu
    1760                1765                1770

Gln Pro Ile Arg Val Pro Asn Tyr Asn Leu Tyr Ile Met Asp Glu
    1775                1780                1785

Ala His Phe Thr Asp Pro Ser Ser Ile Ala Ala Arg Gly Tyr Ile
    1790                1795                1800

Ser Thr Arg Val Glu Met Gly Glu Ala Ala Ile Phe Met Thr
    1805                1810                1815

Ala Thr Pro Pro Gly Thr Arg Asp Ala Phe Pro Asp Ser Asn Ser
    1820                1825                1830

Pro Ile Met Asp Thr Glu Val Glu Val Pro Glu Arg Ala Trp Ser
    1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
    1880                1885                1890

Glu Thr Glu Phe Gln Lys Thr Lys His Gln Glu Trp Asp Phe Val
    1895                1900                1905

Val Thr Thr Asp Ile Ser Glu Met Gly Ala Asn Phe Lys Ala Asp
    1910                1915                1920

Arg Val Ile Asp Ser Arg Arg Cys Leu Lys Pro Val Ile Leu Asp
    1925                1930                1935

Gly Glu Arg Val Ile Leu Ala Gly Pro Met Pro Val Thr His Ala
    1940                1945                1950

Ser Ala Ala Gln Arg Arg Gly Arg Ile Gly Arg Asn Pro Asn Lys
    1955                1960                1965

Pro Gly Asp Glu Tyr Leu Tyr Gly Gly Gly Cys Ala Glu Thr Asp
    1970                1975                1980
```

```
Glu Asp His Ala His Trp Leu Glu Ala Arg Met Leu Leu Asp Asn
1985                1990                1995

Ile Tyr Leu Gln Asp Gly Leu Ile Ala Ser Leu Tyr Arg Pro Glu
2000                2005                2010

Ala Asp Lys Val Ala Ala Ile Glu Gly Glu Phe Lys Leu Arg Thr
2015                2020                2025

Glu Gln Arg Lys Thr Phe Val Glu Leu Met Lys Arg Gly Asp Leu
2030                2035                2040

Pro Val Trp Leu Ala Tyr Gln Val Ala Ser Ala Gly Ile Thr Tyr
2045                2050                2055

Thr Asp Arg Arg Trp Cys Phe Asp Gly Thr Thr Asn Asn Thr Ile
2060                2065                2070

Met Glu Asp Ser Val Pro Ala Glu Val Trp Thr Arg His Gly Glu
2075                2080                2085

Lys Arg Val Leu Lys Pro Arg Trp Met Asp Ala Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
```

```
                    2375                2380                2385
Tyr Met Tyr Leu Ile Pro Gly Leu Gln Ala Ala Ala Arg Ala
                    2390                2395                2400
Ala Gln Lys Arg Thr Ala Ala Gly Ile Met Lys Asn Pro Val Val
    2405                2410                2415
Asp Gly Ile Val Val Thr Asp Ile Asp Thr Met Thr Ile Asp Pro
    2420                2425                2430
Gln Val Glu Lys Lys Met Gly Gln Val Leu Leu Ile Ala Val Ala
    2435                2440                2445
Val Ser Ser Ala Ile Leu Ser Arg Thr Ala Trp Gly Trp Gly Glu
    2450                2455                2460
Ala Gly Ala Leu Ile Thr Ala Ala Thr Ser Thr Leu Trp Glu Gly
    2465                2470                2475
Ser Pro Asn Lys Tyr Trp Asn Ser Ser Thr Ala Thr Ser Leu Cys
    2480                2485                2490
Asn Ile Phe Arg Gly Ser Tyr Leu Ala Gly Ala Ser Leu Ile Tyr
    2495                2500                2505
Thr Val Thr Arg Asn Ala Gly Leu Val Lys Arg Gly Gly Gly
    2510                2515                2520
Thr Gly Glu Thr Leu Gly Glu Lys Trp Lys Ala Arg Leu Asn Gln
    2525                2530                2535
Met Ser Ala Leu Glu Phe Tyr Ser Tyr Lys Lys Ser Gly Ile Thr
    2540                2545                2550
Glu Val Cys Arg Glu Glu Ala Arg Arg Ala Leu Lys Asp Gly Val
    2555                2560                2565
Ala Thr Gly Gly His Ala Val Ser Arg Gly Ser Ala Lys Leu Arg
    2570                2575                2580
Trp Leu Val Glu Arg Gly Tyr Leu Gln Pro Tyr Gly Lys Val Ile
    2585                2590                2595
Asp Leu Gly Cys Gly Arg Gly Gly Trp Ser Tyr Tyr Val Ala Thr
    2600                2605                2610
Ile Arg Lys Val Gln Glu Val Lys Gly Tyr Thr Lys Gly Gly Pro
    2615                2620                2625
Gly His Glu Glu Pro Val Leu Val Gln Ser Tyr Gly Trp Asn Ile
    2630                2635                2640
Val Arg Leu Lys Ser Gly Val Asp Val Phe His Met Ala Ala Glu
    2645                2650                2655
Pro Cys Asp Thr Leu Leu Cys Asp Ile Gly Glu Ser Ser Ser Ser
    2660                2665                2670
Pro Glu Val Glu Glu Ala Arg Thr Leu Arg Val Leu Ser Met Val
    2675                2680                2685
Gly Asp Trp Leu Glu Lys Arg Pro Gly Ala Phe Cys Ile Lys Val
    2690                2695                2700
Leu Cys Pro Tyr Thr Ser Thr Met Met Glu Thr Leu Glu Arg Leu
    2705                2710                2715
Gln Arg Arg Tyr Gly Gly Gly Leu Val Arg Val Pro Leu Ser Arg
    2720                2725                2730
Asn Ser Thr His Glu Met Tyr Trp Val Ser Gly Ala Lys Ser Asn
    2735                2740                2745
Thr Ile Lys Ser Val Ser Thr Thr Ser Gln Leu Leu Leu Gly Arg
    2750                2755                2760
Met Asp Gly Pro Arg Arg Pro Val Lys Tyr Glu Glu Asp Val Asn
    2765                2770                2775
```

```
Leu Gly Ser Gly Thr Arg Ala Val Val Ser Cys Ala Glu Ala Pro
    2780            2785                2790

Asn Met Lys Ile Ile Gly Asn Arg Ile Glu Arg Ile Arg Ser Glu
    2795            2800                2805

His Ala Glu Thr Trp Phe Phe Asp Glu Asn His Pro Tyr Arg Thr
    2810            2815                2820

Trp Ala Tyr His Gly Ser Tyr Glu Ala Pro Thr Gln Gly Ser Ala
    2825            2830                2835

Ser Ser Leu Ile Asn Gly Val Val Arg Leu Leu Ser Lys Pro Trp
    2840            2845                2850

Asp Val Val Thr Gly Val Thr Gly Ile Ala Met Thr Asp Thr Thr
    2855            2860                2865

Pro Tyr Gly Gln Gln Arg Val Phe Lys Glu Lys Val Asp Thr Arg
    2870            2875                2880

Val Pro Asp Pro Gln Glu Gly Thr Arg Gln Val Met Ser Met Val
    2885            2890                2895

Ser Ser Trp Leu Trp Lys Glu Leu Gly Lys His Lys Arg Pro Arg
    2900            2905                2910

Val Cys Thr Lys Glu Glu Phe Ile Asn Lys Val Arg Ser Asn Ala
    2915            2920                2925

Ala Leu Gly Ala Ile Phe Glu Glu Lys Glu Trp Lys Thr Ala
    2930            2935                2940

Val Glu Ala Val Asn Asp Pro Arg Phe Trp Ala Leu Val Asp Lys
    2945            2950                2955

Glu Arg Glu His His Leu Arg Gly Glu Cys Gln Ser Cys Val Tyr
    2960            2965                2970

Asn Met Met Gly Lys Arg Glu Lys Lys Gln Gly Glu Phe Gly Lys
    2975            2980                2985

Ala Lys Gly Ser Arg Ala Ile Trp Tyr Met Trp Leu Gly Ala Arg
    2990            2995                3000

Phe Leu Glu Phe Glu Ala Leu Gly Phe Leu Asn Glu Asp His Trp
    3005            3010                3015

Met Gly Arg Glu Asn Ser Gly Gly Gly Val Glu Gly Leu Gly Leu
    3020            3025                3030

Gln Arg Leu Gly Tyr Val Leu Glu Glu Met Ser Arg Ile Pro Gly
    3035            3040                3045

Gly Arg Met Tyr Ala Asp Asp Thr Ala Gly Trp Asp Thr Arg Ile
    3050            3055                3060

Ser Arg Phe Asp Leu Glu Asn Glu Ala Leu Ile Thr Asn Gln Met
    3065            3070                3075

Glu Lys Gly His Arg Ala Leu Ala Leu Ala Ile Ile Lys Tyr Thr
    3080            3085                3090

Tyr Gln Asn Lys Val Val Lys Val Leu Arg Pro Ala Glu Lys Gly
    3095            3100                3105

Lys Thr Val Met Asp Ile Ile Ser Arg Gln Asp Gln Arg Gly Ser
    3110            3115                3120

Gly Gln Val Val Thr Tyr Ala Leu Asn Thr Phe Thr Asn Leu Val
    3125            3130                3135

Val Gln Leu Ile Arg Asn Met Glu Ala Glu Glu Val Leu Glu Met
    3140            3145                3150

Gln Asp Leu Trp Leu Leu Arg Arg Ser Glu Lys Val Thr Asn Trp
    3155            3160                3165
```

Leu Gln Ser Asn Gly Trp Asp Arg Leu Lys Arg Met Ala Val Ser
3170                3175                3180

Gly Asp Asp Cys Val Val Lys Pro Ile Asp Asp Arg Phe Ala His
3185                3190                3195

Ala Leu Arg Phe Leu Asn Asp Met Gly Lys Val Arg Lys Asp Thr
3200                3205                3210

Gln Glu Trp Lys Pro Ser Thr Gly Trp Asp Asn Trp Glu Glu Val
3215                3220                3225

Pro Phe Cys Ser His His Phe Asn Lys Leu His Leu Lys Asp Gly
3230                3235                3240

Arg Ser Ile Val Val Pro Cys Arg His Gln Asp Glu Leu Ile Gly
3245                3250                3255

Arg Ala Arg Val Ser Pro Gly Ala Gly Trp Ser Ile Arg Glu Thr
3260                3265                3270

Ala Cys Leu Ala Lys Ser Tyr Ala Gln Met Trp Gln Leu Leu Tyr
3275                3280                3285

Phe His Arg Arg Asp Leu Arg Leu Met Ala Asn Ala Ile Cys Ser
3290                3295                3300

Ser Val Pro Val Asp Trp Val Pro Thr Gly Arg Thr Thr Trp Ser
3305                3310                3315

Ile His Gly Lys Gly Glu Trp Met Thr Thr Glu Asp Met Leu Val
3320                3325                3330

Val Trp Asn Arg Val Trp Ile Glu Glu Asn Asp His Met Glu Asp
3335                3340                3345

Lys Thr Pro Val Thr Lys Trp Thr Asp Ile Pro Tyr Leu Gly Lys
3350                3355                3360

Arg Glu Asp Leu Trp Cys Gly Ser Leu Ile Gly His Arg Pro Arg
3365                3370                3375

Thr Thr Trp Ala Glu Asn Ile Lys Asn Thr Val Asn Met Val Arg
3380                3385                3390

Arg Ile Ile Gly Asp Glu Glu Lys Tyr Met Asp Tyr Leu Ser Thr
3395                3400                3405

Gln Val Arg Tyr Leu Gly Glu Glu Gly Ser Thr Pro Gly Val Leu
3410                3415                3420

<210> SEQ ID NO 21
<211> LENGTH: 12
<212> TYPE: DNA
<213> ORGANISM: Artificial Sequence
<220> FEATURE:
<223> OTHER INFORMATION: Synthetic construct

<400> SEQUENCE: 21
ggatccggta cc                                                          12

<210> SEQ ID NO 22
<211> LENGTH: 12
<212> TYPE: DNA
<213> ORGANISM: Artificial Sequence
<220> FEATURE:
<223> OTHER INFORMATION: Synthetic construct

<400> SEQUENCE: 22
gctagcgaat tc                                                          12

<210> SEQ ID NO 23
<211> LENGTH: 6
<212> TYPE: DNA

```
<213> ORGANISM: Artificial Sequence
<220> FEATURE:
<223> OTHER INFORMATION: Synthetic construct]

<400> SEQUENCE: 23 gccacc                                                                     6

<210> SEQ ID NO 24
<211> LENGTH: 2121
<212> TYPE: DNA
<213> ORGANISM: Artificial Sequence
<220> FEATURE:
<223> OTHER INFORMATION: Synthetic Construct

<400> SEQUENCE: 24
ggatccggta ccgccaccat gggcaaaaga tccgccggca gcatcatgtg gctggccagt           60
ctggctgtcg tgatcgcctg tgctggcgcc gccgaagtga ccagaagagg cagcgcctac         120
tacatgtacc tggaccggaa cgatgccggc gaggccatca gctttccaac cacccctggg         180
atgaacaagt gctacatcca gatcatggac ctggccacag tgtgcgacgc caccatgagc         240
tacgagtgcc ccatgctgga cgagggcgtg aacccgacg atgtggactg ctggtgcaac          300
accaccagca cctgggtggt gtacggcacc tgtcaccaca gaagggcga agccagaaga          360 agccggcggg ctgtgacact gcctagccac agcacccgga agctgcagac cagaagccag         420
acctggctgg aaagcagaga gtacaccaag cacctgatcc gggtggaaaa ctggatcttc         480
cggaaccccg gcttcgccct ggccgctgct gctattgctt ggctgctggg cagcagcacc         540
agccagaaag tgatctacct cgtgatgatc ctgctgatcg cccctgccta cagcatccgg         600
tgtatcggcg tgtccaaccg ggacttcgtg aaggcatga gcggcggcac atgggtggac          660
gtggtgctgg aacatggcgg ctgcgtgaca gtgatggccc aggacaagcc caccgtggac         720
atcgagctcg tgaccaccac cgtgtccaat atggccgaag tgcggagcta ctgctacgag         780
gccagcatca gcgacatggc cagcgacagc agatgcccta cagggcga ggcctacctg           840 gacaagcagt ccgacaccca gtacgtgtgc aagcggaccc tggtggatag aggctgggc          900 aatggctgcg gcctgtttgg caagggcagc ctcgtgacct cgccaagtt cgcctgcagc          960 aagaagatga ccggcaagag catccagccc gagaacctgg aataccggat catgctgagc        1020
gtgcacggca gccagcactc cggcatgatc gtgaacgaca ccggccacga cagacgagag        1080
aaccgggcca aggtggaaat caccccccaa cagccctaga ccgaggccac actgggcggc        1140
tttggatctc tgggcctgga ctgcgagcct agaaccggcc tggatttcag cgacctgtac        1200
tacctgacca tgaacaacaa acactggctg gtgcacaaag agtggttcca cgacatcccc        1260 ctgcccctggc atgccggcgc tgatacaggc acaccccact ggaacaacaa agaggccctg        1320
gtggagttca aggacgccca cgccaagagg cagaccgtgg tggtgctggg atctcaggaa        1380
ggcgccgtgc atacagctct ggctggcgcc ctggaagccg aaatggatgg cgctaagggc        1440
agactgtcca gcgccacct gaagtgccgg ctgaagatgg acaagctgcg gctgaagggc          1500
gtgtcctaca gcctgtgtac cgccgccttc accttcacca agatccccgc cgagacactg        1560
cacggcaccg tgactgtgga agtgcagtac gccggcaccg acggcccttg taaagtgcct        1620
gctcagatgg ccgtggatat gcagaccctg acccctgtgg gcaggctgat caccgccaac        1680
cctgtgatca ccgagagcac cgagaacagc aagatgatgc tggaactgga cccacccttc        1740
ggcgacagct acatcgtgat cggcgtggga gagaagaaga tcacccacca ctggcacaga        1800
agcggcagca ccatcggcaa ggcctttgag gctacagtgc ggggagccaa gagaatggcc        1860
```

```
gtgctgggag ataccgcctg ggactttggc tctgtgggcg agccctgaa ctctctgggc    1920 aagggaatcc accagatctt cggcgctgcc ttcaagagcc tgttcggcgg catgagctgg    1980
ttcagccaga tcctgatcgg caccctgctg atgtggctgg gcctgaacac caagaacggc    2040
tccatcagcc tgatgtgcct ggctctggga ggcgtgctga tcttcctgag cacagccgtg    2100
tccgcctgag ctagcgaatt c                                              2121
```

```
<210> SEQ ID NO 25
<211> LENGTH: 696
<212> TYPE: PRT
<213> ORGANISM: Artificial Sequence
<220> FEATURE:
<223> OTHER INFORMATION: Synthetic Construct

<400> SEQUENCE: 25

Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
```

```
            305                 310                 315                 320
        Ser Ile Gln Pro Glu Asn Leu Glu Tyr Arg Ile Met Leu Ser Val His
                        325                 330                 335

Gly Ser Gln His Ser Gly Met Ile Val Asn Asp Thr Gly His Glu Thr
                        340                 345                 350

Asp Glu Asn Arg Ala Lys Val Glu Ile Thr Pro Asn Ser Pro Arg Ala
                        355                 360                 365

Glu Ala Thr Leu Gly Gly Phe Gly Ser Leu Gly Leu Asp Cys Glu Pro
                    370                 375                 380

Arg Thr Gly Leu Asp Phe Ser Asp Leu Tyr Tyr Leu Thr Met Asn Asn
        385                 390                 395                 400

Lys His Trp Leu Val His Lys Glu Trp Phe His Asp Ile Pro Leu Pro
                        405                 410                 415

Trp His Ala Gly Ala Asp Thr Gly Thr Pro His Trp Asn Asn Lys Glu
                        420                 425                 430

Ala Leu Val Glu Phe Lys Asp Ala His Ala Lys Arg Gln Thr Val Val
                        435                 440                 445

Val Leu Gly Ser Gln Glu Gly Ala Val His Thr Ala Leu Ala Gly Ala
                    450                 455                 460

Leu Glu Ala Glu Met Asp Gly Ala Lys Gly Arg Leu Ser Ser Gly His
        465                 470                 475                 480

Leu Lys Cys Arg Leu Lys Met Asp Lys Leu Arg Leu Lys Gly Val Ser
                        485                 490                 495

Tyr Ser Leu Cys Thr Ala Ala Phe Thr Phe Thr Lys Ile Pro Ala Glu
                        500                 505                 510

Thr Leu His Gly Thr Val Thr Val Glu Val Gln Tyr Ala Gly Thr Asp
                        515                 520                 525

Gly Pro Cys Lys Val Pro Ala Gln Met Ala Val Asp Met Gln Thr Leu
                    530                 535                 540

Thr Pro Val Gly Arg Leu Ile Thr Ala Asn Pro Val Ile Thr Glu Ser
        545                 550                 555                 560

Thr Glu Asn Ser Lys Met Met Leu Glu Leu Asp Pro Pro Phe Gly Asp
                        565                 570                 575

Ser Tyr Ile Val Ile Gly Val Gly Glu Lys Lys Ile Thr His His Trp
                        580                 585                 590

His Arg Ser Gly Ser Thr Ile Gly Lys Ala Phe Glu Ala Thr Val Arg
                        595                 600                 605

Gly Ala Lys Arg Met Ala Val Leu Gly Asp Thr Ala Trp Asp Phe Gly
                    610                 615                 620

Ser Val Gly Gly Ala Leu Asn Ser Leu Gly Lys Gly Ile His Gln Ile
        625                 630                 635                 640

Phe Gly Ala Ala Phe Lys Ser Leu Phe Gly Met Ser Trp Phe Ser
                        645                 650                 655

Gln Ile Leu Ile Gly Thr Leu Leu Met Trp Leu Gly Leu Asn Thr Lys
                        660                 665                 670

Asn Gly Ser Ile Ser Leu Met Cys Leu Ala Leu Gly Gly Val Leu Ile
                        675                 680                 685

Phe Leu Ser Thr Ala Val Ser Ala
                    690                 695

<210> SEQ ID NO 26
<211> LENGTH: 2121
<212> TYPE: DNA
<213> ORGANISM: Artificial Sequence
```

<220> FEATURE:
<223> OTHER INFORMATION: Synthetic Construct

<400> SEQUENCE: 26

| | | | | | |
|---|---|---|---|---|---:|
| ggatccggta | ccgccaccat | gggcaaaaga | tccgccggca | gcatcatgtg gctggccagt | 60 |
| ctggctgtcg | tgatcgcctg | tgctggcgcc | gccgaagtga | ccagaagagg cagcgcctac | 120 |
| tacatgtacc | tggaccggaa | cgatgccggc | gaggccatca | gctttccaac caccctgggc | 180 |
| atgaacaagt | gctacatcca | gatcatggac | ctggccaca | tgtgcgacgc caccatgagc | 240 |
| tacgagtgcc | ccatgctgga | cgagggcgtg | gaacccgacg | atgtggactg ctggtgcaac | 300 |
| accaccagca | cctgggtggt | gtacggcacc | tgtcaccaca | gaagggcga agccagaaga | 360 |
| agccggcggg | ctgtgacact | gcctagccac | agcacccgga | agctgcagac cagaagccag | 420 |
| acctggctgg | aaagcagaga | gtacaccaag | cacctgatcc | gggtgaaaaa ctggatcttc | 480 |
| cggaaccccg | gcttcgccct | ggccgctgct | gctattgctt | ggctgctggg cagcagcacc | 540 |
| agccagaaag | tgatctacct | cgtgatgatc | ctgctgatcg | cccctgccta cagcatccgg | 600 |
| tgtatcggcg | tgtccaaccg | ggacttcgtg | aaggcatga | gcggcggcac atgggtggac | 660 |
| gtggtgctga | acatggcgg | ctgcgtgaca | gtgatggccc | aggacaagcc caccgtggac | 720 |
| atcgagctcg | tgaccaccac | cgtgtccaat | atggccgaag | tgcggagcta ctgctacgag | 780 |
| gccagcatca | gcgacatggc | cagcgacagc | agatgcccta | cagggcga ggcctacctg | 840 |
| gacaagcagt | ccgacaccca | gtacgtgtgc | aagcggaccc | tggtggatag aggctggggc | 900 |
| aatggctgcg | gcctgtttgg | caagggcagc | ctcgtgacct | cgccaagtt cgcctgcagc | 960 |
| aagaagatga | ccggcaagag | catccagccc | gagaacctgg | aataccggat catgctgagc | 1020 |
| gtgcacggca | gccagcactc | cggcatgatc | gtgaacgaca | ccggccacga gacagacgag | 1080 |
| aaccgggcca | aggtggaaat | cacccccaac | agccctagag | ccgaggccac actgggcggc | 1140 |
| tttggatctc | tgggcctgga | ctgcgagcct | agaaccggcc | tggatttcag cgacctgtac | 1200 |
| tacctgacca | tgaacaacaa | acactggctg | gtgcacaaag | agtggttcca cgacatcccc | 1260 |
| ctgccctggc | atgccggcgc | tgatacaggc | acacccact | ggaacaacaa agaggccctg | 1320 |
| gtggagttca | aggacgccca | cgccaagagg | cagaccgtgg | tggtgctggg atctcaggaa | 1380 |
| ggcgccgtgc | atacagctct | ggctggcgcc | ctggaagccg | aaatggatgg cgctaagggc | 1440 |
| agactgtcca | gcgccacct | gaagtgccgg | ctgaagatgg | acaagctgcg gctgaagggc | 1500 |
| gtgtcctaca | gcctgtgtac | cgccgccttc | accttcacca | agatccccgc cgagacactg | 1560 |
| cacggcaccg | tgactgtgga | agtgcagtac | gccggcaccg | acggcccttg taaagtgcct | 1620 |
| gctcagatgg | ccgtggatat | gcagaccctg | acccctgtgg | gcaggctgat caccgccaac | 1680 |
| cctgtgatca | ccgagagcac | cgagaacagc | aagatgatgc | tggaactgga cccacccttc | 1740 |
| ggcgacagct | acatcgtgat | cggcgtggga | gagaagaaga | tcacccacca ctggcacaga | 1800 |
| agcggcagca | ccctgggcaa | ggcctttagc | accacactga | agggcgccca gagactggcc | 1860 |
| gccctgggag | atacagcctg | gactttggc | tctatcggcg | gcgtgttcaa cagcatcggc | 1920 |
| aaggccgtgc | accaggtgtt | cggcggagcc | ttcagaaccc | tgtttggcgg catgagctgg | 1980 |
| atcacccagg | gcctgatggg | agccctgctg | ctgtggatgg | gagtgaacgc ccgggacaga | 2040 |
| tctatcgccc | tggcctttct | ggccaccggc | ggagtgctgg | tgttcctggc cacaaatgtg | 2100 |
| cacgcctgag | ctagcgaatt | c | | | 2121 |

<210> SEQ ID NO 27

<211> LENGTH: 696
<212> TYPE: PRT
<213> ORGANISM: Artificial Sequence
<220> FEATURE:
<223> OTHER INFORMATION: Synthetic Construct

<400> SEQUENCE: 27

Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

-continued

```
Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Leu Gly Lys Ala Phe Ser Thr Thr Leu Lys
        595                 600                 605

Gly Ala Gln Arg Leu Ala Ala Leu Gly Asp Thr Ala Trp Asp Phe Gly
    610                 615                 620

Ser Ile Gly Gly Val Phe Asn Ser Ile Gly Lys Ala Val His Gln Val
625                 630                 635                 640

Phe Gly Gly Ala Phe Arg Thr Leu Phe Gly Gly Met Ser Trp Ile Thr
                645                 650                 655

Gln Gly Leu Met Gly Ala Leu Leu Leu Trp Met Gly Val Asn Ala Arg
            660                 665                 670

Asp Arg Ser Ile Ala Leu Ala Phe Leu Ala Thr Gly Gly Val Leu Val
        675                 680                 685

Phe Leu Ala Thr Asn Val His Ala
    690                 695
```